United States Patent
Akram et al.

(10) Patent No.: US 12,408,235 B2
(45) Date of Patent: Sep. 2, 2025

(54) SYSTEMS, METHODS, MEDIA, ARCHITECTURE AND GRAPHICAL USER INTERFACES FOR RAPID RESPONSE SYSTEMS

(71) Applicant: Ositech Communications Inc., Guelph (CA)

(72) Inventors: Tahir Akram, Guelph (CA); Zahid Akram, Tarpon Springs, FL (US); Zakir Akram, Guelph (CA)

(73) Assignee: Ositech Communications Inc., Guelph (CA)

( * ) Notice: Subject to any disclaimer, the term of this patent is extended or adjusted under 35 U.S.C. 154(b) by 215 days.

(21) Appl. No.: 17/912,669

(22) PCT Filed: Mar. 30, 2021

(86) PCT No.: PCT/CA2021/050414
§ 371 (c)(1),
(2) Date: Sep. 19, 2022

(87) PCT Pub. No.: WO2021/195754
PCT Pub. Date: Oct. 7, 2021

(65) Prior Publication Data
US 2023/0162845 A1 May 25, 2023

Related U.S. Application Data

(60) Provisional application No. 63/002,225, filed on Mar. 30, 2020.

(51) Int. Cl.
*H04W 76/50* (2018.01)
*G16H 40/20* (2018.01)
(Continued)

(52) U.S. Cl.
CPC ............ *H04W 76/50* (2018.02); *H04W 4/02* (2013.01); *H04W 4/029* (2018.02); *H04W 4/06* (2013.01);
(Continued)

(58) Field of Classification Search
None
See application file for complete search history.

(56) References Cited

U.S. PATENT DOCUMENTS 8,684,922 B2 * 4/2014 Tran ...................... G09B 19/00
600/300
9,491,277 B2 * 11/2016 Vincent ................... H04W 4/90
(Continued)

FOREIGN PATENT DOCUMENTS

| CA | 2780811 | 5/2011 |
|---|---|---|
| CA | 3096212 | 10/2019 |

(Continued)

OTHER PUBLICATIONS

Extended European Search Report dated Mar. 21, 2024; European Patent No. 21781533.1.
(Continued)

*Primary Examiner* — Adolf Dsouza
(74) *Attorney, Agent, or Firm* — Rowand LLP

(57) ABSTRACT

Methods and systems for improving rapid response to crisis events in a supervised care environment. A system obtains location information regarding a crisis event from a first mobile device and notifies associated team members' respective mobile devices, providing the location information. The locations of the team members' mobile devices and their respective arrival at the location of the crisis event may be tracked and recorded. Patient data and vital signs may be pushed to each mobile device, and checklists may be displayed appropriate to each members' respective role.

26 Claims, 49 Drawing Sheets

(51) Int. Cl.
*H04W 4/02* (2018.01)
*H04W 4/029* (2018.01)
*H04W 4/06* (2009.01)
*H04W 4/80* (2018.01)
*H04W 4/90* (2018.01)
*H04W 64/00* (2009.01)

(52) U.S. Cl.
CPC .............. *H04W 4/80* (2018.02); *H04W 4/90* (2018.02); *H04W 64/003* (2013.01); *G16H 40/20* (2018.01)

(56) References Cited

U.S. PATENT DOCUMENTS

| | | | |
|---|---|---|---|
| 9,734,690 B2 * | 8/2017 | Haflinger | G08B 25/08 |
| 9,814,425 B2 * | 11/2017 | Tran | G16Z 99/00 |
| 10,270,899 B1 | 4/2019 | Merjanian et al. | |
| 10,565,845 B1 | 2/2020 | Beyer et al. | |

FOREIGN PATENT DOCUMENTS

| | | |
|---|---|---|
| WO | WO2016011190 | 1/2016 |
| WO | WO2018178358 | 10/2018 |

OTHER PUBLICATIONS

International Search Report & Written Opinion dtd Jul. 7, 2021, Application No. PCT/CA2021/050414.
Canadian Office Action dated Oct. 24, 2023; Application No. 3,170,940.
CA Office Action dated Jul. 11, 2025; Application No. 3,170,940.

* cited by examiner

… (US 12,408,235 B2)

SYSTEMS, METHODS, MEDIA, ARCHITECTURE AND GRAPHICAL USER INTERFACES FOR RAPID RESPONSE SYSTEMS

CROSS-REFERENCE TO RELATED APPLICATIONS

The present application claims priority to U.S. Provisional Patent Application No. 63/002,225 filed Mar. 30, 2020, the contents of which are hereby incorporated by reference.

FIELD OF INVENTION

The present technology pertains to rapid response systems in medical environments.

BACKGROUND

Medical environments, such as hospitals or other supervisory care environments, like long term care facilities, prisons, mental health wards, or the like, may provide care in teams of providers. Each team may be made up of a number of different generalist or specialist personnel, each having a set of roles and responsibilities, some of which may be distinct and some of which may overlap.

When a crisis occurs in connection with a person under care, the members of the care team need to be alerted and assembled as quickly as possible to address the crisis. To use a hospital as an example, this typically involves a nurse identifying the crisis event, possibly due to a family member other person observing a crisis event, and the nurse then contacting a hospital switchboard or operator to request that the team members be paged. A general auditory page is then sent throughout the hospital facility using the overhead speaker system. The page is typically coded or cryptic to avoid disclosing patient details and/or alarming family members. In response, it is hoped that team members will hear the page and identify it as pertaining to their team, upon which they will attempt to locate where the crisis occurred and make their way to that location. On arrival each team member will then help to ascertain what has occurred and how each one of them can assist in addressing the crisis. Afterwards, one or more of the team members may be tasked with creating detailed record of the crisis, including which team members arrived on scene, when, and what was done.

It would be advantageous to improve the responsiveness, performance, efficiency, and/or accuracy of current systems for handling medical crises in supervisory care environments.

BRIEF DESCRIPTION OF THE DRAWINGS

The accompanying drawings, where like reference numerals refer to identical or functionally similar elements throughout the separate views, together with the detailed description below, are incorporated in and form part of the specification, and serve to further illustrate embodiments of concepts that include the claimed disclosure, and explain various principles and advantages of those embodiments.

The methods and systems disclosed herein have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

FIGS. 1C-37 are exemplary views of interactive graphical user interfaces.

DETAILED DESCRIPTION

Figure 1A:
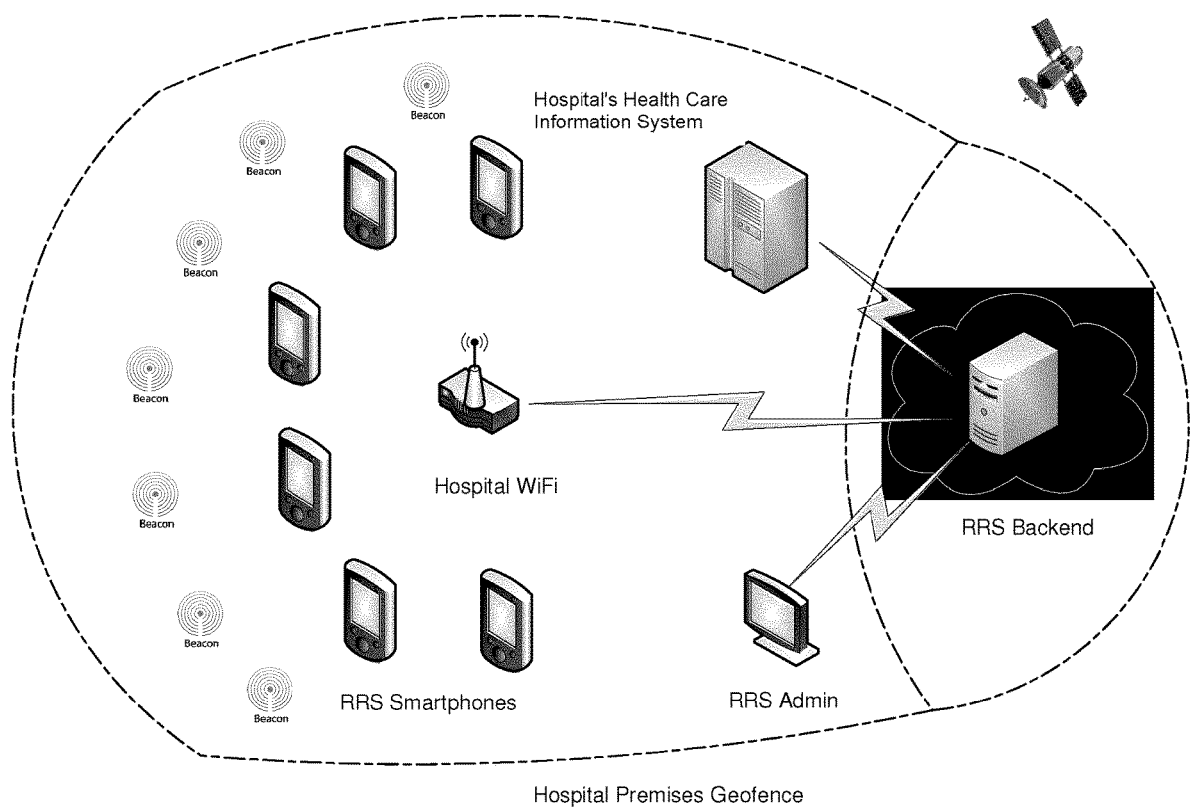
FIG. 1A is an exemplary hospital premises geofence.

In one aspect, the present application provides a method of crisis response for a patient in a supervisory care environment. The method may include receiving, at a server, a crisis event notification from a first member mobile device, including a patient identifier and a first team member identifier; determining a location associated with the crisis event notification; identifying, from stored team member data, a plurality of team member identifiers on a team with the first team member identifier; and transmitting notifications to respective mobile devices associated with the plurality of team member identifiers, the notifications including the location.

In another aspect, the present application provides a method of crisis response for a patient in a supervisory care environment. The method may include transmitting notifications from a server to respective mobile devices associated with a plurality of team member identifiers regarding a crisis event, the notifications including a location of the crisis event; receiving, at the server, location data regarding each of the team members; and detecting arrival of a team member at the location and logging an arrival time in association with the crisis event and the team member identifier for the team member.

In yet another aspect, the present application provides a method of crisis response for a patient in a supervisory care environment. The method may include receiving, via a first mobile device, a user input indicating a crisis event; determining a location of the first mobile device based on receiving a location signal; transmitting a crisis event notification to a server, including a patient identifier, a first member identifier, and the location; receiving an acknowledgment from the server and receiving status information regarding each of a plurality of team members associated with the first member identifier; and displaying the status information on the first mobile device.

In a further aspect, the present application provides one or more mobile devices having a processor, memory, and storing processor-executable instructions that, when executed, cause the processor to carry out the operations of one or more of the methods described herein.

In yet a further aspect, the present application describes a server having a processor, memory, and storing processor-executable instructions that, when executed, cause the processor to carry out the operations of one or more of the methods described herein.

While the present technology is susceptible of embodiment in many different forms, there is shown in the drawings and will herein be described in detail several specific embodiments with the understanding that the present disclosure is to be considered as an exemplification of the principles of the present technology and is not intended to limit the technology to the embodiments illustrated.

The purpose of a Rapid Response System (RRS) is to prevent patient mortality from preventable complications in the hospital. The RRS is a set of defined procedures and actions that are to be implemented by the Rapid Response Team (RRT) members. The RRT model is based on the assumption that immediate availability of an emergency team of experts, summoned by the staff who recognize symptoms of patient complication, can treat early deterioration and prevent emergent issues on medical/surgical floors, areas whose resources are stretched and when faced with unanticipated events.

Depending on the Hospital, the RRT may include all or some of the following personnel.

PCT—Patient Care Technician
HTO—Hospital Telephone Operator
PCN—Primary Care Nurse
PCL—Patient Care Leader
CHN—Charge Nurse
CCN—Critical Care Nurse (SWAT Nurse)
AOD—Administrator on Duty
RT—Respiratory Therapist
LT—Lab Technician
PHARM—Pharmacist
APRN—Advanced Practice Registered Nurse
MD—Physician A brief general description of the role and responsibility of each RRT member as it relates to the Rapid Response System in a typical hospital is given below. The role and responsibilities of these personnel in a hospital are significantly more and complex.

Patient Care Technician (PCT): Works closely with patients, in conjunction with Primary Care Nurse. They perform basic care for patients, such as assisting them in using restroom, serving meals or changing bedding. They may also monitor vital signs and provide emotional support to patients and their families. The PCT or the PCN are typically the people who would call the HTO to activate the RRT as they are in regular contact with the patient.

Hospital Telephone Operator (HTO): The HTO has a key role in the current RRS in alerting the various members of the RRT through direct calling on dedicated radio phones and paging using approved terminology.

Primary Care Nurse (PCN): The PCN is the nurse assigned to one or more patients and is most familiar with the patient's medical background. PCN is responsible for taking patient's vital signs, recording this data, administering authorized medications, reporting any adverse changes in patient's condition to the Physician and other medical staff. As a key member of the RRT, the PCN is the person most likely to activate the RRT. The PCN in consultation with the PCL and/or CHN and CCN determines the Suspected Cause of the Patient's deteriorating condition.

Patient Care Leader (PCL): The PCL is a senior nurse overseeing the Patient Care by PCNs. The PCL assists the PCN in determining the Suspected Cause of patient's deteriorating condition.

Charge Nurse (CHN): A senior nurse, the CHN is responsible for the operation of the nursing activities of a section or wing in the hospital. The CHN assists the PCN in determining the Suspected cause of patient's deteriorating condition.

Critical Care Nurse (CCN): The CCN is a core member and the focal point of the RRT. The CCN is typically a specially trained nurse and has the qualification and experience to assess patient's situation and communicate with the Physician. In some hospitals, CCN can order or recommend tests such as X-Ray, CT Scan and lab tests based on the assessment as well as certain medications. Some hospitals require the CCN to get approval from the Physician for the tests and medications after providing verbal description of the patient's situation.

Administrator on Duty/Team Lead (AOD): The AD is a core member of the RRT team. The AOD is a senior nurse managing a group of PCNs and PCTs. The AOD also interacts with other departments such as ICU, PCU and Med Telemetry to ensure smooth transfer of patients to/from the floor to these departments.

Respiratory Therapist (RT): The RT is a core member of the RRT. The primary job of the RT as a RRT member is to maintain a patient's cardiopulmonary (heart and lung) function so that the patient can keep breathing.

Lab Technician (LT): The LT collect patient's tissue, blood and other bodily fluid samples and conduct tests as ordered by CCN/APRN/MD-LT is not part of RRT in some hospitals.

Pharmacist (PHARM): The Pharmacist is involved in dispensing medication as ordered by APRN/MD which will be administered by PCN/CCN. PHARM is not part of RRT in some hospitals.

Advanced Practice Registered Nurse (APRN): The APRN is a senior nurse with additional qualifications and certifications which qualifies the APRN to order certain medications without physician approval. Not all hospitals include APRN in the RRT.

Physician (MD): The attending Physician is the final authority in ordering appropriate actions, medications, and tests after reviewing the patient situation, background, assessment, and recommendation of the PCN and CCN. In the existing RRS, the CCN calls the Physician. Also, the Physician is alerted by the overhead page, but at times if the Physician did not hear the page or is busy with another patient, the MD participation may be delayed.

RRS in practice today: A patient's family member, PCT or PCN notices deterioration in the patient's condition. If the family member notices the deterioration, they would get the PCT or PCN to come and see the patient. The PCN decides that the condition calls for activating the RRT. The PCN dials special extension like 66 from a bedside or hospital phone and informs the HTO to activate the RRT and provides patients location. The HTO immediately contacts the CCN using a dedicated radio phone with the patient's location. The HTO then uses approved terminology to page the RRT over the hospital paging system. Upon hearing the RRT page, all team members immediately go to the paged location. At this stage none of the team member knows the root cause of the deterioration in patient's condition that has led to the RRT activation. They will find out only when they reach the patients location. The room number of the patient is typically not announced over the overhead page so as not to cause anxiety amongst the family. The CCN upon receiving the call from the HTO immediately goes to the patient. The CCN is trained to assess the patient's conditions and make some preliminary determination. If the MD has not yet responded, the CCN calls the MD and may have to wait until either the MD arrives or answers the call. The CCN then briefs the MD on the patient's situation. The MD orders the medications and other actions such as ordering a CT scan, X-Ray and other tests and if needed orders moving the patient to the Intensive Care Unit (ICU). The AOD then facilitates the transfer of the patient. This closes the RRS incident. From now onwards, hospitals standard operating procedures go into effect. The CCN goes back to the office and completes the paperwork such as approximate times of arrivals of various team members, initial assessment, the cause of the activation, the resulting actions, and the start to end time of the RRS incident. This information would be used by the hospital Quality Assurance—QA team to assess the performance of the RRS. Since the team members are typically unaware of the patient's room number and are unaware of the reason why the RRS was activated, upon arrival there is likely some discussions and questions as to the cause. To a patient's family member already under stress and watching intently, appearance of sometimes uncoordinated actions of the team increases their anxiety and concern and may give the impression of the hospital staff being unprepared. This often at times results in lower customer satisfaction scores.

It would be advantageous to have a system and method that provides improved responsiveness, performance, efficiency, and/or accuracy for handling medical crises in supervisory care environments.

In one aspect, the present application provides a system and method that determines a location of a crisis event based on receipt of a crisis event notification from a first team member mobile device. The system may then identify the team members and transmit a notification to the mobile devices of the team members that includes the location.

The location may be automatically determined by the first team member mobile device or a central server based on data from the first team member mobile device. The determination may be based on a real-time location system in some cases. The determination may be based on the first team member mobile device receiving a localized RF signal or scanning a local optical code or other item unique to the location, in some example implementations.

By automatically determining the location and providing the location information in a discrete notification addressed to team members, the system avoids having the team members searching for the crisis event based only on knowledge of a general area, or having to congregate at a nurses station or other gathering point before learning of which patient is involved and where the patient is located. This may improve response speed and clinical outcomes.

In another aspect, the present application may provide for a system and method that transmit notifications to team members regarding a crisis event with location data. It may then detect arrival of a team member at the location and log that arrival time in association with the crisis event and a team member identifier. This may ensure an accurate record of response time for each team member.

In yet another aspect, the present application may provide for a system and method in which a first team member may input a crisis event to a mobile device. The mobile device may determine its location based on receipt of a location signal, and may transmit a crisis event notification to a server including the location. Team members may then be notified of the crises by way of their own mobile devices, including the location information. Status information for each team member may be relayed from the server back to the first team member's mobile device for display.

In some cases, the system may providing checklists of actions for each team member. In some examples, this may save time and ensure all actions are carried out by the assigned member, meaning the RRT members do not have to memorize what needs to be done in each situation. In some implementations, patient vital signs and other updates may be entered by a team member and may be made instantly available to all other RRT members on their smartphones even though they are not yet at the patient's location. By the time each RRT member arrives they are fully aware of the reasons behind the RRS activation and know precisely who needs to do what and in precise order.

Advantageously, the described system and methods of the present application may reduce the total time from start to finish of handling a rapid response crisis event. The Physician may receive detailed and accurate information on the patient's situation, background, assessment, and recommendation, even prior to arrival at the location of the patient in some cases, which allows the Physician to make diagnosis and approve appropriate actions in a short time.

All of the above may lead to better outcomes for the patient. Also, the proposed system may enable detailed tracking of arrival times and steps taken by the team members, which can be used for event analysis and response time improvements.

Figure 38:
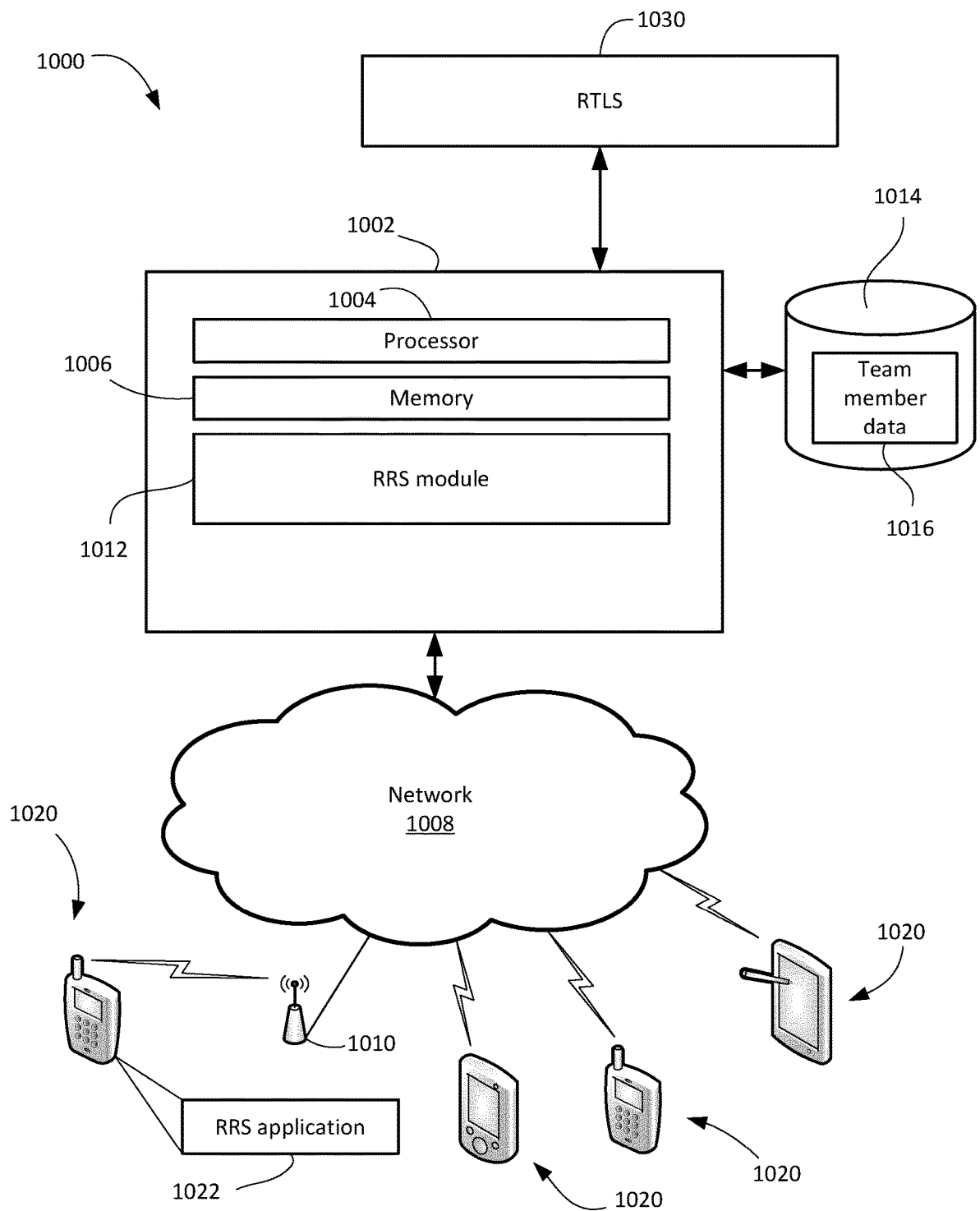
FIG. 38 is a simplified block diagram of an example system in accordance with one aspect of the present application.

Reference will now be made to FIG. 38, which diagrammatically illustrates one example system 1000 for managing a crisis event in a supervisory care environment, such as a hospital.

The example system 1000 may include a server 1002, which includes a processor 1004 and memory 1006, and which is connected to a network 1008. The network 1008 may be an internal network, or Intranet, within the supervisory care facility. The network may feature a plurality of wireless access points 1010 that provide for wireless network connectivity to the network 1008. The network 1008 may be an open network to which any device may attach, or may be a closed network to which only authorized devices may attach and communicate.

The server 1002 may include an RRS module 1012 for implementing functional operations described below. The RRS module 1012 may be implemented by way of one or more software modules or applications. The modules or applications may include processor-executable instructions that, when executed by the processor 1004, cause the processor 1004 to carry out the described functions.

It will be appreciated that the server 1002 may have additional components including user interface elements, one or more communications interfaces, operating system software and other such elements that are not shown for ease of illustration.

The server 1002 may include or may have access to a data store 1014 containing team member data 1016. The data store 1014 may be an integrated or external memory storage device, such as a solid state drive or other non-volatile memory device. The team member data 1016 may include team member identifiers corresponding to each team member and grouped or associated into teams. One or more members may be designated as alternate team members in case of unavailability of one of the team members. Multiple teams may be stored in the data store 1014. The team member data 1016 may further include associated mobile device data for each team member. The mobile device data may include contact information for the team member and associated mobile device data such as a network address on the network 1008. The mobile device data may be updated when a mobile device attaches to the network 1008.

In some cases, the team member data 1016 includes status information for the team member. The status information may include current availability. The current availability may be based on whether the associated mobile device is attached to the network 1008. In some instances, the current availability may be partly based on detection of the associated mobile device within a geofence around the supervisory care environment. In some instances, the current availability may be partly based on data from a facility security system that logs passcard usage at entry or exits points for the facility.

The system 1000 may include a real-time location system (RTLS) 1030. The RTLS 1030 may track the location of mobile devices within a facility, such as the supervisory care environment. In one embodiment, the RTLS 1030 may rely on GPS or other satellite location data. In another embodiment, the RTLS 1030 may rely on passcard check-in points at entry, exit, or other check-points in the facility. In another embodiment, the RTLS 1030 may rely on WiFi fingerprinting, in which a mobile device reports detected WiFi access points and, in some cases, signal strength measurements, to enable the RTLS 1030 to determine the location of the mobile device based on a WiFi mapping of the facility. In another embodiment, the RTLS 1030 may rely on Bluetooth™ or other short-range beacon signal reporting from mobile devices to determine the location of the mobile devices. Combination or sub-combinations of these or other RTLS mechanisms may be employed in some implementations.

Team members have associated mobile devices 1020 that may connect to the network 1008 via one of the wireless access points 1010. The mobile devices 1020 may have an RRS application 1022 installed. The RRS application 1022 may be configured to communicate with the RRS module 1012 on the server 1002 via the network 1008.

The mobile devices 1020 may include smartphones, tablets, personal digital assistants (PDSs), wearables, laptops, or any such mobile computing device having a display screen, one or more input devices, and wireless communication capabilities.

The RRS application 1022, when executed by a processor on the mobile device 1020, may cause the mobile device to send and receive communications with the RRS module 1012 and to output information to the display screen of the mobile device 1020. It may further cause the mobile device 1020 to output sensory notifications, such as audible alerts, vibratory alerts, or visual alerts. The mobile device 1020 may have a touchscreen for text input and may have a microphone and associated voice-to-text software for receiving auditory input. The mobile device 1020 may further have a camera for capturing photo or video input.

Figure 39:
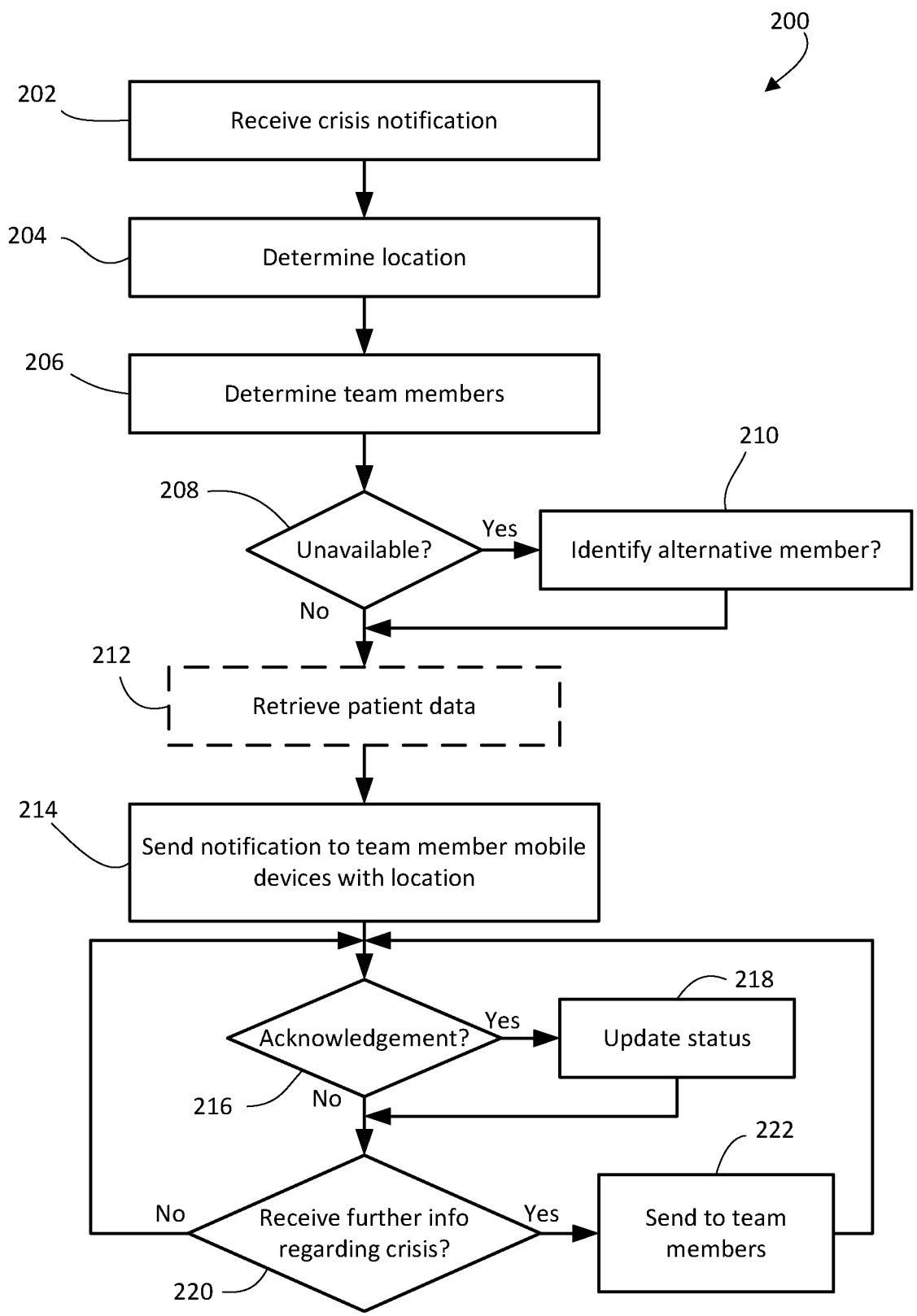
FIG. 39 shows, in flowchart form, one example method of facilitating crisis response in a supervisory care environment.

Reference will now be made to FIG. 39, which shows, in flowchart form, one example method 200 of crisis response for a patient in a supervisory care environment. The example method 200 may be implemented by way of processor-executable instructions stored in memory that, when executed by a processor, cause the processor to carry out the described operations. In some cases, the processor may be housed within a server connected to a network in the supervisory care environment. The instructions may be in the form of a module, routine, application, executable, or other file or format suitable to whichever language or programming environment is used in implementation.

The method 200 may include receiving a crisis notification at the server in operation 202. The crisis notification may be received from a first mobile device via the network. The crisis notification may include a team member identifier corresponding to the team member associated with the first mobile device. The crisis notification may include an identifier of the RRT application installed on the first mobile device, which is associated in memory at the server with the team member identifier. In some cases, the crisis notification includes a patient identifier. The patient identifier may include a patient name, a patient identification code, or other unique identifier for the patient. The first mobile device may have obtained the patient identifier through an optical scan of an encoded printed patient identifier, such as a barcode, QR code, or the like. The encoded printed patient identifier may be on a wristband, gown, or other patient-worn device, or may be on a patient chart, bed, or other patient-associated item. In some cases, the first mobile device may obtain the patient name through input via its input devices, such as a typed name or selected name from a drop down list.

In operation 204, the server automatically determines the location of the crisis event. In one implementation, the server automatically determines the location based on location data from the first mobile device. The location data may be sent with the crisis event notification or in a separate communication. In one example, the location data may include a code received by the first mobile device from a local short-range wireless device. The code may include a broadcast code from a beacon, such as a low energy localized wireless beacon. One example is a Bluetooth™ beacon. In another example, the location data may include one or more wireless access point identifiers, and may include signal strength measurements, which may be used to identify the location of the first mobile device using a wireless fingerprint map. In some cases, the location data may be obtained by querying an RTLS system, which may be part of the server or may be separate from the server but accessible to the server via the network. The RTLS system may use various mechanisms to track the location of mobile devices within the facility. A query to the RTLS system that includes an identity for the first mobile device may result in a response containing the location data. In yet a further example, the location data may be included in the crisis event notification and may be obtained by the first mobile device based on input received through a user interface. For example, the user initiating the crisis event notification may input or select a location.

In operation 206, the server identifies the team members. Identification of the team members may be based on stored team member data and the team member identifier associated with the crisis event notification. A search or query of the team member data may identify the team with which the team member identifier is associated. If the team member is associated with more than one team, then a collision resolution process may be triggered. In one implementation, the server may prompt the mobile device to display a "select team" screen on which are displayed the teams in which the team member is included and provide for selection of the displayed teams.

Once the team and its constituent team members are identified, then in operation 208 the server may determine whether any of the team members are unavailable. Each team member may have an associated mobile device identifier and/or availability status returned as part of the team member data. The server may determine, based on RTLS data, geofence data, network connectivity data, or other such information, whether the mobile devices associated with the team members are available. That is, whether they are present in the facility or whether the mobile devices are connected to the network and in communication with the server. For instance, when a team member arrives within the hospital premises, his or her mobile device may connect to the wireless network and the RRS application on the mobile device may connect to or register with the server to indicate its presence and availability.

If a mobile device associated with a team member is unavailable then in operation 210 the server may identify an alternative team member. The alternative team member may be specified in the team member data specific to that team, or may be a designated person or persons or category of person or persons.

In operation 212, the server may optionally obtain patient data from a patient data store. That is, the supervisory care environment and, in particular, the network, may have a patient record server containing patient data. The patient data may be comprehensive store of medical data and other personal information regarding the patients. For example, a hospital may have an electronic Healthcare Information System that stores electronic medical records. If that patient record server is available for access, assuming appropriate security protocols are in place to secure patient privacy, then the server may query the patient record server for patient information based on the patient identifier obtained in operation 202.

In operation 214, notifications are transmitted over the network to the mobile devices associated with the team members. The notifications may result in auditory, visual, and or vibratory alerts on the respective mobile devices. The notifications may include information regarding the crisis event. In particular, the notifications may include the location determined in operation 204. Additional information may also be provided in the notification, including any crisis-specific information specified in the crisis event notification, the time of the crisis, the patient identity, current patient vital signs if available, and any patient information retrieved in operation 212, if any.

The server may then receive an acknowledgement from one or more of the mobile devices associated with the team members and may log that acknowledgment in memory together with a time of acknowledgement in operation 216. Status information regarding the team members may be sent from the server to the first mobile device for display on the first mobile device, including whether those team members have acknowledged the notification. As indicated by operation 218, the status information may be updated as acknowledgements are received by the server.

In operation 220, the server may receive additional crisis information from the first mobile device. In response, it may provide that new crisis information to the mobile devices of the team members, as indicated by operation 222. Crisis information may include any information regarding crisis entered at the first mobile device, which may include text information, voice-to-text information, digital images captured by the first mobile device, checklist data, vital sign data, or other medical data entered on the first mobile device.

In some implementations, the server and RRS applications may employ a publish-subscribe model in which a crisis event data record is maintained by the server and each mobile device is a subscriber to the crisis event data record. Updates may be pushed to each subscriber device as they occur or the implementation may employ a polling model in which the subscriber devices periodically query the server for updates to the crisis event data record. Irrespective of the architectural model of implementation, the team member mobile devices are kept apprised of any patient data entered or recorded by the first mobile device to ensure that all team members have full patient information available as early as possible in the crisis.

Figure 40:
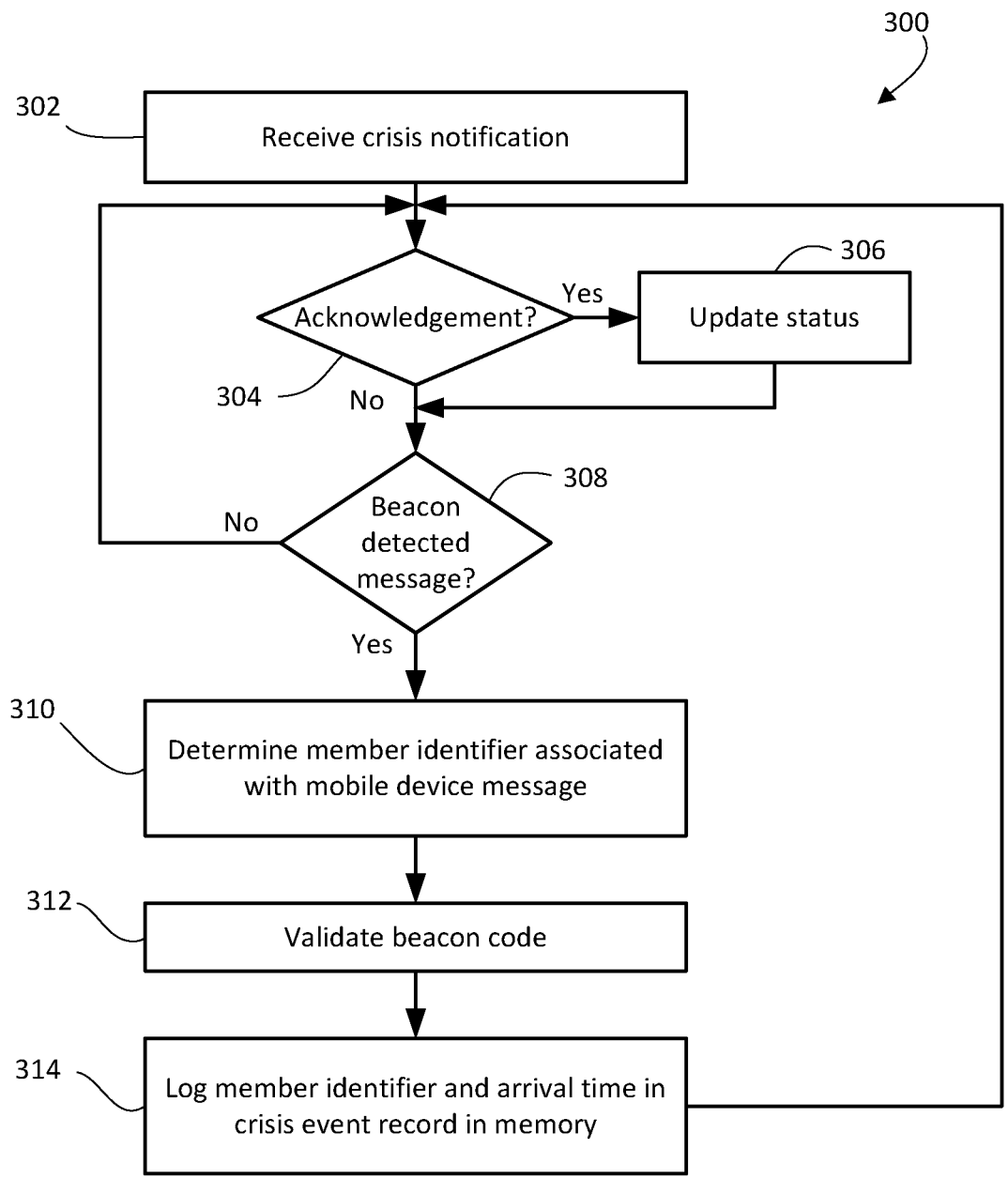
FIG. 40 shows, in flowchart form, one example method of logging crisis response events.

Reference will now be made to FIG. 40, which shows a flowchart of one example of a method 300 of logging crisis event response data in association with a crisis event. The method 300 may be implemented by way of processor-executable instructions stored in memory that, when executed by a processor, cause the processor to carry out the described operations. In some cases, the processor may be housed within a server connected to a network in the supervisory care environment. The instructions may be in the form of a module, routine, application, executable, or other file or format suitable to whichever language or programming environment is used in implementation.

The method 300 presumes that a crisis event has been initiated, for example by way of a crisis event notification from a first mobile device. The team members associated with the first mobile device have been identified together with their associated mobile devices. In operation 302, the server sends a notification regarding the crisis event to the mobile devices of the team members. As described above, the notification includes a location determined by the server. The location may be based on data received from the first mobile device or may be determined based on an RTLS or other location service that identifies the location of the first mobile device with the facility. In some implementations, the notification may further include a patient identifier, patient data, vital signs data, a checklist, etc.

In operation 304, if the server receives an acknowledgement from one of the mobile devices in response to the notification then it updates the status of that mobile device in operation 306. The acknowledgement may indicate that the notification was received in some cases. The acknowledgement may indicate that the user of the mobile device provided an acknowledgement input, such as selection of an "OK" button or the like indicating that the notification was displayed and read or otherwise acknowledged.

In operation 308, the server assesses whether it has received a beacon detected message from one of the mobile devices. Each mobile device, and in particular the RRS application on each mobile device, may be configured to listen for a beacon signal. The mobile devices may be configured to report each beacon signal identified, i.e. that every short-range local wireless beacon signal identified by the mobile device as it travels in the facility. In some instances, this may permit the server or a separate RTLS service to track the location of the mobile device within the facility as it encounters beacons having known locations in the facility.

In some other implementations, the mobile devices may be configured to report a particular beacon signal or beacon code provided in the notification. That is, the notification may specify a particular beacon code associated with a beacon. The beacon may be associated with the patient, the first mobile device, or the location. That is, the beacon may be a fixed beacon associated with the location identified by the first mobile device. The beacon code may be the same beacon code identified by the first mobile device in reporting the crisis event and may be the basis for determining the location of the crisis event. The beacon may be associated with patient and/or the patient's assigned bed. The beacon may be a beacon broadcast by the first mobile device, which may be configured to initiate output of the beacon signal by virtue of reporting the crisis event.

If the server receives a report of a detected beacon signal in operation 308, then in operation 310, it may identify the team member identifier associated with the mobile device reporting the beacon signal and in operation 312 it may validate the beacon code. Operation 312 may include determining whether the reported beacon code or signal matches the beacon code or signal associated with the crisis event, i.e. whether the mobile device has reported close proximity to the specific beacon broadcast at the location or by the first mobile device. If so, then in operation 314, the server logs the arrival of that associate team member at the crisis event. This may include storing in memory the team member identifier and an arrival time. The arrival log may be part of a crisis event record stored in memory for logging detected activities and actions in connection with the crisis event.

It will be appreciated that in some implementations, some operations of the described methods may be optional or may be modified without substantively altering the method. Some operations may be performed substantially or partly simultaneously while some may be performed in a different temporal order than is presented in these examples without altering the outcome. Those variations will be appreciated by those ordinarily skilled in the art.

Further detailed example embodiments will now be described in connection with an example implementation in a hospital setting.

DEFINITIONS

RRS Rapid Response System
RRT Rapid Response Team
PCT Patient Care Technician
HTO Hospital Telephone Operator
PCN Primary Care Nurse
PCL Patient Care Leader
CHN Charge Nurse
CCN Critical Care Nurse (SWAT Nurse)
AOD Administrator on Duty
RT Respiratory Therapist
LT Lab Technician
PHARM Pharmacist
APRN Advanced Practice Registered Nurse
MD Physician
SBAR Situation, Background, Assessment, Recommendation
SBARI Situation, Background, Assessment, Recommendation, Intervention
POC Proof of Concept
MVP Minimal Viable Product
FIG. 1A is an exemplary hospital premises geofence.
As illustrated in FIG. 1A:
RRT Smartphones: These could be hospital staff's personal phones (iPhone or Android) or dedicated Phones (iPhones or Android) that are used by the hospital staff when on duty and intended only for medical applications. If the Hospital authorizes the use of personal phones, the RRS backend system can enable or disable the RRS application when a member is not on hospital premises.

Hospital WiFi: For security reasons Hospitals will likely not allow cellular access to the RSS backend. All communication will be through the Hospital secure WiFi which will likely have an invisible SSID. The hospital infrastructure may or may not allow access to the outside world.

RRS Backend: This is the brain of the RRS that controls the flow of information between the members smartphones running the RRS application. The backend consists of a database and software that communicates with the RRS application running on the smartphones according to the rules and roles assigned to the members. Typical information in the database will have details of RRS members such as name, ID, email address, roles assigned to RRS members, shift information, availability status, record of all communication from the smartphones that are sent to other members and position/location information of the members. Depending on the hospital's security policy, the RRS backend can be implemented on a cloud platform such as AWS, Azure or Google using secure communications link from the hospital to the cloud or could be implemented entirely on a computer system housed within the hospital premises.

The RRS backend can operate standalone or for tighter integration, interface with the Healthcare Information System to retrieve certain patient and staff related information.

RTLS: The purpose of the RTLS component of the RRS is to provide the backend with the position/location information of the RRS team members and of certain equipment. Key component of the RTLS system are wireless beacons such as Bluetooth Low Energy Beacons placed in patient rooms, hallways, staff rooms, cafeteria and other locations in the hospital. Since each beacon has a unique identifier, it can identify a specific location within the hospital. The location of the beacons is stored in the database. Depending on the location, the transmit power of the beacons will be set to an appropriate level. Thus, beacons placed in a patient room would be set to low transmit levels such that only staff within few feet of the patient will be registered and not the staff in the adjoining room. Similarly, beacons in places such as cafeteria will be set to transmit at higher power to cover a larger area.

Each staff's phone will be set to receive the beacon and send that information to the backend which can use this information to determine the location. The staff's phone can also be set to receive beacons from other Bluetooth transmitters. By placing beacons on hospital equipment, the backend can then track the hospital equipment as well. By placing the beacons at hospital entrance and exits, the backend system can determine when a member has arrived or left the hospital.

The RTLS can also be used to track how often nursing staff is visiting a patient in the room.

The RTLS can use the GPS system to serve as a backup to determine if a team member is within the hospital premises. This could be used in case the Bluetooth beacon system is not implemented. Using the hospital coordinates and setting up a geofence, the RRS application will send information to the backend once the member enters or exits the geofence. The application will not send position/location information once the member is outside of the geofence to protect privacy.

The RTLS can also ensure patient record privacy. Rules can be implemented that allow or disallow access to patient information when outside of the hospital premises.

The RTLS system can also be used to locate optional team members or other hospital staff whose services may be required.

RRS Admin: This is the dashboard, used by the RRS administrator to add/delete RRS teams, members, members availability times, assign/change roles and generate various reports for statistical analysis, RRT effectiveness, details of specific RRT incidents, etc. Depending on the complexity of the frontend, the RRS Admin can be operated from a smartphone/tablet or a desktop PC.

RRS Smartphone Application

The Smartphone application is implemented for both the iPhones and Android phones and may be implemented for any other like devices. The application primarily communicates with the backend and displays various checklists that are shared between the team members in real time utilizing the backend as the controller.

Below is a list of example Smartphone App features:

Login/Logoff for RRT members (the same phone may be used by different people for hospital owned phones).

View availability status of team members and which ones have acknowledged or not acknowledged receiving the RRS notification Send and receive messages from team members. This messaging system does not use any social messaging platform to ensure security and privacy. Messages can contain audio, video clips and photos.

Receive alert messages and notifications from a specific RRT member.

Receive broadcast messages and notifications from other RRT members.

Enter patient's vital signs manually, via speech which is converted to text or capture from a Vital Sign Monitor wirelessly.

Capture photos or video clips of the equipment and if required, of the patient and attach to clinical notes or messages.

Display checklists of actions customized for the role of the RRT member.

Update checklists by checking/unchecking boxes, selection from drop down lists and direct entry either through keyboard or where possible voice.

Send/Receive checklists to/from other members based on the roles once the RRT has been activated.

Checklists sent can be recalled for modification by members who are authorized to make changes.

View previously received checklists. This can be done through a review checklist icon on the smartphone.

Enter Patient ID. This may be done by scanning the QR code on the patient wrist, speaking patient's name which is then converted to text and manual entry in the event the patient condition may not allow scanning the QR code on the wrist band or voice entry.

Determination of when (time stamp) a team member arrives at the patient's location. In some examples, this may be done without requiring any additional hardware such as a Bluetooth Tags. One approach is to configure the Smartphone of the PCN or whichever team member initiated the RRS event to become a BT Beacon transmitter when the RRS event is activated. The backend sends a specific beacon message to be transmitted by the RRS activating smartphone while all other members smartphones are told to listen for the specific beacon and report to the backend when a match is detected. As other team members arrive within the proximity of the PCN, their smartphone will recognize the beacon originating from the PCN smartphone and will report this to the backend which enables the backend to record the time when the message arrives from the smartphone and can then be used to determine how long it took a team member to arrive at the patient's location.

Once a team member arrives at the location and their mobile device detects the beacon, that team member's mobile device may also be configured to transmit a local beacon with the specific identifier.

The smartphone App on a RRT member's personal phone can use the BT beacons located at Hospital entrance and exit location together with GPS to determine when a team member is entering or exiting the hospital premises. When an RRT member enters the hospital, and it is their shift, the RRT member is prompted for logging in or acknowledging that they are ready to respond to RRS. When the RRT member leaves the hospital premises, the application is disabled and the RRT member cannot start the application. This method can enable a hospital to restrict access to patient medical records from outside of hospital premises.

RRS Smartphone App GUI

The following describes one implementation of the smartphone application.

The App will be started by a RRS member by pressing the RRS icon on the smartphone.

The first GUI page presented will have the Hospital Logo and a RRS logo separately or a combination of both.

If the member was not logged in, the login screen will be provided.

The STATUS screen is used to navigate to other screens such as TEAM, ADD EVENT, EVENT LIST and LOGOUT. It displays the logged in member ID and the role.

The current status of the team member can be viewed in the TEAM status screen by selecting TEAM from the status page. Also, from the team status page, messages between team members can be exchanged. This is a private messaging service and does not use the standard social media messaging platforms for enhanced security and patient confidentiality. The rules as to which team member can communicate with and whom they can communicate with are defined in the backend.

If the member had previously logged in, the member would see the EVENT LIST screen that will indicate any active RRS events. To proceed to the Patient Vital Signs and Checklists the member would tap the RRS event. The icon on the top left will display the status screen from where the new RRS event can be started, logout, view of team status and other functions. Even though it is unlikely that more than one RRS event may be in progress concurrently, the system is designed to handle such a situation. For each RRS event a timer indicates the time elapsed since activation of the RRS. The RRS event is also closed from the Event List screen.

Below each event are boxes for Closing Report, Labs And Diagnostics and Medications. The Closing Report provides a detailed summary of all actions relating to the RRS event. The Lab and Diagnostics tab provides a summary of Lab and Diagnostics checklist recommended and approved by the Physician. Only checked and approved items from the checklists are shown. The tab is grey and turns green when approval from Physician has been received. Team members such as Lab Technician and Pharmacist can use this as authorization to proceed as ordered. Similarly, the Medications tabs provides a summary of the medications from the Recommendation and Intervention Checklists. The tab is grey and provides no information until approval is received from the Physician when it turns green.

RRS event is created from the Status Page by selecting ADD EVENT. On the ADD EVENT screen, patient ID is entered either manually or scanning the QR code from the patient wristband. The location of the patient can be automatically populated if the RTLS system is being used, entered manually or by speaking the location which is then converted into text. By tapping the Activate button, the RRS event will start, and notification of the RRS event activation will be sent to all team members.

After the RRS system has been activated, patient VITAL SIGN screen is shown. Authorized members can enter and update the vital signs. The vital signs are immediately shared with all team members through the backend. The vital signs can be entered manually or by tapping the mic icon and speaking which is converted to text. The VITAL SIGNS screen also has provision to add notes manually or dictated and converted to text, take photos and videos and attach it to the Vital Signs screen which are accessible to authorized team members.

After the patient's VITAL SIGN Screen is completed, the SUSPECTED CAUSE screen is available to check one or more suspected causes. All vital signs must be entered before navigation to the suspected cause screen is allowed. The SUSPECTED CAUSE screen is shared with all team members instantly.

After the suspected cause screen, the SBARI (Situation, Background, Assessment, Recommendation and Intervention) screens can be viewed by all team members. Authorized team members now update the checklists which are instantly shared with all team members. Additional suspected causes can be added, or previously suspected causes can be removed by authorized members. Patient Vital Signs can be viewed and updated at any time from these checklists.

Checklists

The Smartphone App is built around checklists which will be displayed on the smartphone and will enable a member to view and/or modify depending on the role assigned to the team member. There can be a number of suspected causes that could be the reason for a patient's deteriorating condition. For each suspected cause, there are five types of checklists: Situation, Background, Assessment, Recommendation and Intervention. The following is an example of the checklist and who can View and Initiate/Modify these checklists. This may be modified based on a particular hospital's rules and requirements.

there are open WiFi networks for patient and or general public use. In such cases the Hospital staff would have to use the cellular connection for their personal use while the Smartphone App will communicate over the Hospital WiFi network. The Hospital secure network SSID will likely be not visible so the smartphone app will need to be configured to communicate over the invisible SSID.

RRS Backend

The Backend is the core of the RRS and may provide the following features:
Database of RRS members.
Phone (Personal or Hospital).
Name.
Role (PCT, PCN, CCN, AOD, LT, PHARM, HTO, APRN, MD).
Shift Time, Calendar.
Availability Status determined by login/logout from the phone and shift Calendar.

| Type | Name | View | Initiate/Modify by |
|---|---|---|---|
| CSCL | Cardiac Situation Checklist | All | PCN, PCL, CHN |
| CBCL | Cardiac Background Checklist | All | PCN, PCL, CHN |
| CACL | Cardiac Assessment Checklist | All | CCN, APRN, MD |
| CRCL | Cardiac Recommendation Checklist | All | CCN, APRN, MD |
| CICL | Cardiac Intervention Checklist | All | APRN, MD |
| RSCL | Respiratory Situation Checklist | All | PCN, PCL, CHN |
| RBCL | Respiratory Background Checklist | All | PCN, PCL, CHN |
| RACL | Respiratory Assessment Checklist | All | CCN, APRN, MD |
| RRCL | Respiratory Recommendation Checklist | All | CCN, APRN, MD |
| RICL | Respiratory Intervention Checklist | All | APRN, MD |
| NSCL | Neurological Situation Checklist | All | PCN, PCL, CHN |
| NBCL | Neurological Background Checklist | All | PCN, PCL, CHN |
| NACL | Neurological Assessment Checklist | All | CCN, APRN, MD |
| NRCL | Neurological Recommendation Checklist | All | CCN, APRN, MD |
| NICL | Neurological Intervention Checklist | All | APRN, MD |
| SSCL | Sepsis Situation Checklist | All | PCN, PCL, CHN |
| SBCL | Sepsis Background Checklist | All | PCN, PCL, CHN |
| SACL | Sepsis Assessment Checklist | All | CCN, APRN, MD |
| SRCL | Sepsis Recommendation Checklist | All | CCN, APRN, MD |
| SICL | Sepsis Intervention Checklist | All | APRN, MD |
| MSCL | Metabolic Situation Checklist | All | PCN, PCL, CHN |
| MBCL | Metabolic Background Checklist | All | PCN, PCL, CHN |
| MACL | Metabolic Assessment Checklist | All | CCN, APRN, MD |
| MRCL | Metabolic Recommendation Checklist | All | CCN, APRN, MD |
| MICL | Metabolic Intervention Checklist | All | APRN, MD |
| GSCL | Gastrointestinal Situation Checklist | All | PCN, PCL, CHN |
| GBCL | Gastrointestinal Background Checklist | All | PCN, PCL, CHN |
| GACL | Gastrointestinal Assessment Checklist | All | CCN, APRN, MD |
| GRCL | Gastrointestinal Recommendation Checklist | All | CCN, APRN, MD |
| GICL | Gastrointestinal Intervention Checklist | All | APRN, MD |
| ASCL | Anaphylaxis Situation Checklist | All | PCN, PCL, CHN |
| ABCL | Anaphylaxis Background Checklist | All | PCN, PCL, CHN |
| AACL | Anaphylaxis Assessment Checklist | All | CCN, APRN, MD |
| ARCL | Anaphylaxis Recommendation Checklist | All | CCN, APRN, MD |
| AICL | Anaphylaxis Intervention Checklist | All | APRN, MD |
| PSCL | Post-operative Situation Checklist | All | PCN, PCL, CHN |
| PBCL | Post-operative Background Checklist | All | PCN, PCL, CHN |
| PACL | Post-operative Assessment Checklist | All | CCN, APRN, MD |
| PRCL | Post-operative Recommendation Checklist | All | CCN, APRN, MD |
| PICL | Post-operative Intervention Checklist | All | APRN, MD |

Each of the above checklists, once completed, will be timestamped together with the members name who completed or last modified it. The latest modified checklist will be the active checklist however the backend will keep all modified checklist related to the incident so they can be viewed for QA and audit purposes.

RRT Smartphone to RSS Backend Communication

The smartphone may communicate with the RSS Backend over Hospital secure WiFi network. This should not pose any issue for Hospital issued smartphones. However, staff owned smartphones may pose a challenge in cases where Database of RRS Events. Detailed information on each RRS event is kept such as date and time, duration, team members participating, arrival times of each team member, record of Patient Vital signs, all changes made to vital signs timestamped and who made them, record of all filled checklists and modifications time stamped and who made them.

Database of checklist forms. The checklists can be adapted to a hospital's requirement. New checklists can be easily added, or existing ones modified.

A complete history of the RRS event from start to close including all audio and text messages, photos and videos between team members.

Rules engine based on the actions assigned to each role. Below are examples of the rules configured related to a given role which can be changed or modified by individual hospitals based on their needs:

HTO can only activate the RRT in response to call on the RRT activation number. HTO will only enter the location provided and activate the RRS. HTO will not receive any checklist.

PCT can only activate RRT but will receive all communications from other members. The PCT can only enter or update patient vital signs.

PCN can activate RRT, enter/modify patient vital signs and can also fill in assigned checklists. The PCN receives all communications and checklists from other members. The PCN can only update its own checklist but cannot update checklists received from other members.

PCL can activate RRT, update vital signs and can also fill in assigned checklists. The PCL receives all communications and checklists from other members. The PCL can update checklists received from PCN but cannot update checklists received from other members.

CHN can activate RRT and can also fill in assigned checklists. The CHN receives all communications and checklists from other members. The CHN can update checklists received from PCN but cannot update checklists received from other members.

CCN can activate RRT, enter/modify vital signs and fill in assigned checklists. Receives checklist from other members. Can update assigned checklist and checklist received from PCN but cannot update checklist received from AOD, APRN or MD. The CCN is the only one to close the RRS event.

RT can activate the RRT, enter/update patient vital signs will receive communication from all members but cannot update any checklist.

LT cannot activate RRS, will be alerted when RRS is activated and will receive the required Labs checklist. Cannot update any checklist.

PHARM cannot activate RRT, will be alerted when RRT is activated and will receive all assigned checklists. Will receive a list of medications that are derived from the Recommendation and Intervention Checklist. Cannot update any checklist.

ARPN can activate RRT, receives all checklists and can update checklist received from PCN, and CCN. Can update Intervention and Test checklist only for Interventions and Tests that the APRN is authorized.

MD can activate RRT, receives all checklists and can update all checklist received from others. MD is the only member authorized to check/uncheck any Intervention and test on the checklist.

Determine arrival time of team members at patient location. This can be done in one of two ways. The first method utilizes Bluetooth beacons placed in the patient room. When the RRS is activated the smartphone of the RRS member activating the RRS captures the beacon ID of the beacon in the patient room and sends it to the backend. The smartphone of the team members that have received the RRS notifications also start monitoring the beacons and sending the beacon ID to the backend. When the team member arrives at the patient room, it sends the beacon ID to the backend which now knows that the team member has arrived at the patient room and hence determines how long it took the member to arrive.

In situations where Bluetooth beacons are not deployed an alternate method can be used to determine arrival times. The smartphone App of the team member who has activated the RRS, starts to transmit the Bluetooth beacon with a unique identifier assigned by the backend. All the members phones that have received RRS notifications start to monitor the Bluetooth beacons looking for that unique identifier. Once the member reaches close to the RRS activating member it will receive the unique identifier and inform the backend that it has found the unique identifier. The backend now knows that the member has arrived at the patient location and can calculate the time taken to arrive at the patient location.

If the hospital has deployed the RTLS, the backend can track the staff members and use the location information to predict how long it will take the member to arrive at the patient location. The RRS Admin dashboard can display each team member's location and Expected Time of Arrival at the event location in real time. Team members can also receive information on the location of other team members.

RRS Smartphone Application Implementation:

The screens shown in this section are from an actual implementation of the RRS developed for demonstration to a hospital.

Checklists for only two suspected causes: Cardiac and Respiratory are shown. Checklists for other suspected causes have the same look and feel however the content is different.

Figure 1B:
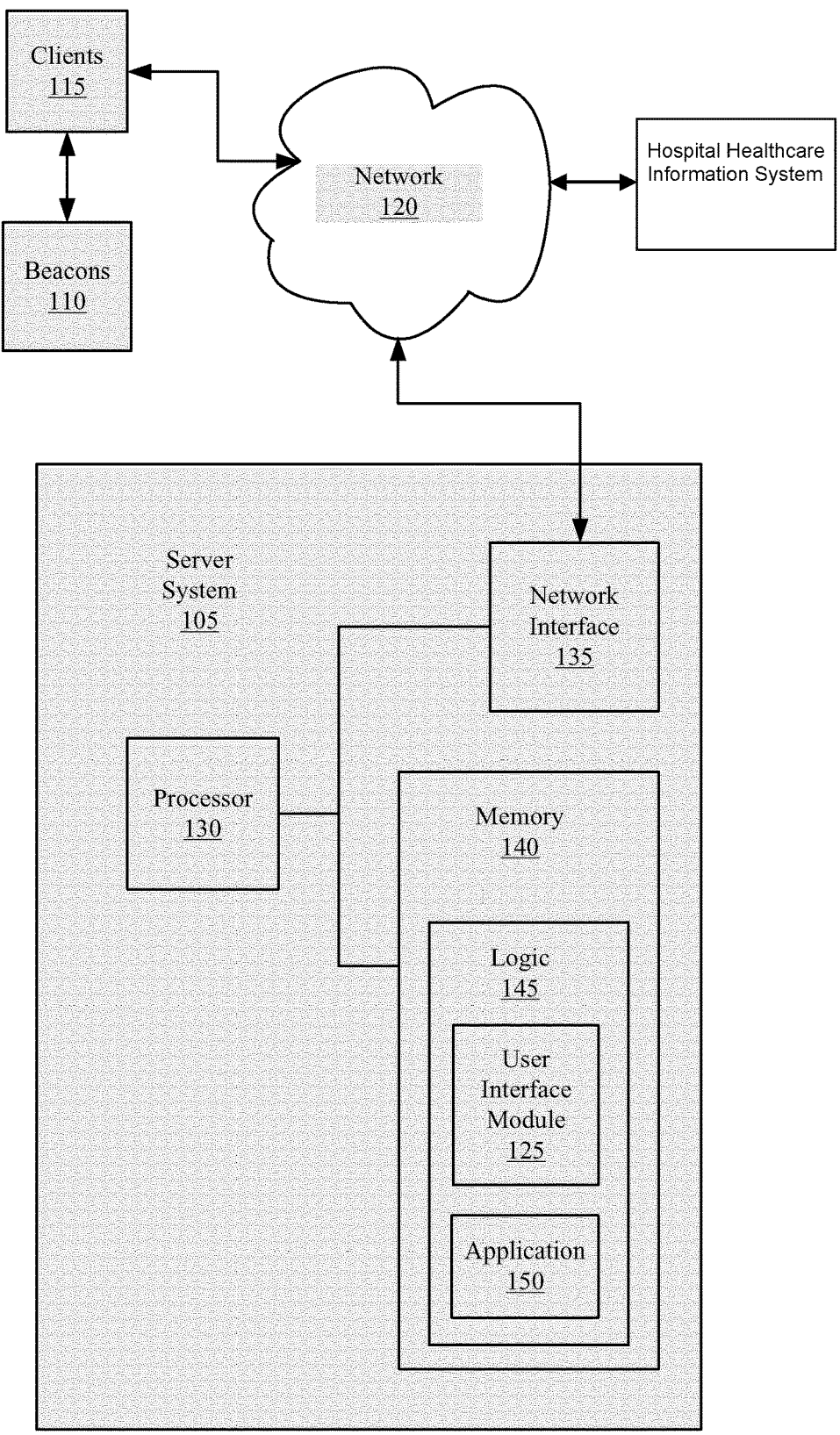
FIG. 1B is an exemplary system that can be used to practice aspects of the present technology.

FIG. 1B illustrates an exemplary architecture for practicing aspects of the present technology. The architecture comprises a server system, hereinafter "system 105" that is configured to provide various functionalities, a number of client devices, hereinafter "client 115" and a number of beacon devices, hereinafter "beacon 110" which are described in greater detail throughout this document. Generally, the system 105 is configured to communicate with client devices, such as client 115. The beacon devices such as beacon 110 may not communicate directly with the system 105 but communicate with the client 115 to relay their information to the system 105.

The system 105 may communicatively couple with the client 115 via a public or private network, such as network 120 which connects with client 115 wirelessly using wireless technologies such as IEEE 802.11 and 2G, 3G, 4G and 5G public cellular networks. The network 120 connect with system 105 using wired and wireless technologies such as Ethernet, IEEE 802.11 and 2G, 3G, 4G and 5G, via the network interface 135.

The system 105 generally comprises a processor, 130, a network interface 135, and a memory 140. According to some embodiments, the memory 140 comprises logic (e.g., instructions) 145 that can be executed by the processor 130 to perform various methods. For example, the logic may include a user interface module 125 as well as a data aggregation and correlation application (hereinafter application 150) that is configured to provide the functionalities described in greater detail herein. The logic 145 also implements the rules assigned to the various user roles defined Each of the client 115 can assume any user role when the users logs into system 105 which maintains a database in memory 140 of users along with their assigned roles and rules associated with that particular role.

It will be understood that the functionalities described herein, which are attributed to the system 105 and application 150, may also be executed within the client 115. That is, the client 115 may be programmed to execute the functionalities described herein. In other instances, the system 105 and client 115 may cooperate to provide the functionalities described herein, such that the client 115 is provided with a client-side application that interacts with the system 105 such that the system 105 and client 115 operate in a client/server relationship. Complex computational features may be executed by the system 105, while simple operations that require fewer computational resources may be executed by the client 115, such as data gathering and data display.

In general, the user interface module 125 is executed by the system 105 to provide each of the client 115 real time data updates relating to the patient's conditions and the actions taken by client 115. As a client 115 updates an item relating to the patient's condition, the interface module 125, receives this update from that client 115, updates the database in memory 140 and communicates this update to all connected client 115. This way all client 115 are synched to show the same information in real time. The application 150 provides a dashboard in the form of a graphical user interface (GUI) used by administrator of system 105 to configure the database in memory 140, such as adding and deleting users, updating various checklist items, creating/configuring new rules, detailed reports of past events, etc.

FIGS. 1C-37 are exemplary views of interactive graphical user interfaces.

Figure 1C:

FIG. 1C shows the start-up screen and displays the Hospital Logo and Name. The screen appears if the program had been closed previously and the user launches the program by tapping the program icon or by tapping the notification of an RRS event. This screen is only visible for a short time and is replaced by the next screen.

Figure 2:
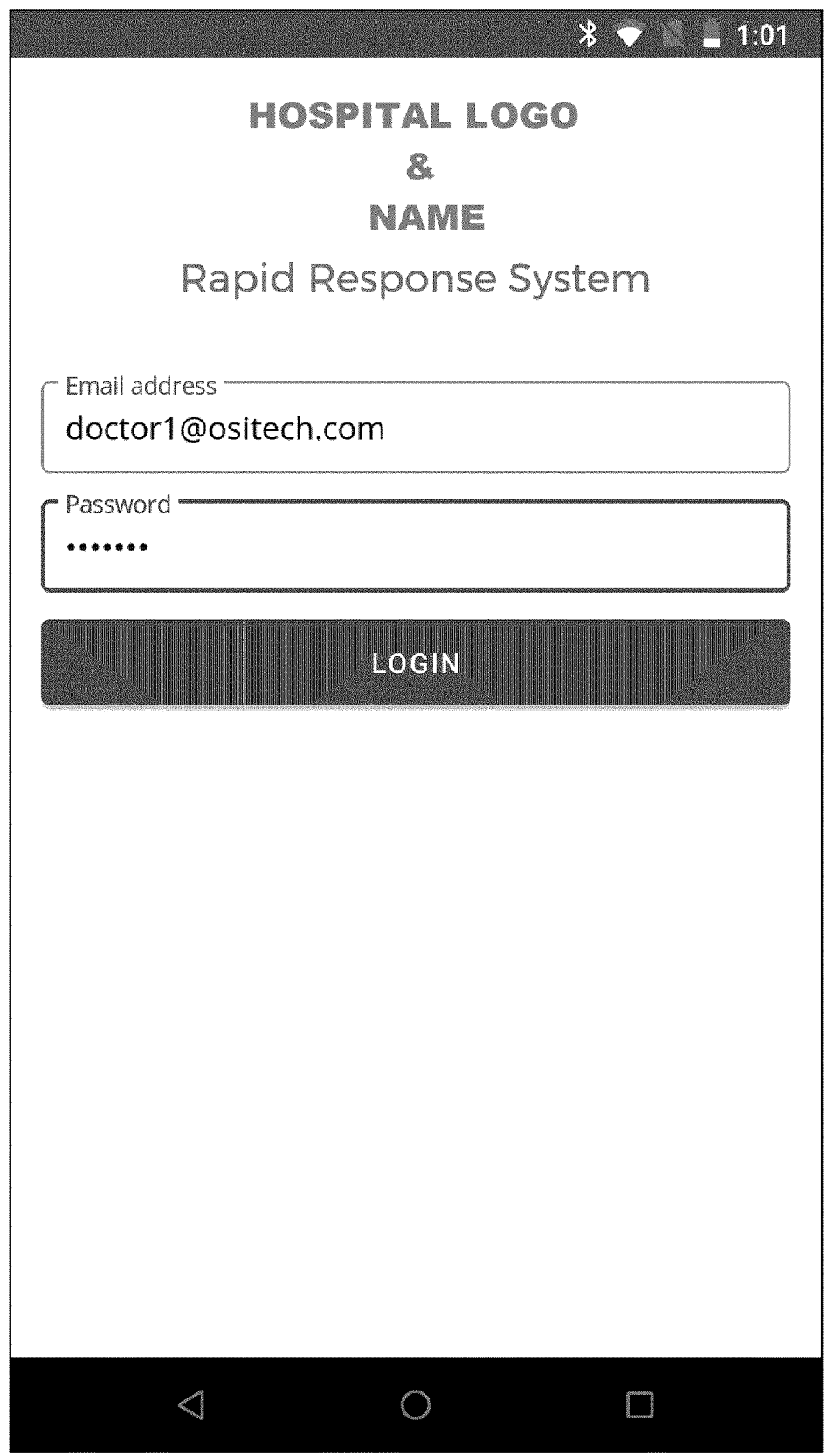

FIG. 2 shows the user login screen and is only shown after the first screen if the user was not logged in. The username and password are validated by the RRS Host system which maintains a database of authorized users. The database contains such attributes as designation, role in the RRS team, type of information that the user will receive, type of information user can create/modify, type of actions the user can initiate, etc. Standard password recovery methods are provided.

Figure 3:
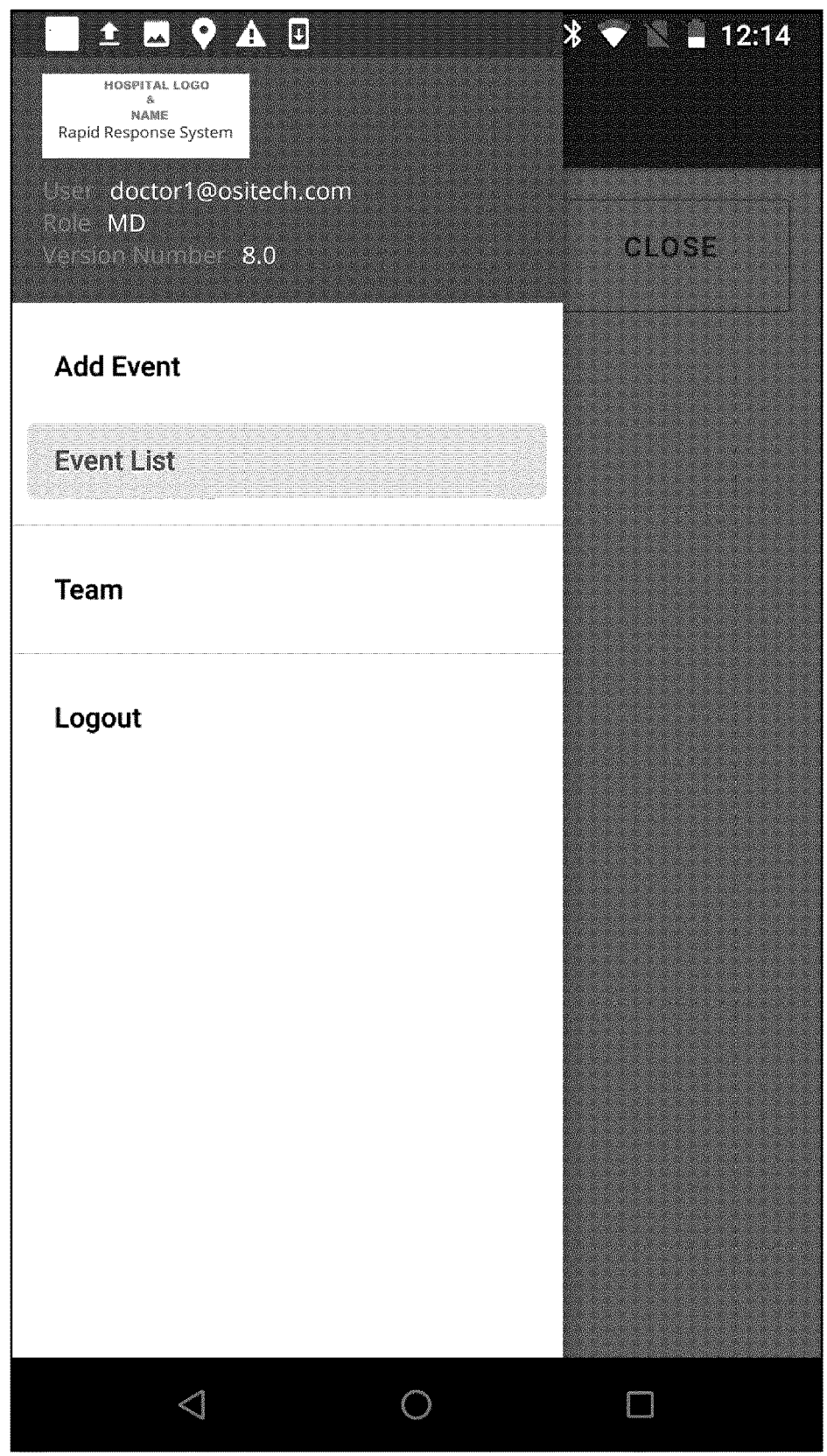

FIG. 3 shows the application setting screen which is displayed after the user has logged in. The user ID, role and the Software version number is displayed. The user can select an item from this screen. Currently only four items are shown. By tapping an item on this screen will take the user to the screen related with that item.

Figure 4:
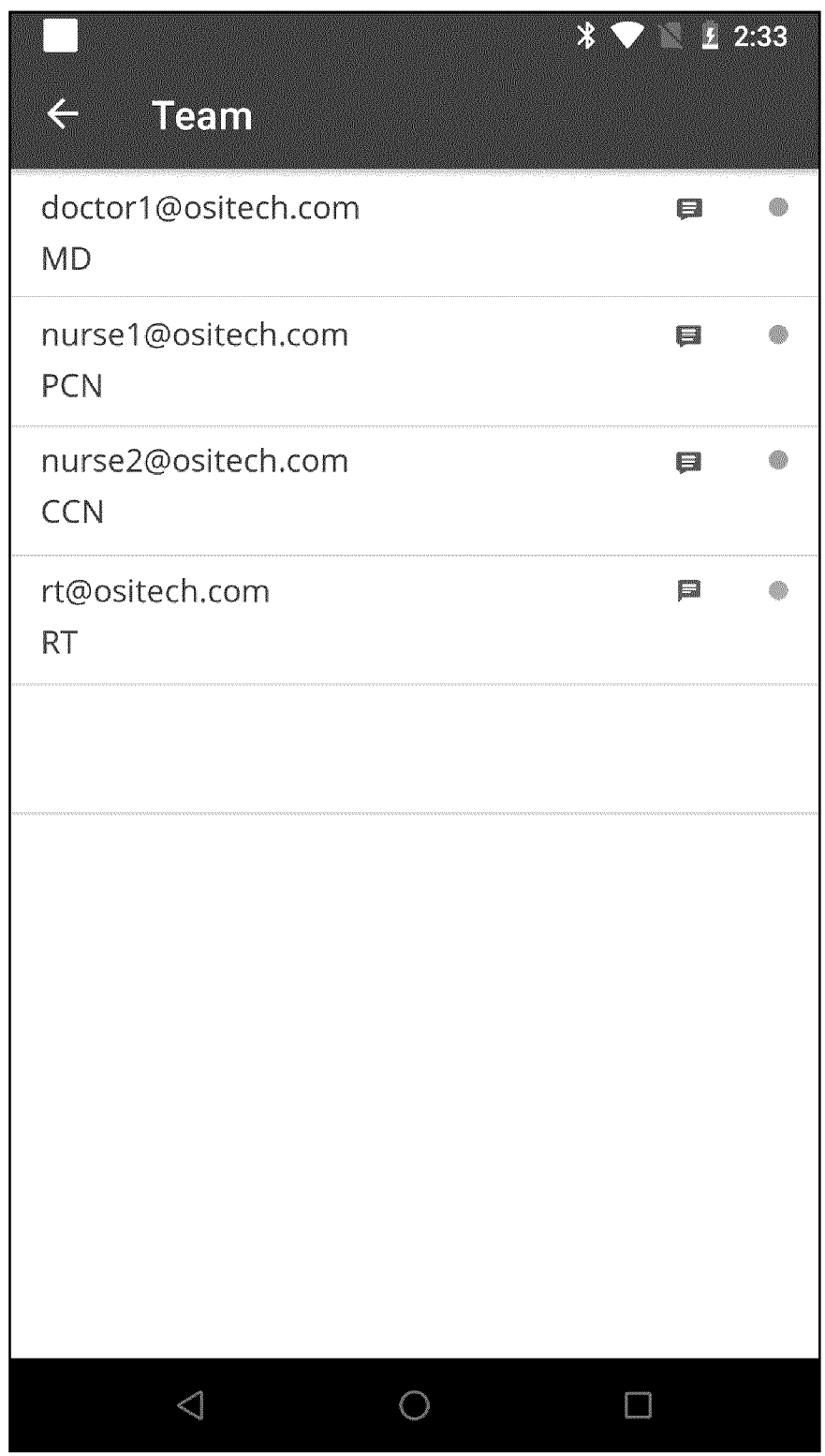

FIG. 4 shows the current status of each of the team member and their role which is indicated below the user ID. The round dot if green indicates the team member is logged in and available. The grey dot indicates the member is not logged in. The chat icon left of the status dot is used to communicate with the team member via text messages. This private chat message feature does not use any of the social media chat programs. This enables patient related information to stay private and is not mixed with the users' personal chat programs. The icon is blue if the user is available for chat messages. If grey the user cannot be sent messages. The RRS backend systems maintains information on all team members such as their available times, roles, position, etc. and is managed by the system administrator.

Figure 5:
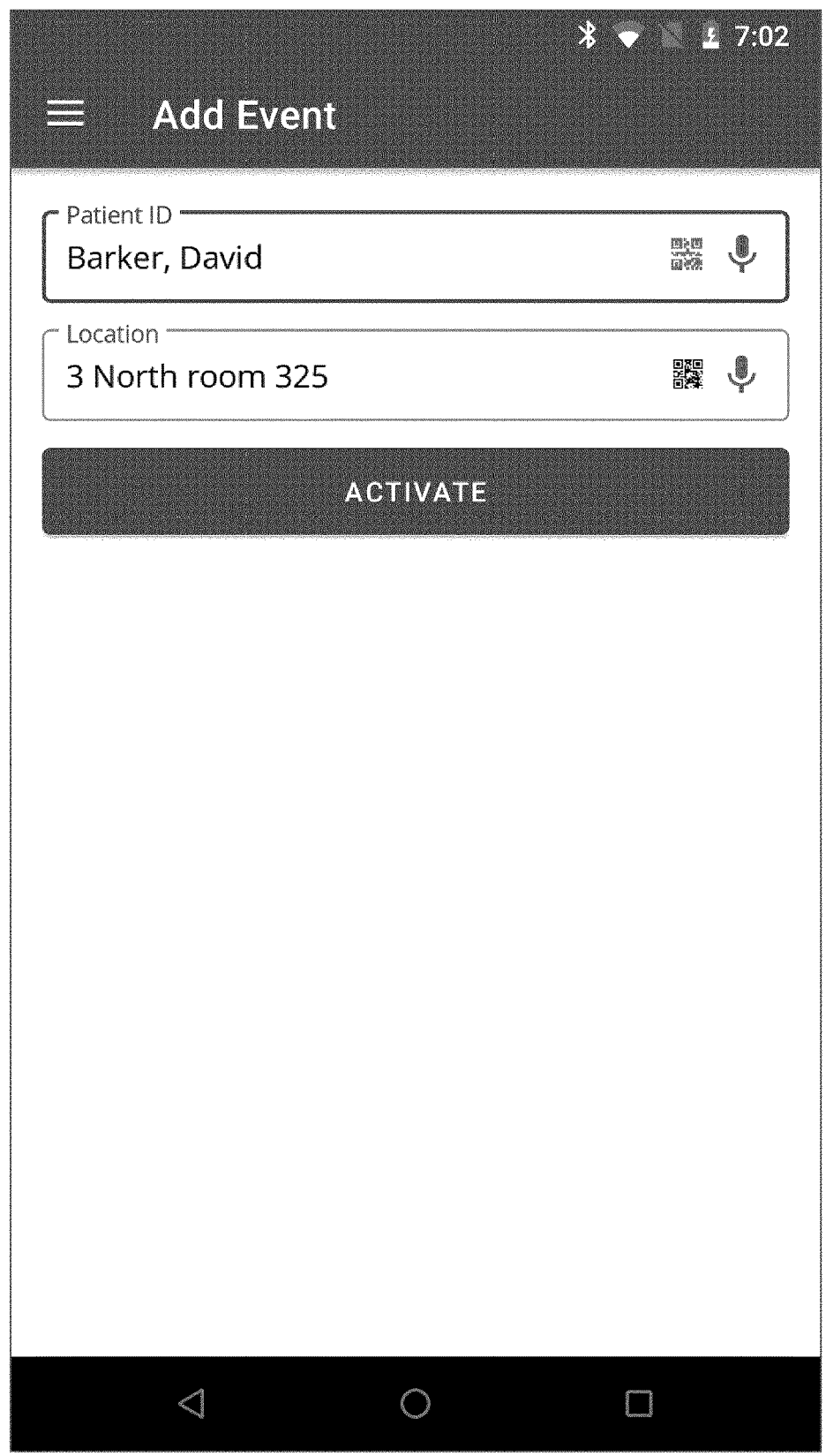

FIG. 5 shows a RRS activation screen. This screen is presented when an authorized team member taps the "Add Event" on the Status page to activate the RRS team due to deteriorating condition of the patient. The member can enter the Patient information using the keyboard, taping the mic icon and speaking the patient's name which is then converted to text. The Patient ID can also be entered automatically by tapping the QR code icon on the right. The patient wristband that usually has the Patient ID coded as a QR code will then be read by the program and shown in this field. Only the information such as the patient name will be displayed in this field. The patient's location is entered either manually or tapping the mic icon speaking the location which is translated into text and appears in this area or by scanning a local visual code, such as a barcode or the QR code. By tapping the activate area, the user is asked to confirm activation of the RRS team. If yes, all the team members are sent notification which indicates patient's ID and the location. The RRS event cannot be activated if any of the two areas is empty. The user is alerted to this by showing an alert icon (! within a red circle).

Figure 6:
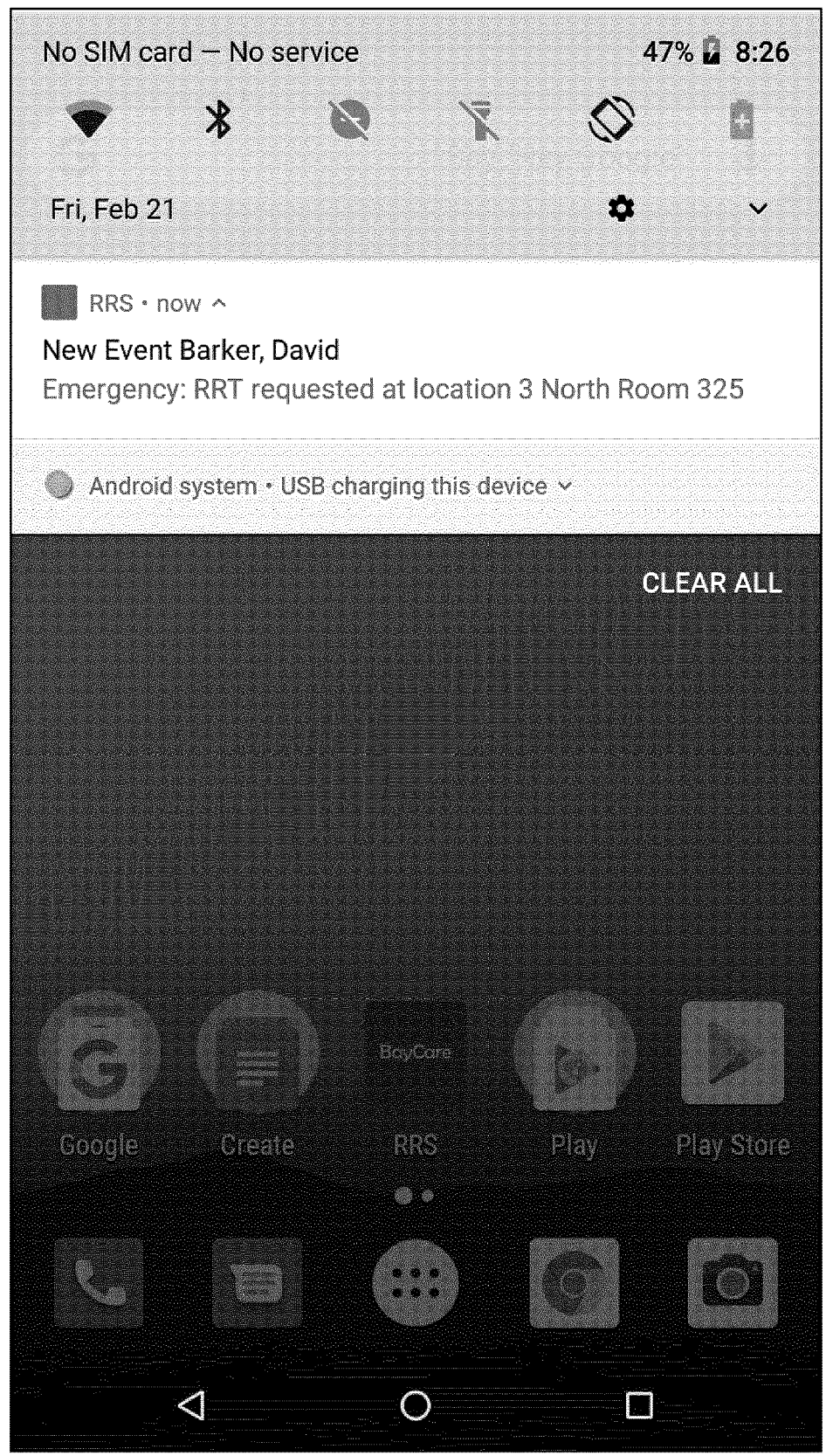

FIG. 6 shows a typical notification message received by all the team members. The actual implementation varies between various phones. However, in all cases the phone can be set by user to play an audible indication when the notification arrives. If the user was logged in but had closed the application, an audible is played and by swiping down from top the above notification appears. By tapping the red RRS area, the RRS application is launched. The phone can be set to remind the user of the notification periodically.

Figure 7:
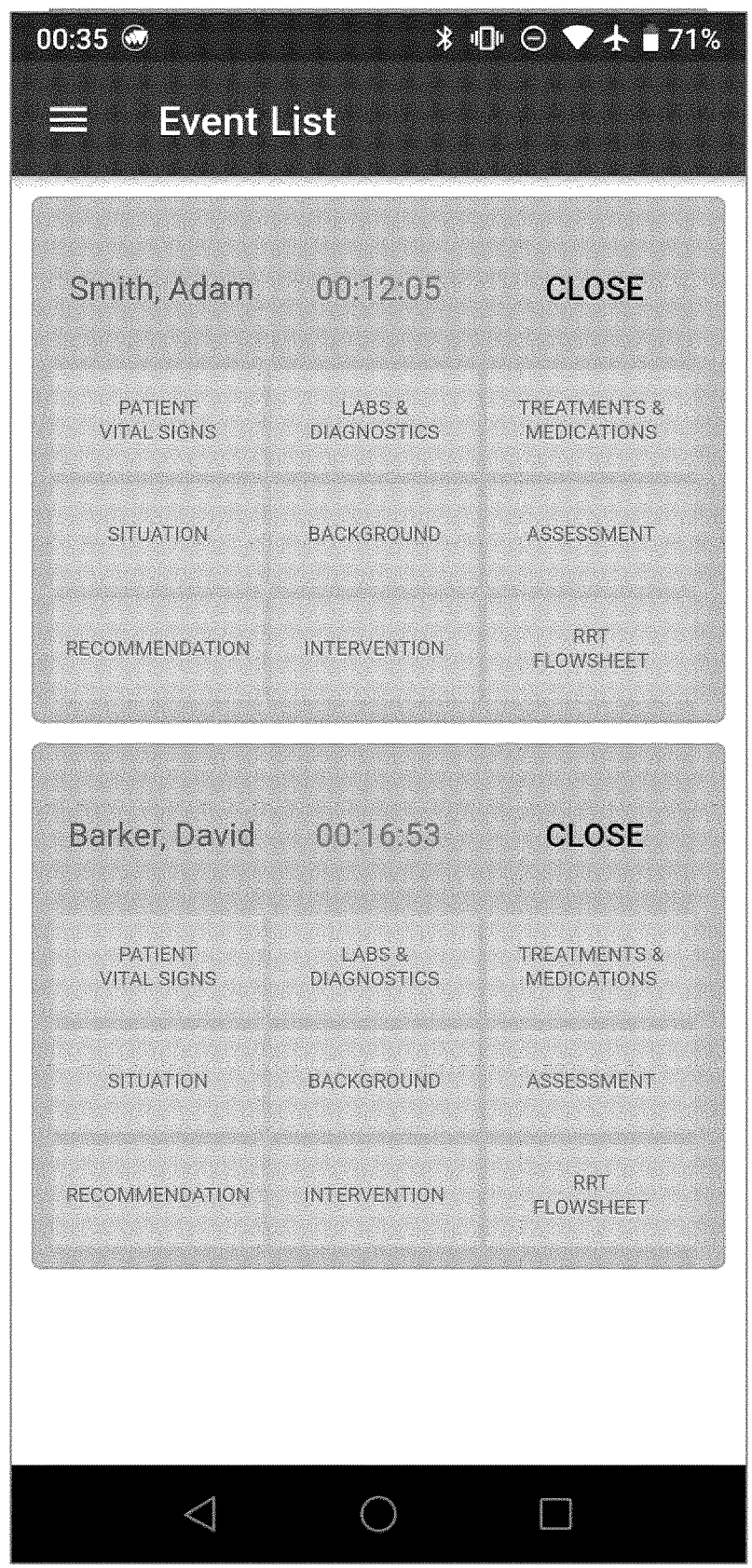

FIG. 7 shows a screen when the "Event List" is tapped on the Status page. This screen shows one or more RRS events that are currently active. While unlikely, the system allows for multiple RRS events. For each RRS Event, the Patient Name is shown, then the Event Timer and the word "CLOSE". The timer counts in minutes and seconds and is started once the RRS is activated and is shown on all member's screen indicating the time elapsed since the activation of the RRS event. When the event is closed, the timer value is recorded for Quality purposes. Also, as each team member arrives at the location, their arrival time is automatically sensed and recorded by the RRS system to be used for later review by QA for improving team performance. Below the Patient name are nine boxes: Patient Vital Signs, Labs & Diagnostics, Treatments & Medications, Situation, Background, Assessment, Recommendation, Intervention and RRT Flowsheet. At the start of the RRS Event these boxes are grey and tapping them have no effect. As each checklist is completed, the corresponding box turns green. Tapping a Green box shows only the items that were check in that checklist. For example the Situation checklist has several boxes that can be checked by a team member. Tapping the green box labelled Situation will only display the checked item from the checklist. This enables Team members not directly involved to view a summary of the checklist once it is completed.

Once the MD has approved the Recommendations and Interventions, the boxes labelled Labs & Diagnostics and Treatments & Medications turn green. These are now orders that can be executed. Thus the Lab Technician can view the labs and diagnostics that have been ordered and the Pharmacist can view the medications that are required. FIGS. 33-37 provide details on when these boxes are tapped.

Figure 8:
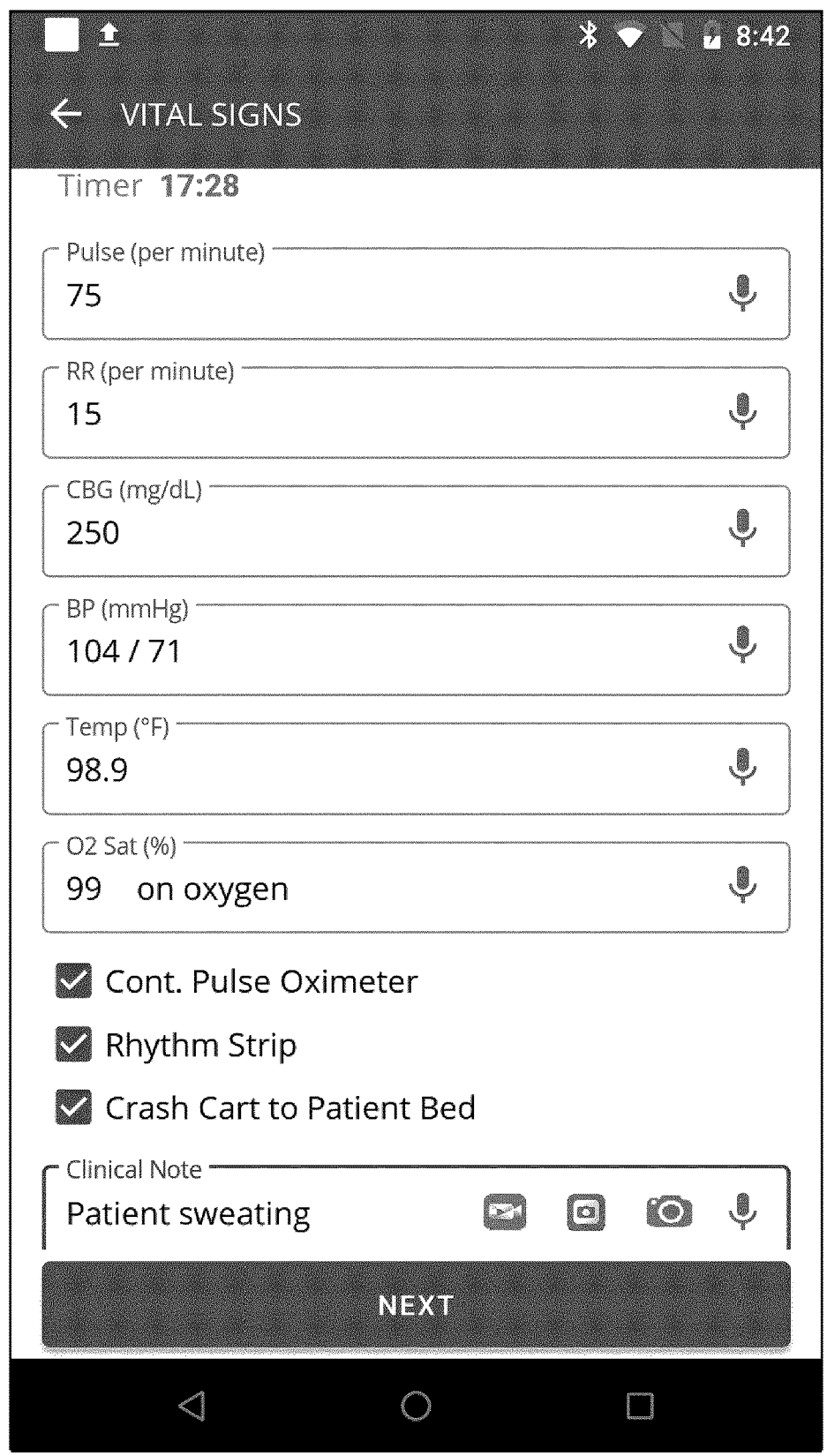

The final step related to the RRS even is for the CCN to file the RRS Report. In some hospitals this is called RRT Flowsheet. The CCN can dictate or enter any comments and submits the RRT Flow sheet which turns the RRT Flowsheet box green. Tapping it displays a complete history of the RRS event from the beginning and includes all checklists, with time stamps as well as arrival time of team members. The CCN now taps close which files the RRT Flow sheet and closes the RRS Event. A pop-up message appears on all team member screen that the event has been closed together with the member's ID who closed the event. A notification is also sent to all members involved in the RRS that the RRS event is now closed FIG. 8 shows a screen that is presented to all members once the RRS has been activated. Authorized members can enter or modify the information. This screen is scrollable. The Patient ID and Location (not visible here) is at the top of the screen. The Timer shows the elapsed time since the activation. Vital signs can be entered manually or entered by tapping the mic icon and speaking. The spoken words are converted to text. Information immediately appears on all members' screens. Clinical Note area is used to enter any additional information that can be useful to RRS team. As above, information can be entered manually or by speaking using the mic icon. By tapping the camera icon, the phone camera is used to take photograph or video such as of the equipment screen monitoring the patient status. The red camera icon indicates that a picture is available and can be viewed by tapping. A video clip can also be taken and viewed by any member by tapping the red video icon. Only authorized members can view the pictures or video.

Figure 8A:
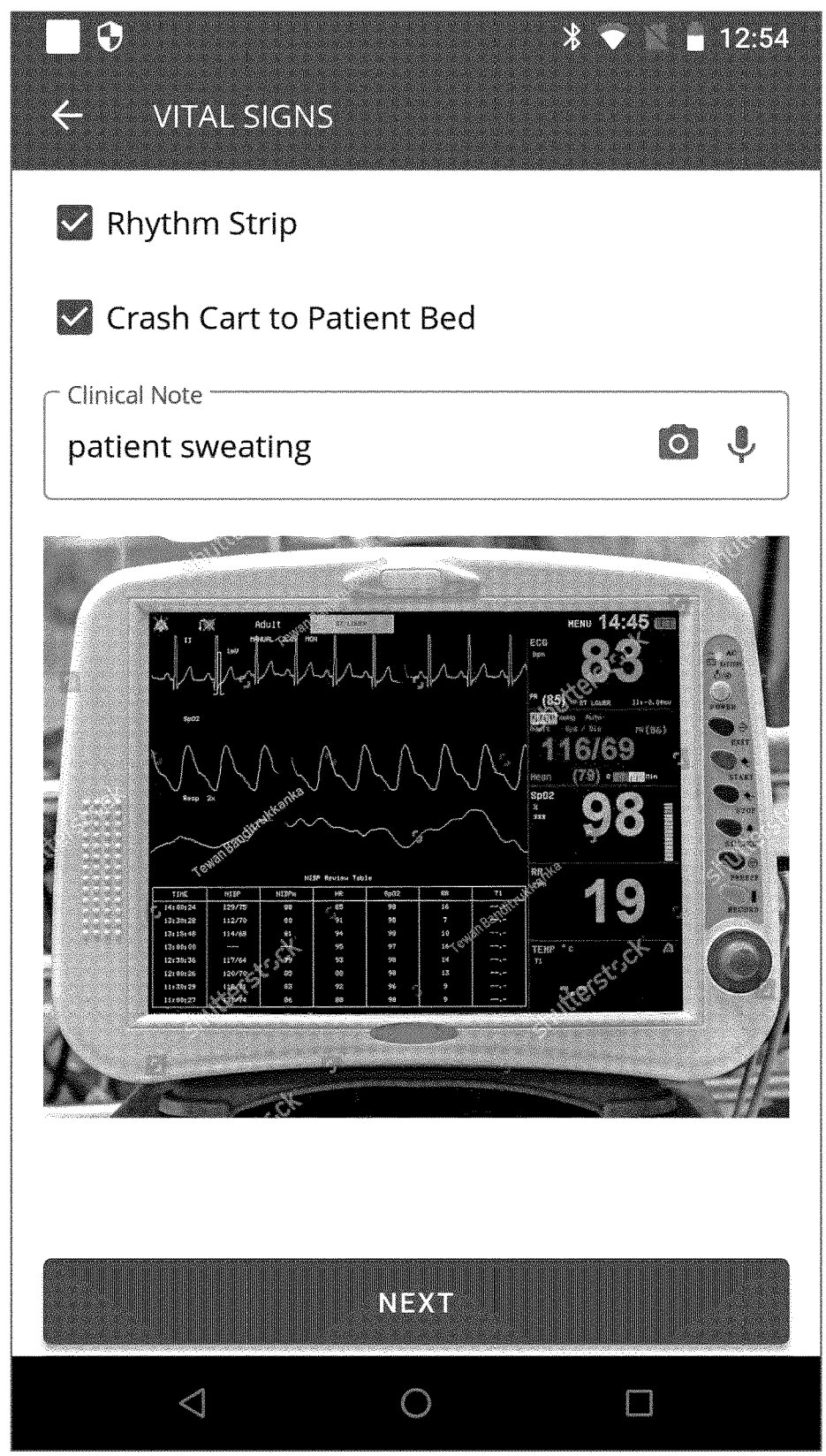

FIG. 8A shows a picture taken by a member of the equipment showing the vital signs that can be shared between all members instantly. Any member can tap the red picture icon to see one or more related photos. Similarly, a short video clip can also be shared and viewed by authorized team members.

Figure 9:
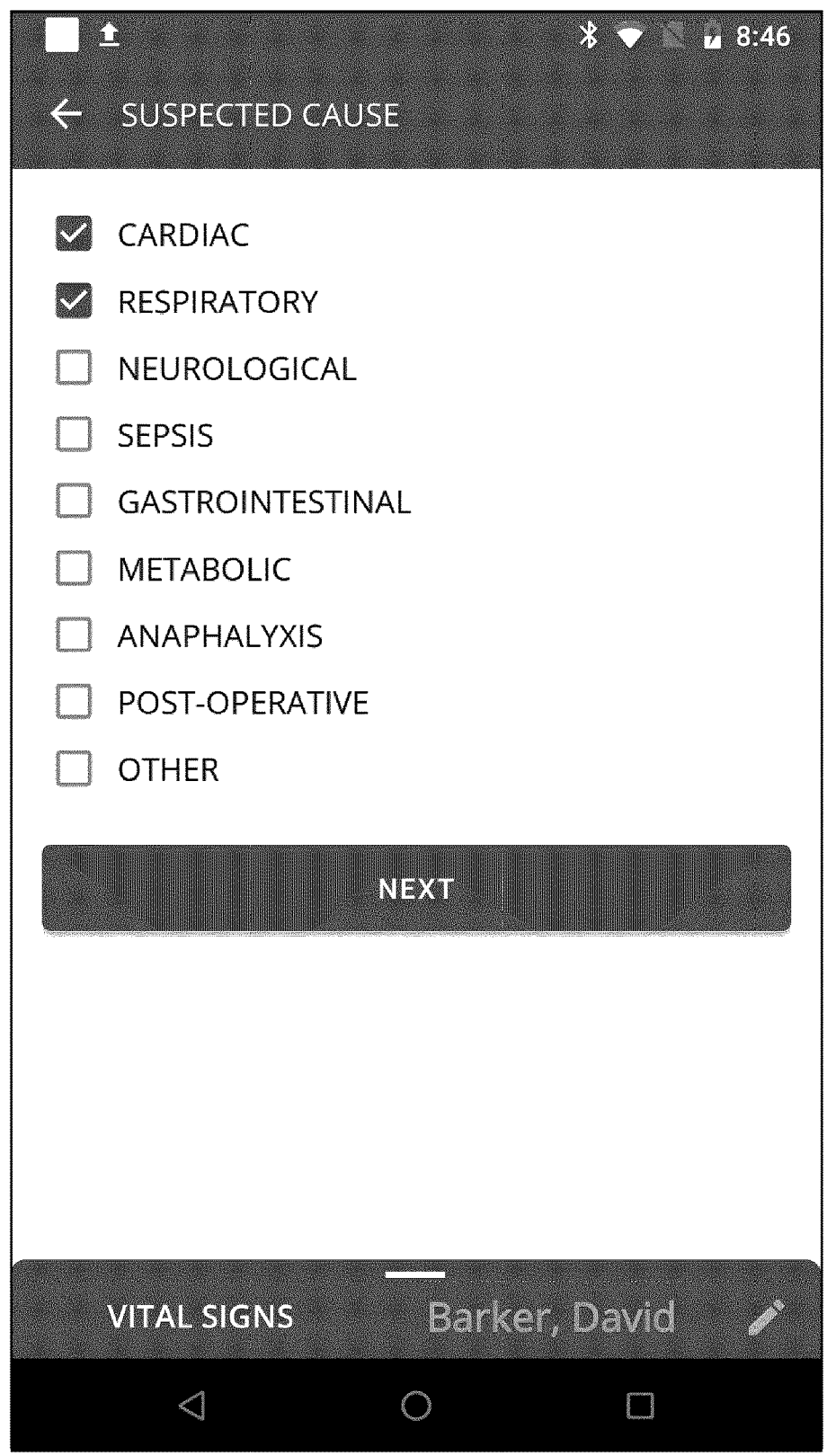

FIG. 9 shows a screen that is presented once patient vital signs have been entered. Typically, either the Primary Care Nurse (PCN) or the Critical Care Nurse (CCN) who has arrived would determine the suspected cause. More than one suspected cause can be checked. This information is instantly available to all team members who are authorized to view this information. Every team member can view the patient's vital signs by swiping upwards from the "_" symbol, on any of the following screens. By tapping the "pen" icon, authorized team members can update the patient's vital signs. The Backend system keeps track of changes made, time and who made the change for auditing purposes.

Figure 10:
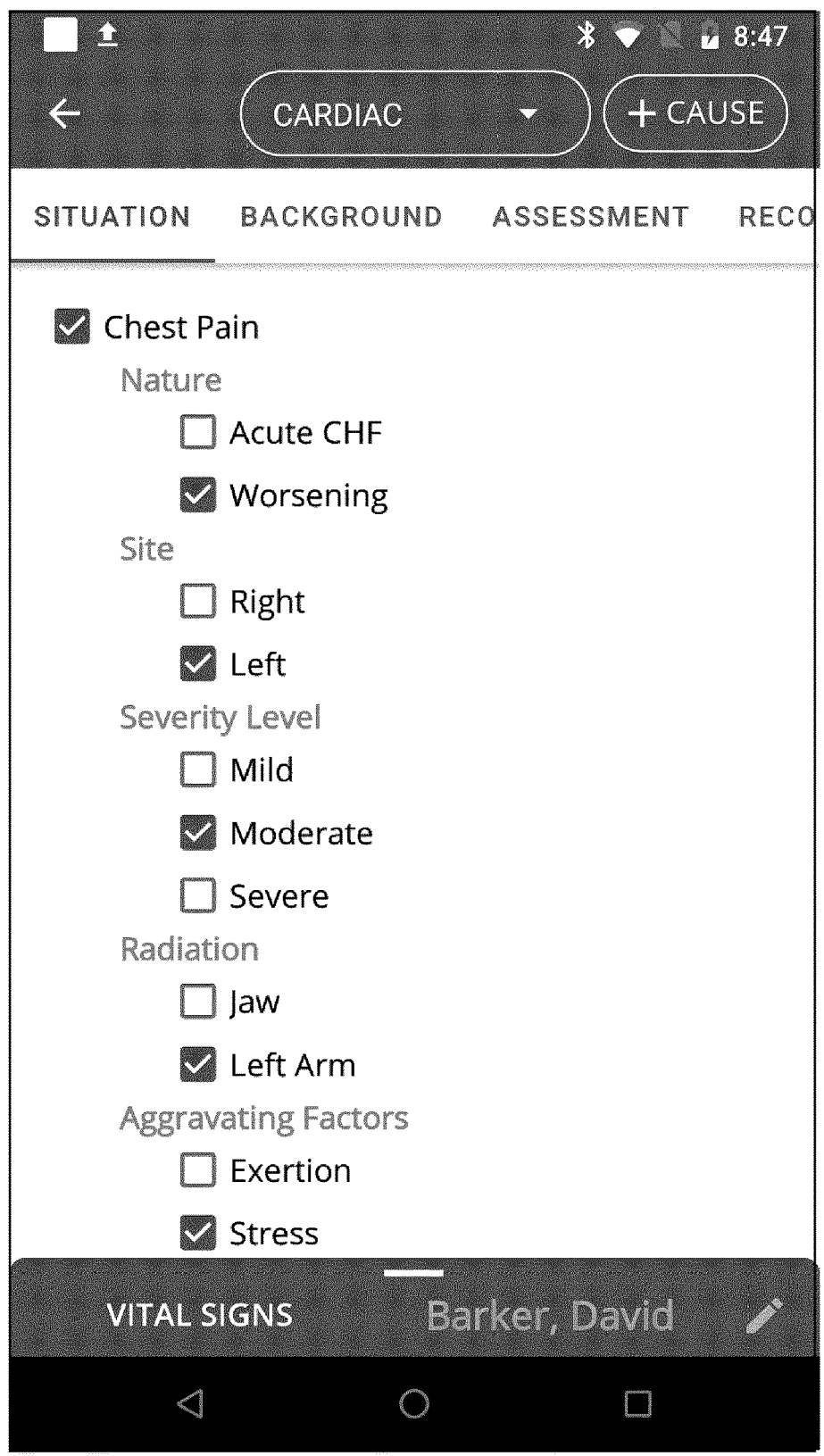

FIG. 10 is screenshot of a cardiac situation. Each suspected cause has five checklists: Situation, Background, Assessment, Recommendation and Intervention. Each checklist has boxes that can be checked and arranged in a logical fashion. As each box is checked it is instantly shown as checked on all team member's screens, thus each member is instantly aware of the patient condition. Any authorized member can update the checklist. Backend keeps a record of all changes and who made the changes for audit purposes. By tapping the down arrow on the Cardiac Box, the user can select another suspected cause if it had been added. To add a suspected cause, tap the +CAUSE button. The screen showing suspected causes is shown The SITUATION screen indicates the current situation of the patient.

Figure 11:
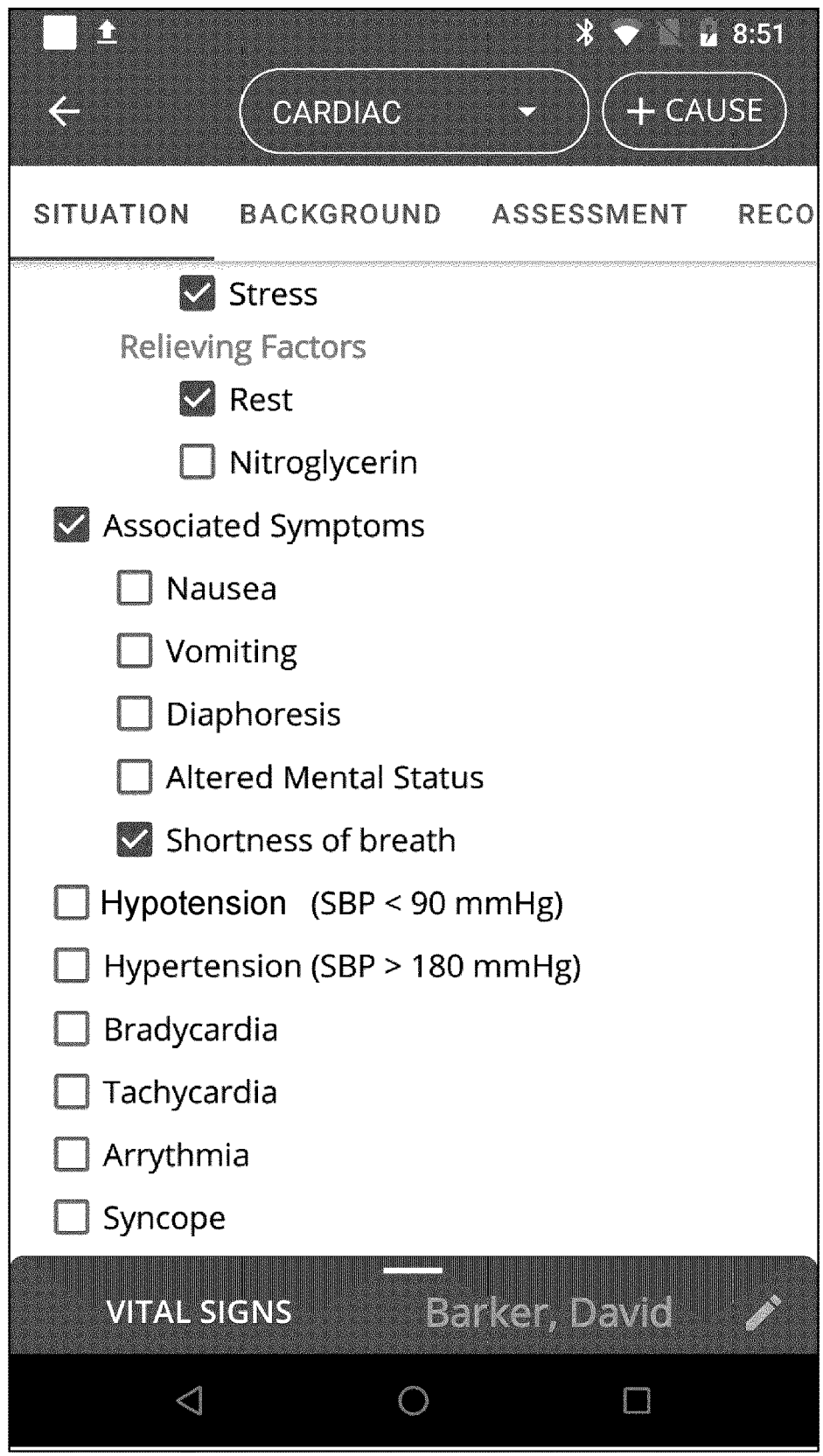

FIG. 11 shows a continuation of the cardiac situation checklist from above.

Figure 12:
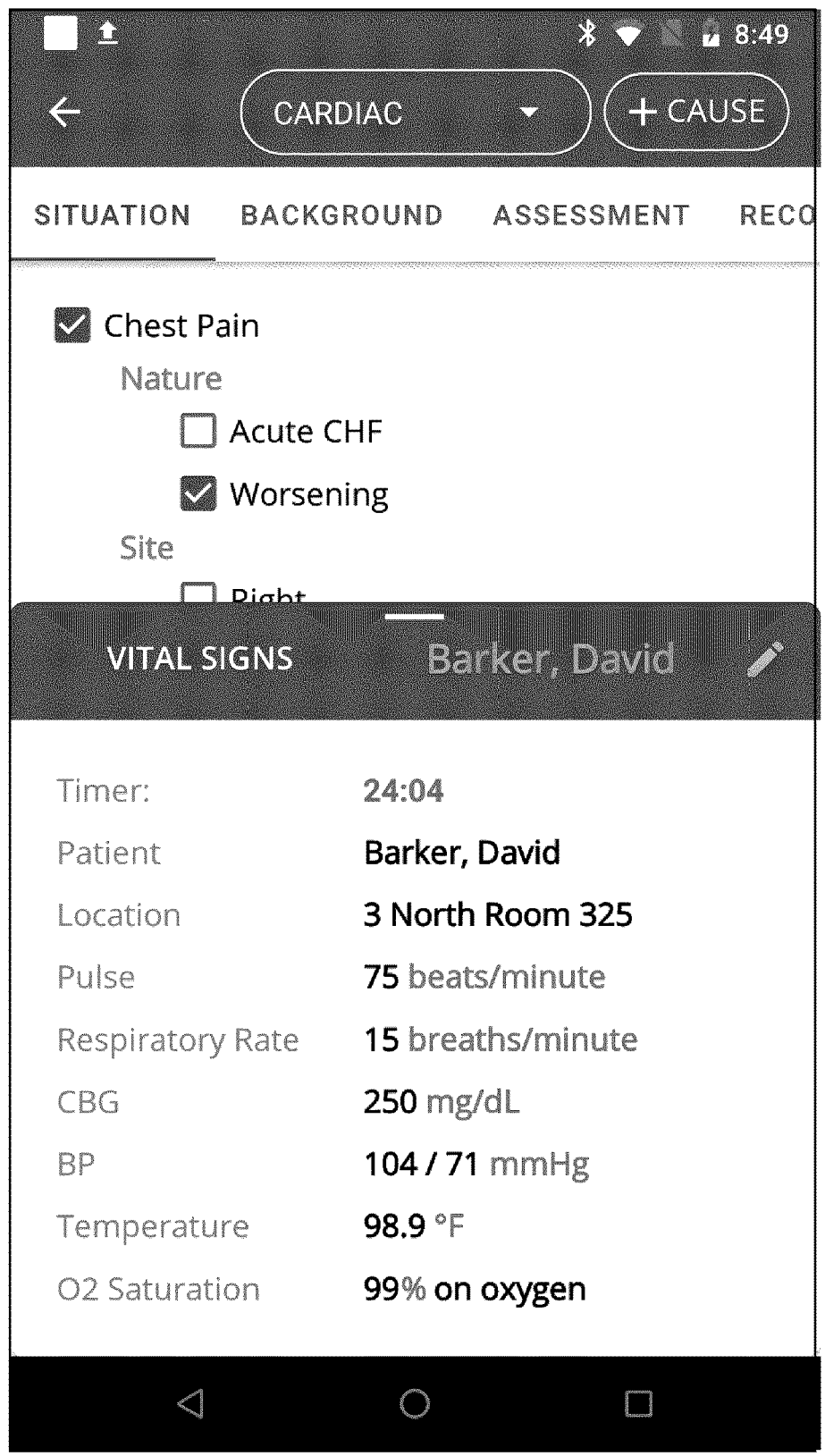

FIG. 12 shows a vital signs summary screenshot. From any of the Situation, Background, Assessment, Recommendation and Intervention Screens, any team member can instantly view the patient's vital signs summary by swiping up from the "_" symbol. Authorized members can also update any of the vital signs by tapping the "pen" icon on the right of the patient's ID. The Vital Sign Screen is presented. The time of change and person making the change is recorded by the RRS backend computer system for future audits. An up arrow or down arrow next to the vital sign is shown if the reading has changed by a certain amount over a given time period. The range of change and time is programmable at the backend. This can alert team members if one or more of the vital signs is deteriorating rapidly.

Figure 13:
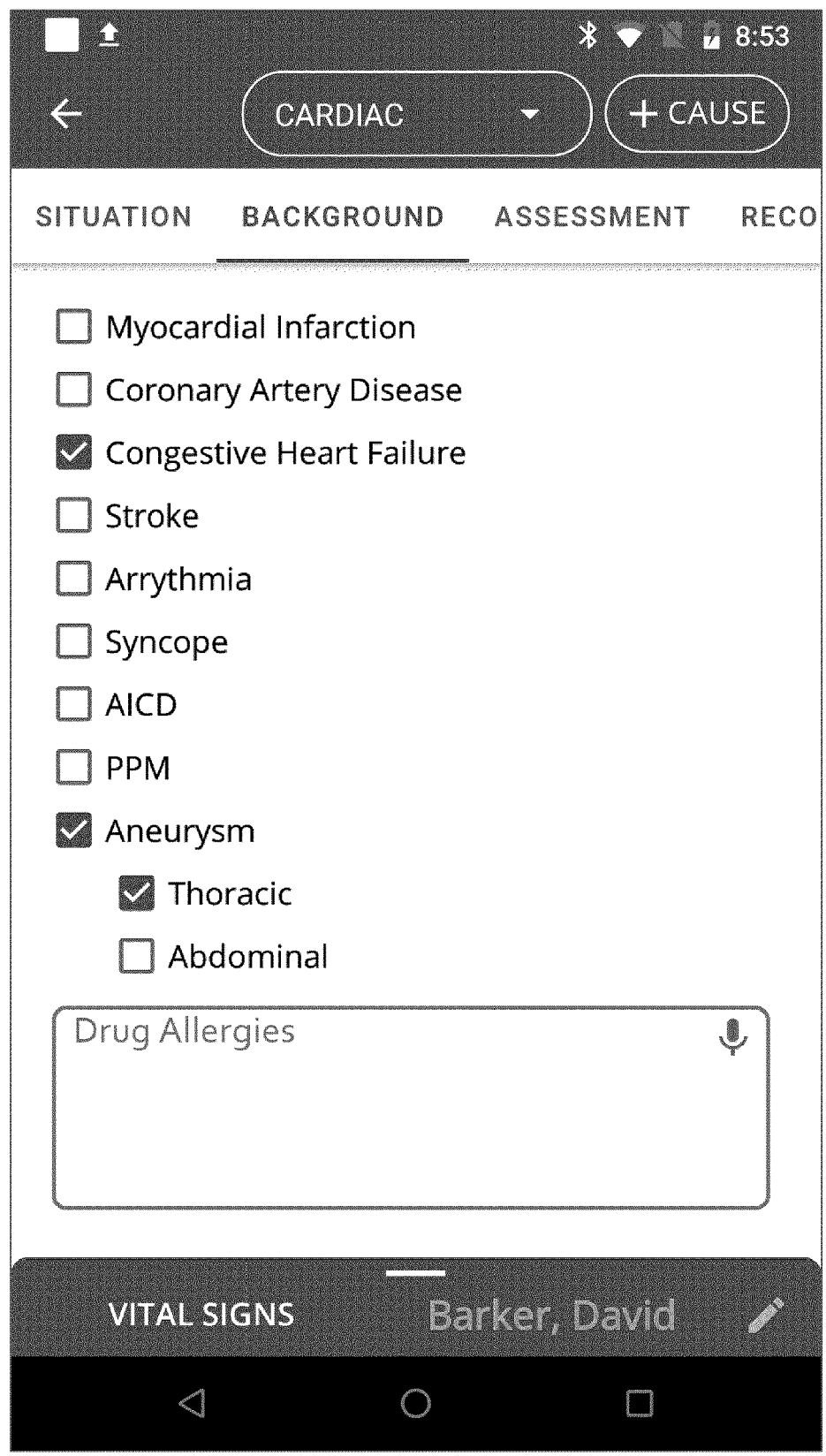

FIG. 13 shows a cardiac background screenshot. This screen summarizes the Patient's Background if the suspected cause is Cardiac. It is intended to give team members, especially the physician information on patient's prior cardiovascular history.

Figure 14:
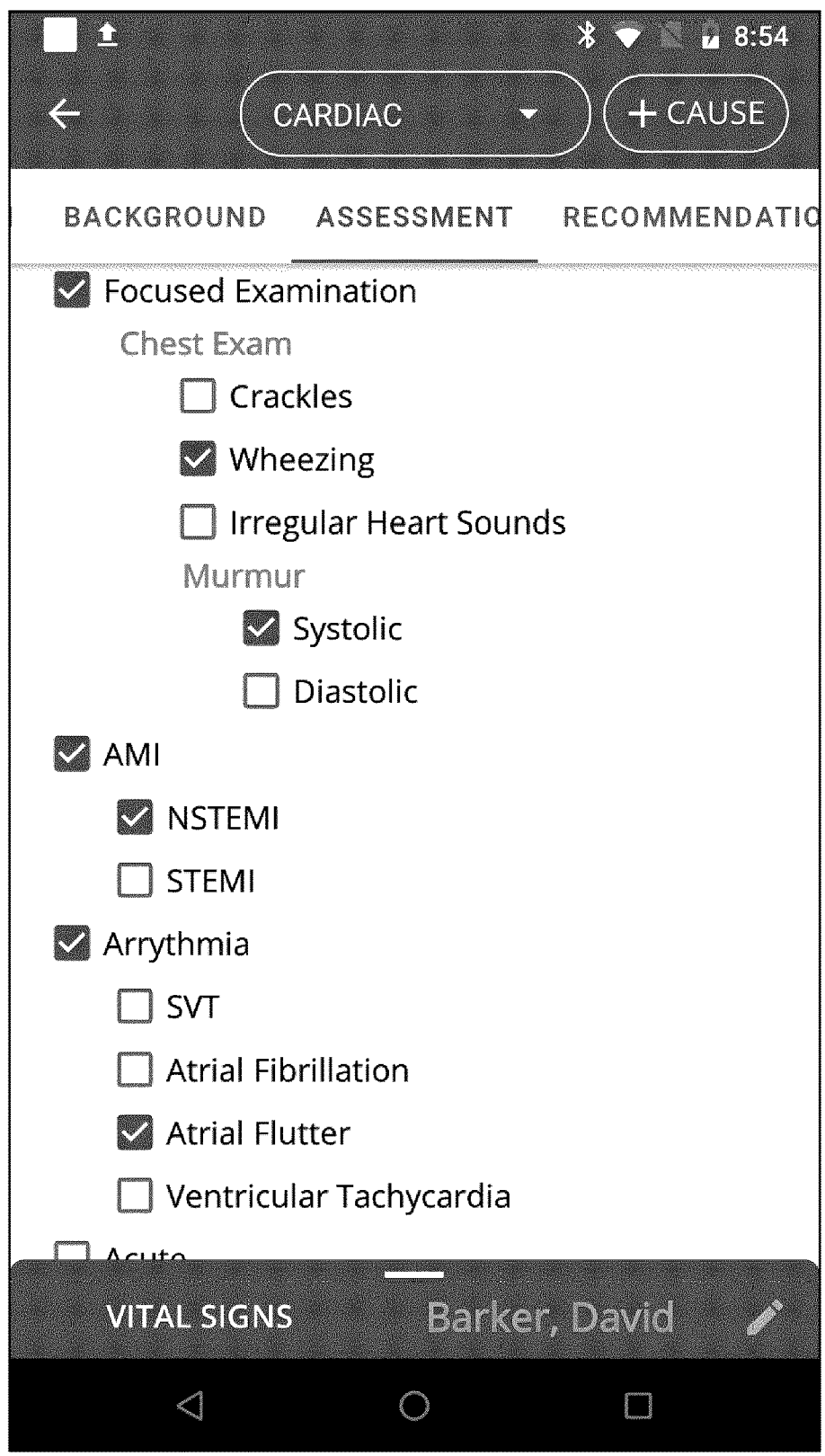

FIG. 14 shows a cardiac assessment screenshot. This screen is typically used by the Critical Care Nurse who has training to assess the patient and provide recommendation. The Assessment screen is immediately accessible by all team members; however, only authorized team members can update it. Typically, this would be the Critical Care Nurse. This is the first of the two cardiac assessment screens.

Figure 15:
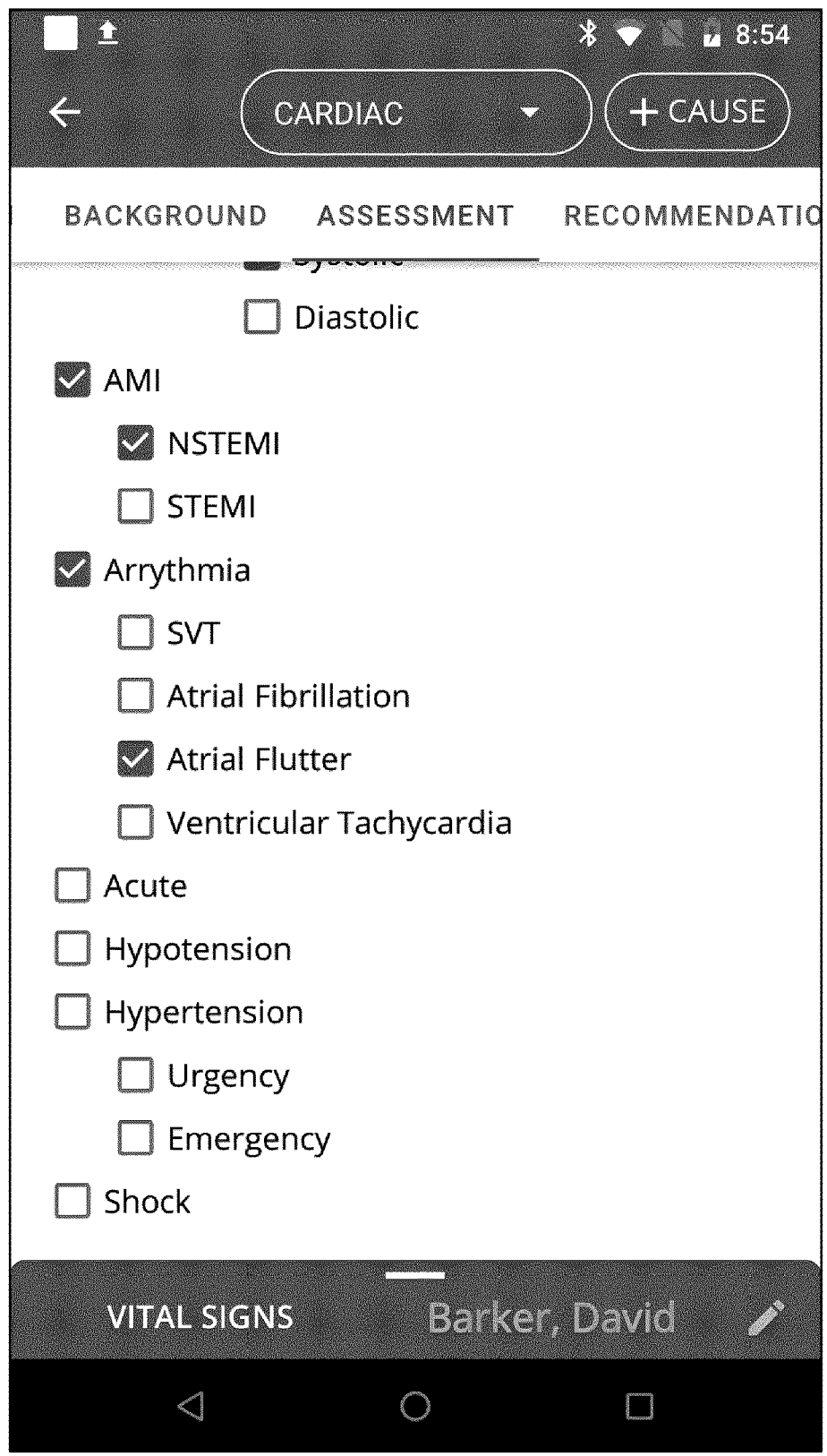

FIG. 15 shows a second cardiac assessment screenshot. This is a continuation of the cardiac assessment checklist.

Figure 16:
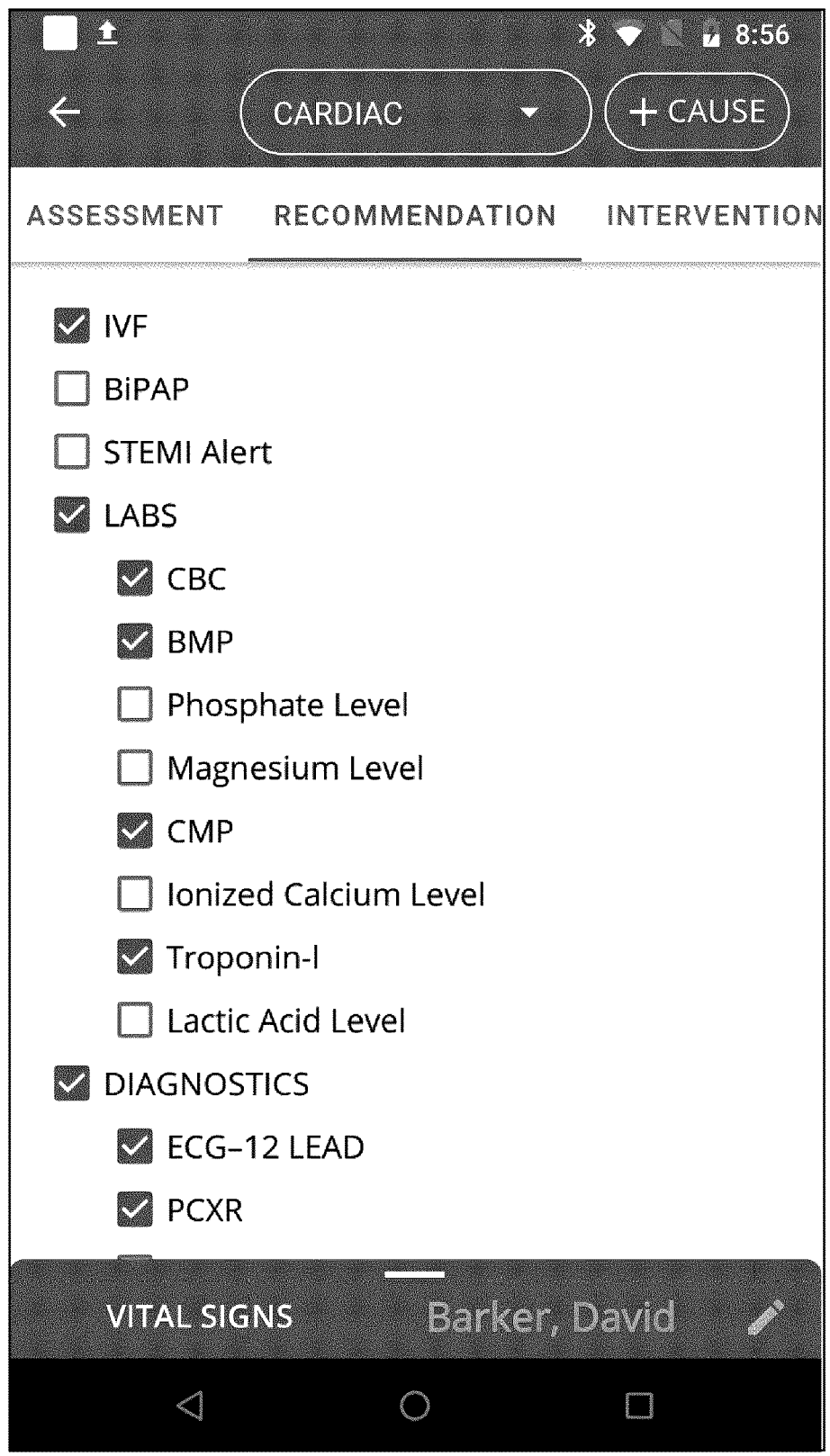

FIG. 16 shows a cardiac recommendation screenshot. The recommendation checklist is checked based on the Assessment of the authorized team member which would typically be the Critical Care Nurse. This checklist is available immediately to all team members. The Physician can override the Recommendation. All changes are recorded by the Backend for audit purposes. The above screens and the following two screens are sections of one continuous scrollable list.

Figure 17:
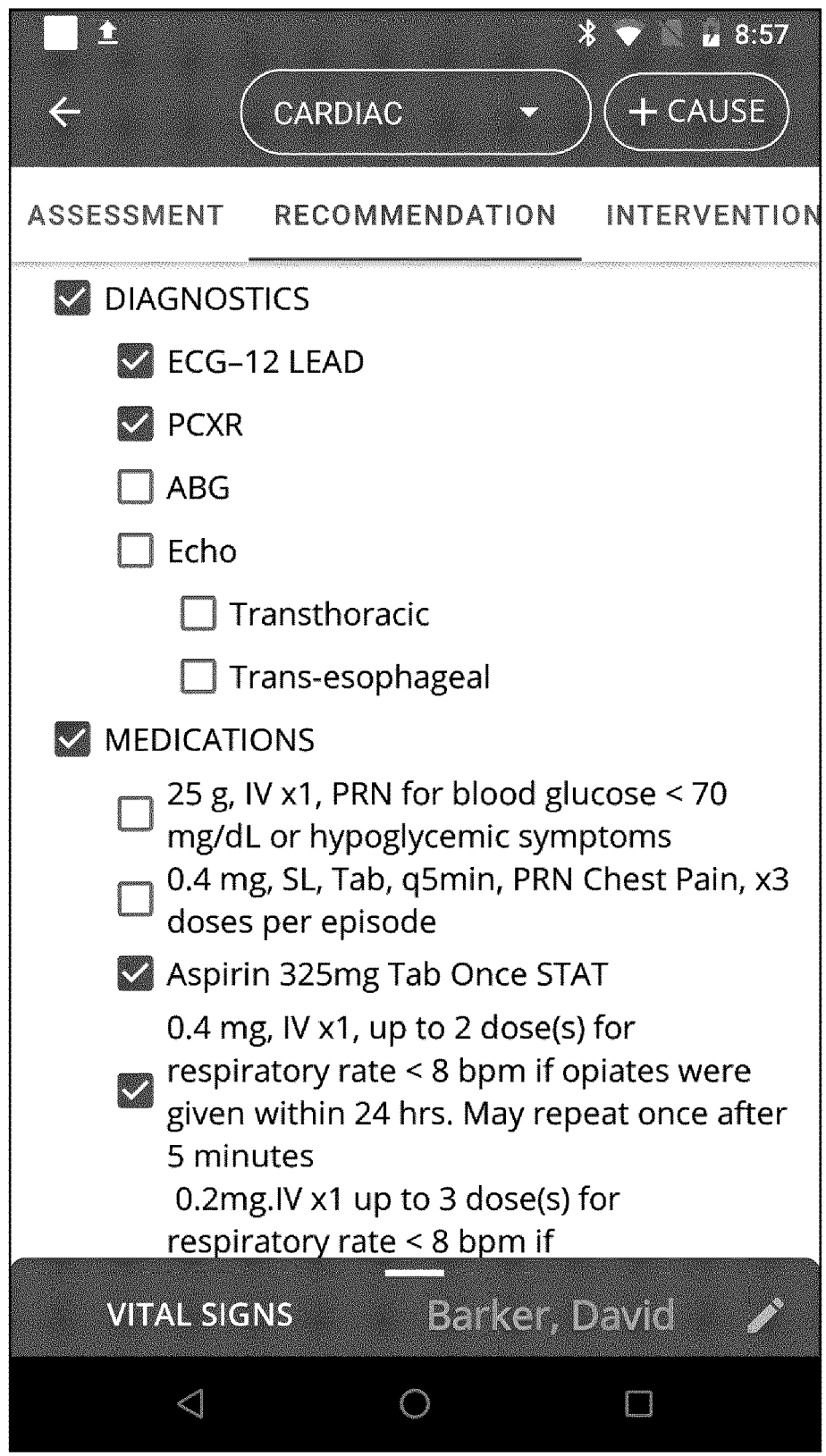

FIG. 17 shows a second view of the cardiac recommendation screenshot. This is the second screen of the cardiac recommendation checklist.

Figure 18:
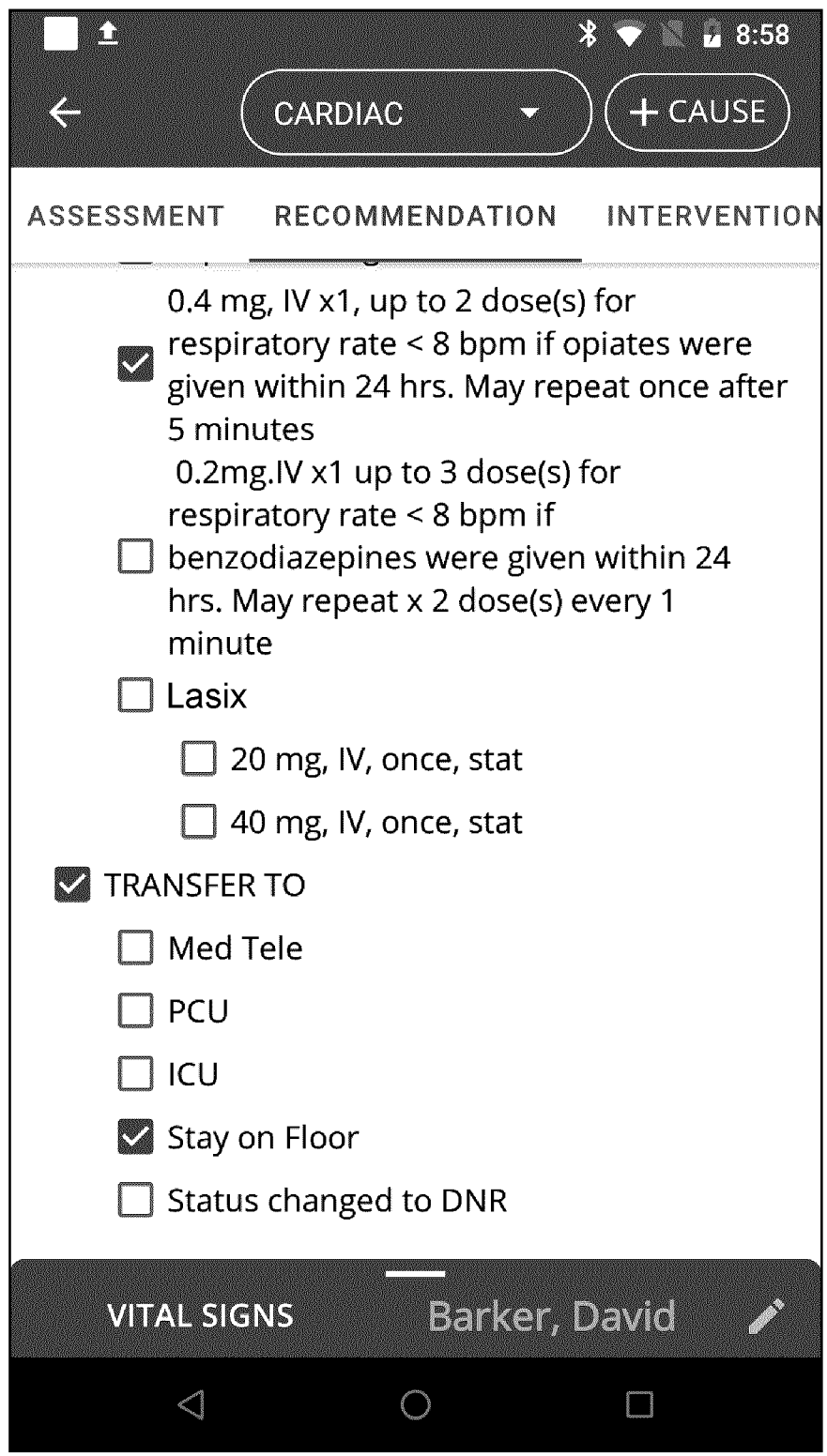

FIG. 18 shows a third view of the cardiac recommendation screenshot. This is the third screen of the cardiac recommendation checklist.

Figure 19:
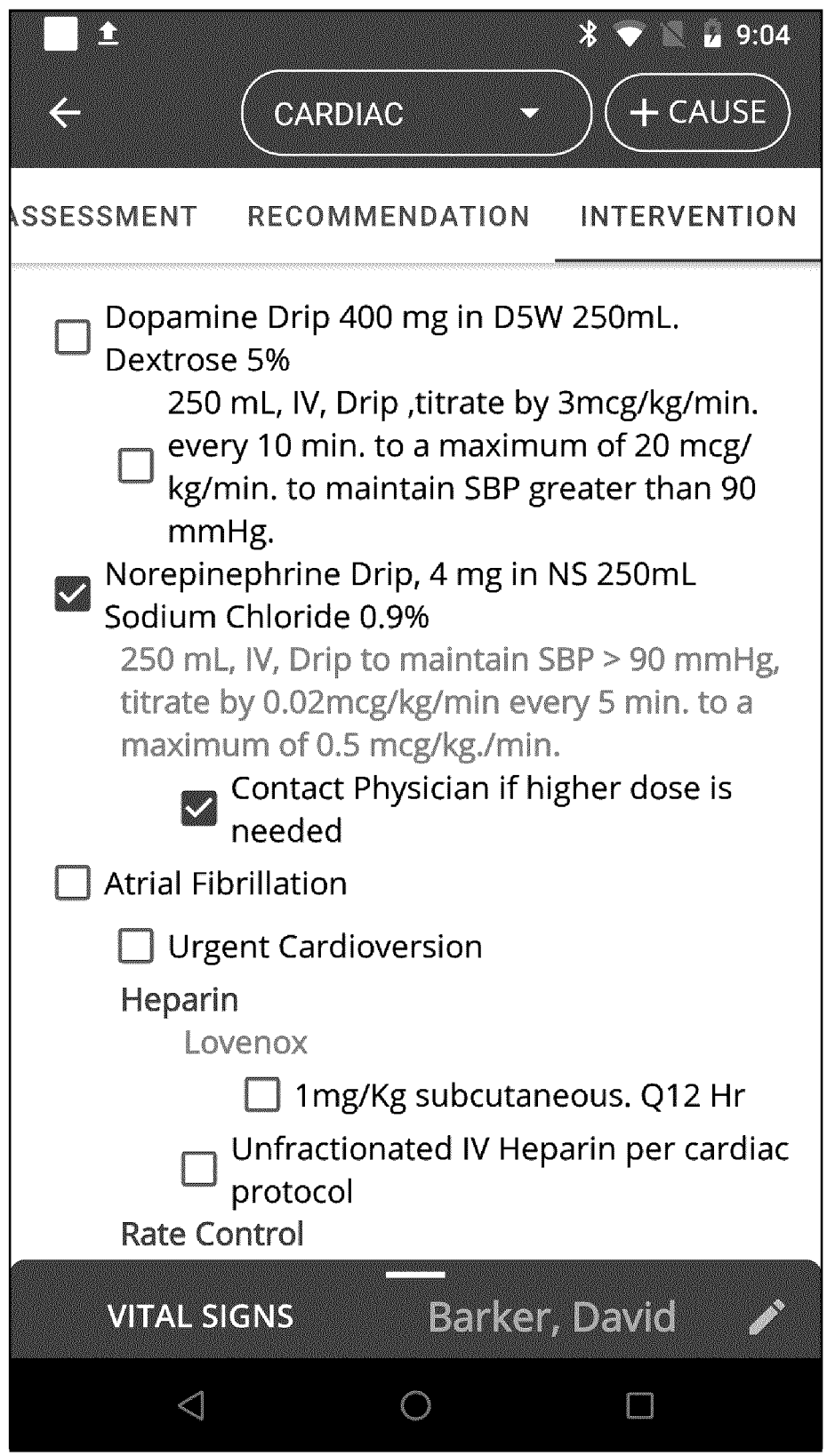

FIG. 19 shows a cardiac intervention screenshot. This screen lists those medications that only a Physician can order. Based on the patient's Situation, Background, Assessment and Recommendation, the Physician can approve the medications that are in Recommendations made by Critical Care Nurse and prescribe any additional medications using the Intervention checklist.

Figure 20:
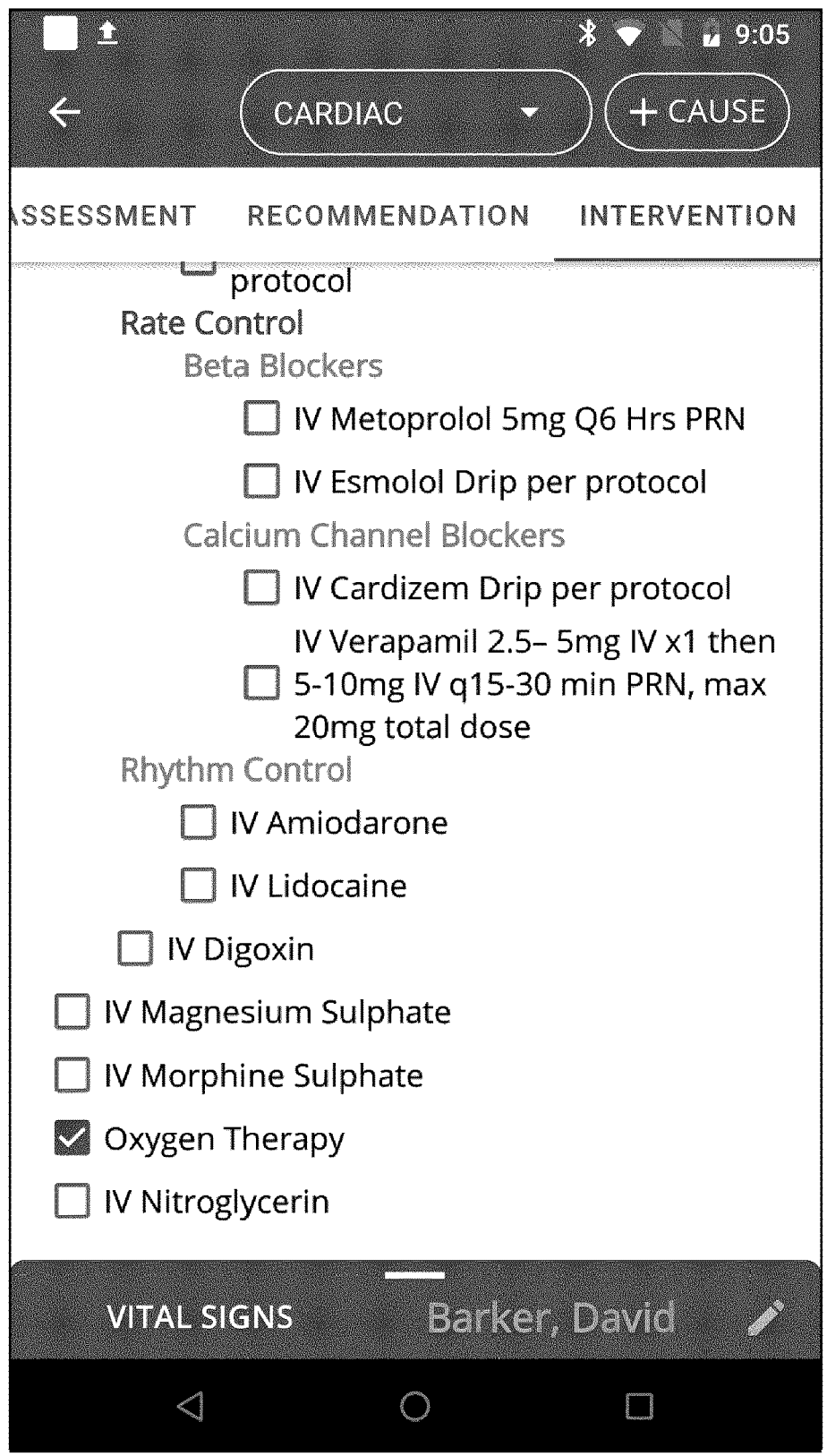

FIG. 20 shows a second screen of the cardiac intervention checklist.

Figure 21:
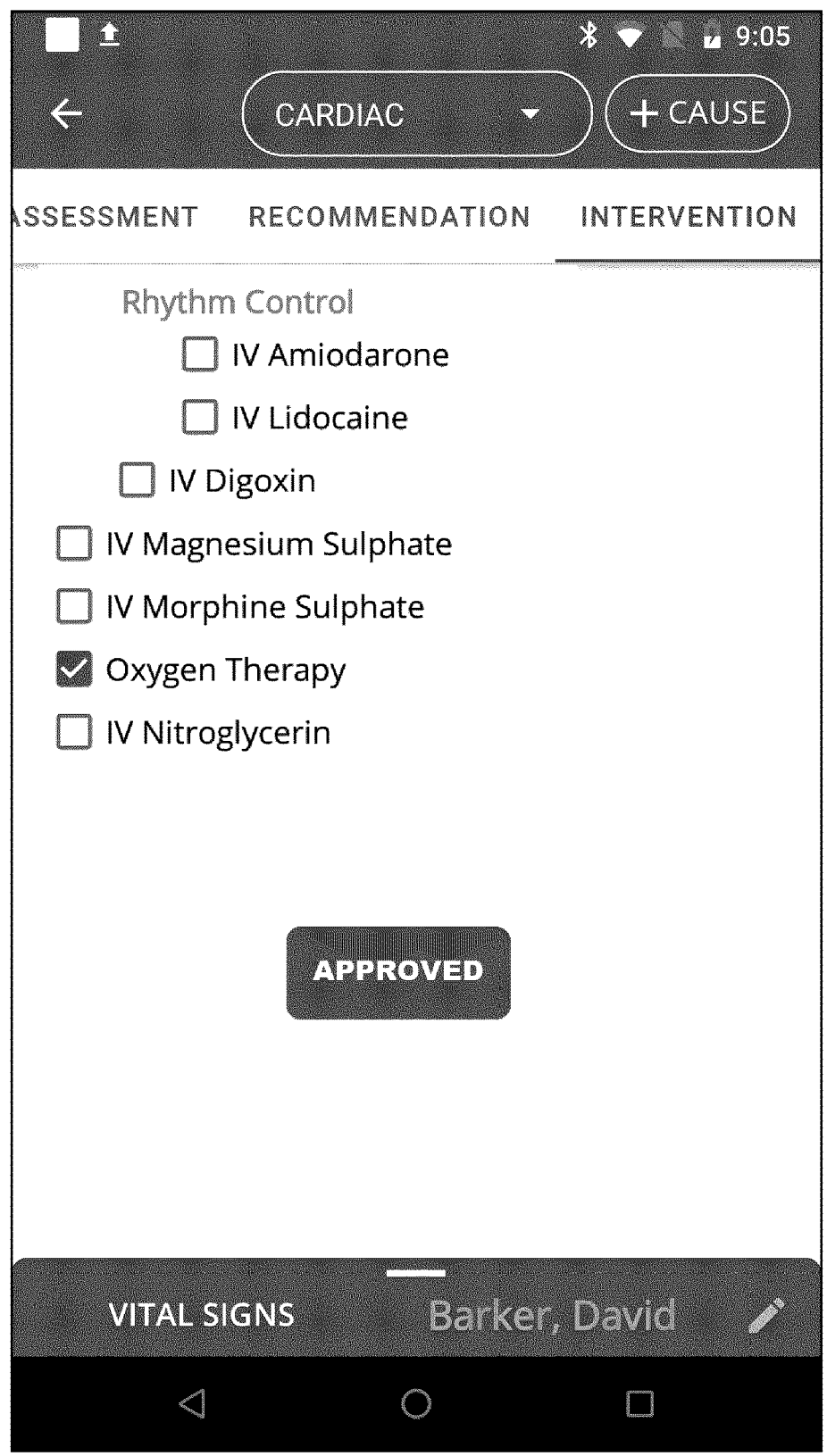

FIG. 21 shows a cardiac intervention screenshot. By tapping the "APPROVED" button, the Physician indicates to all the team members that they are to proceed with the Recommendations and the Medications checked in the intervention checklist. Only the Physician has the authority to approve the Recommendation and Interventions.

Figure 22:
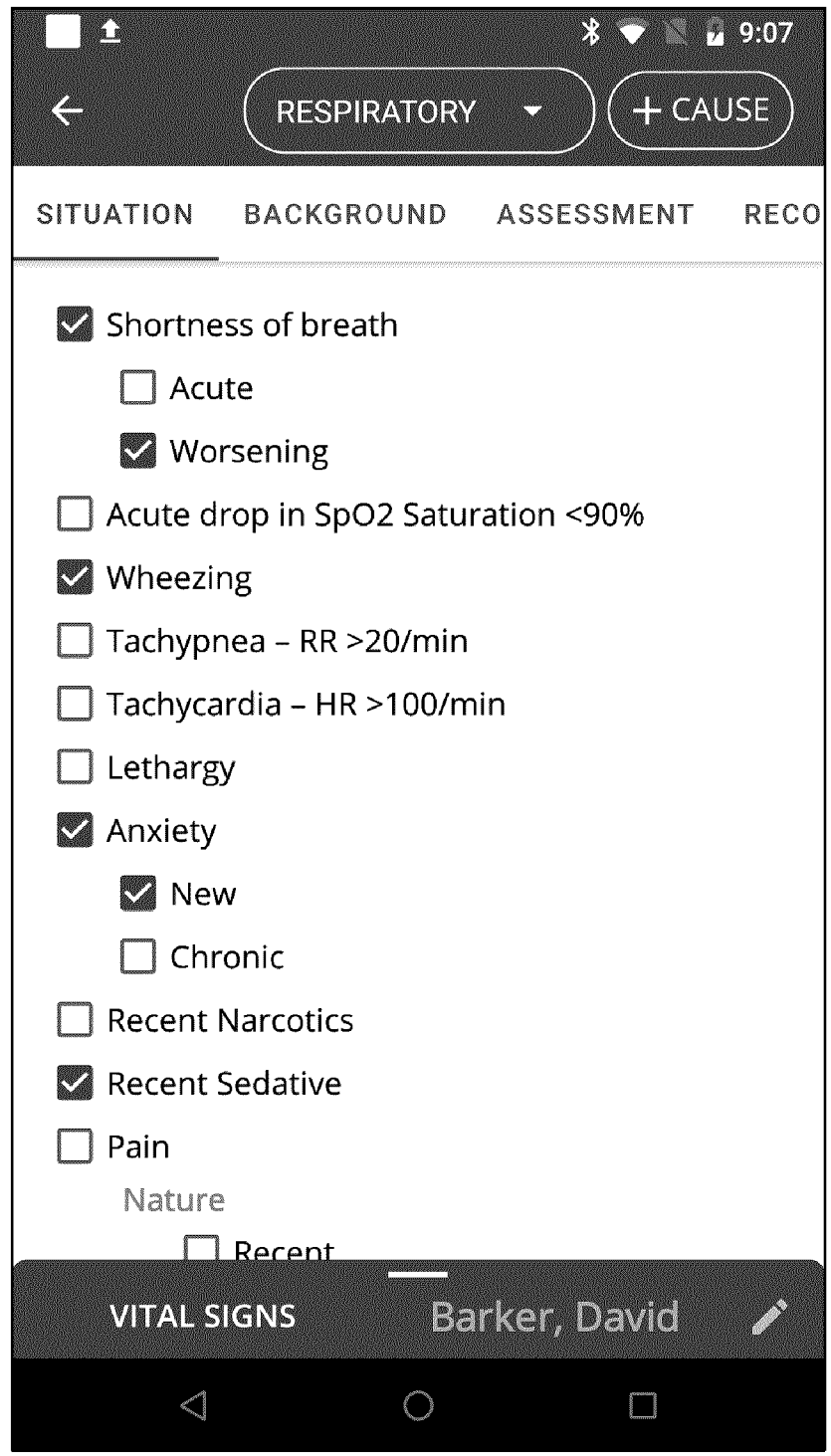

FIG. 22 shows a respiratory situation screenshot. This shows the first section of a patient's respiratory situation checklist.

Figure 23:
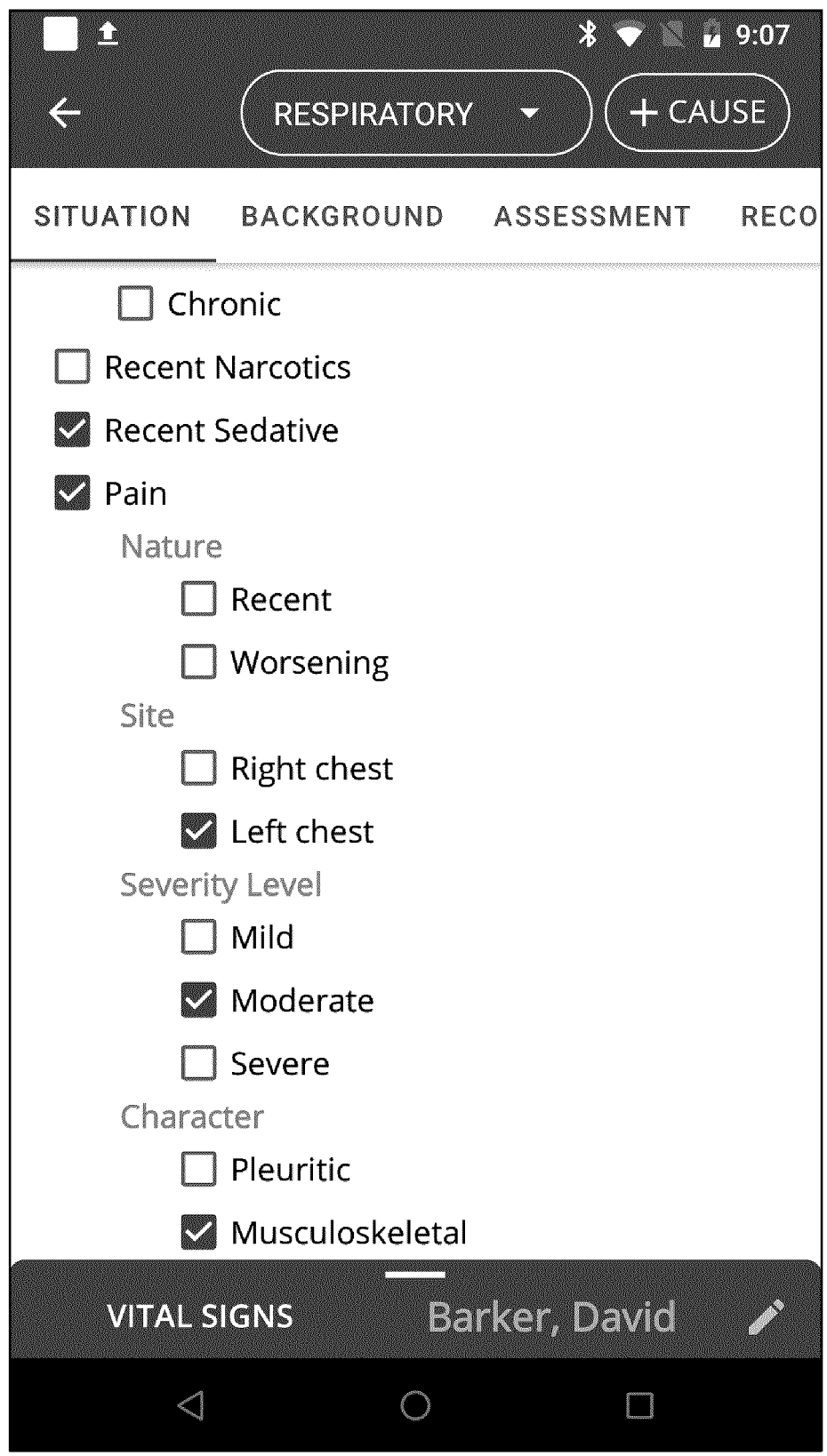

FIG. 23 shows a continuation of the patient's respiratory situation checklist.

Figure 24:
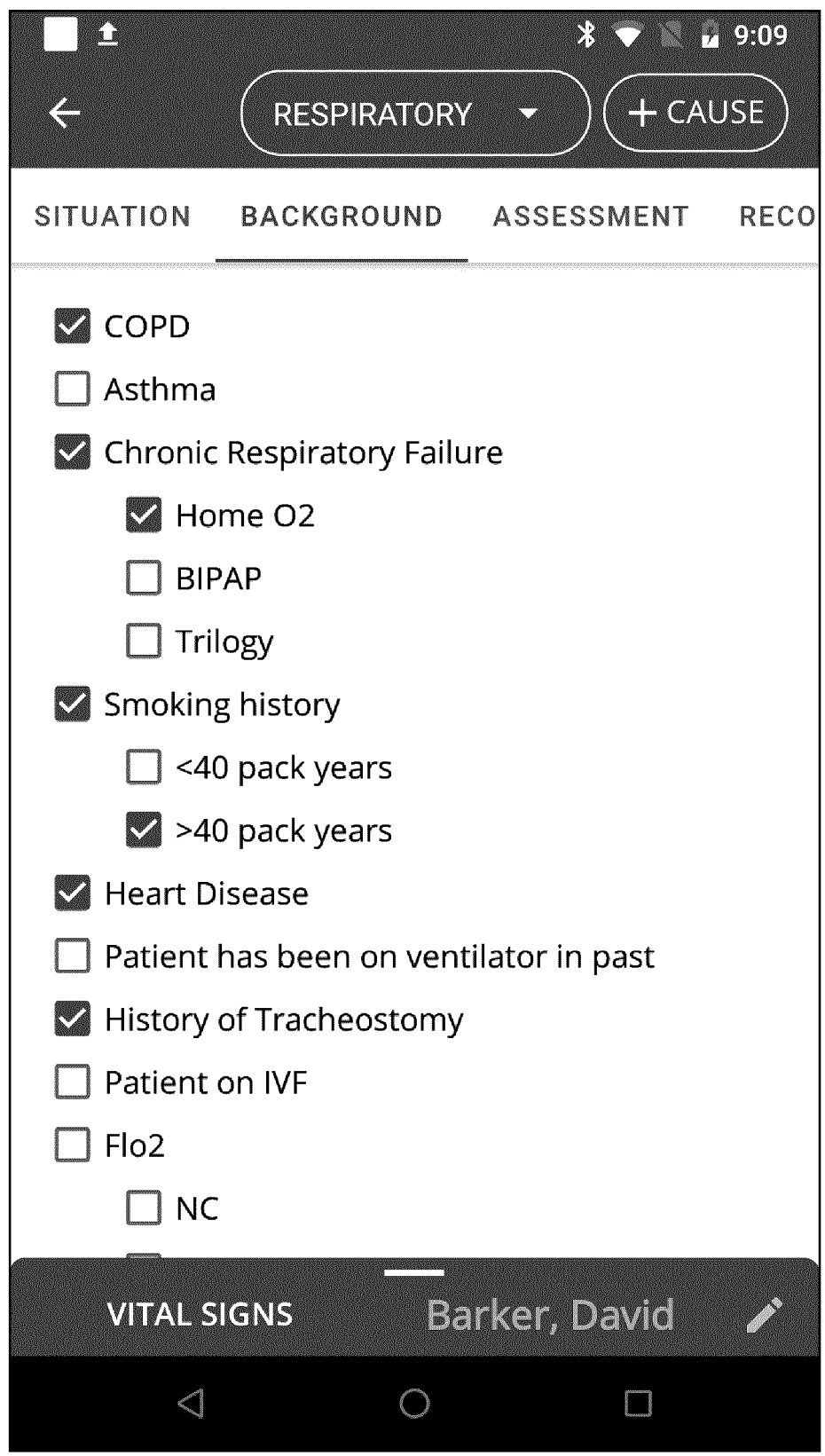

FIG. 24 shows a respiratory background screenshot. This is the first section of the patient's respiratory background checklist.

Figure 25:
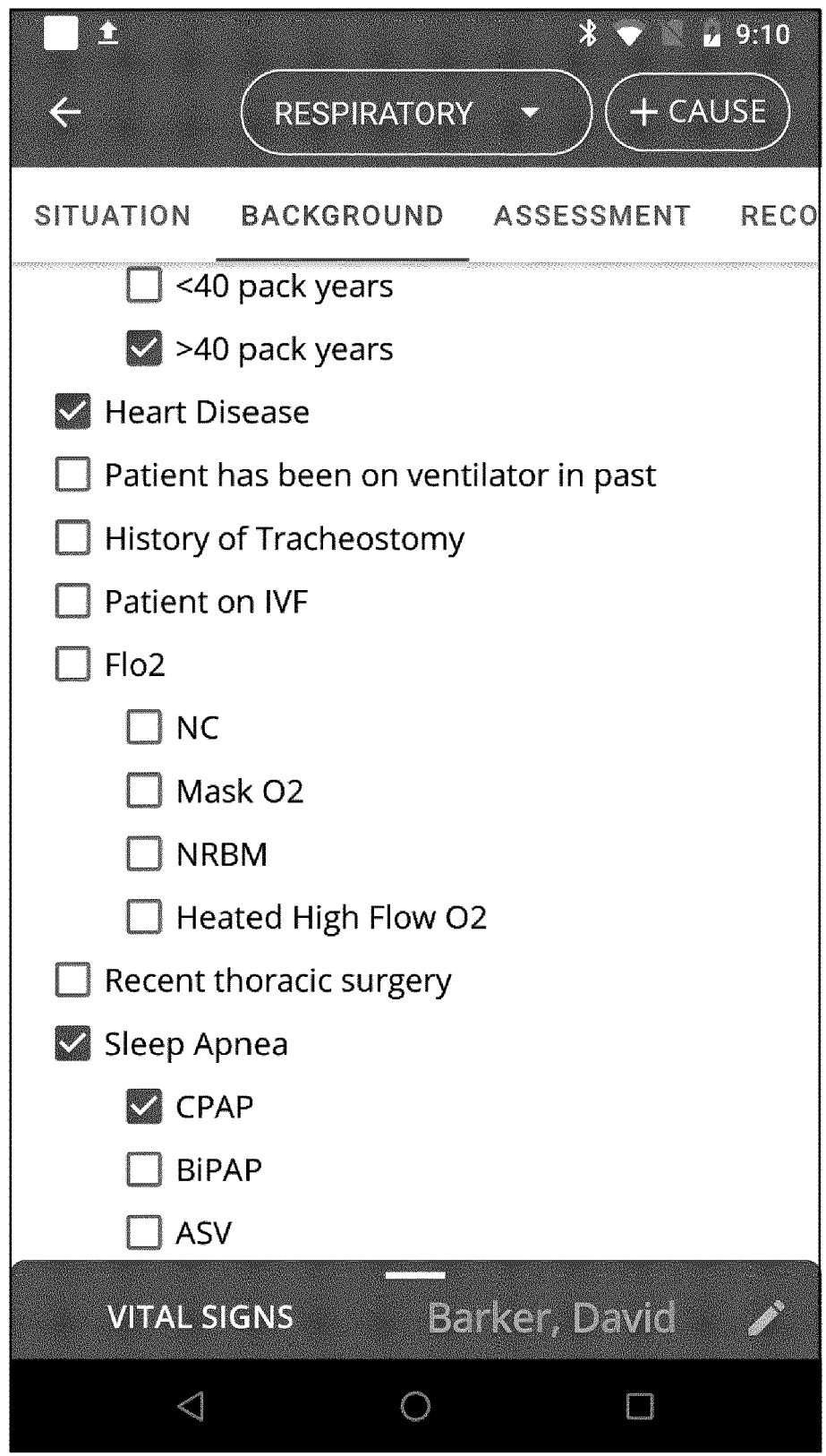

FIG. 25 shows a respiratory background screenshot. This is a continuation of the patient's respiratory background checklist.

Figure 26:
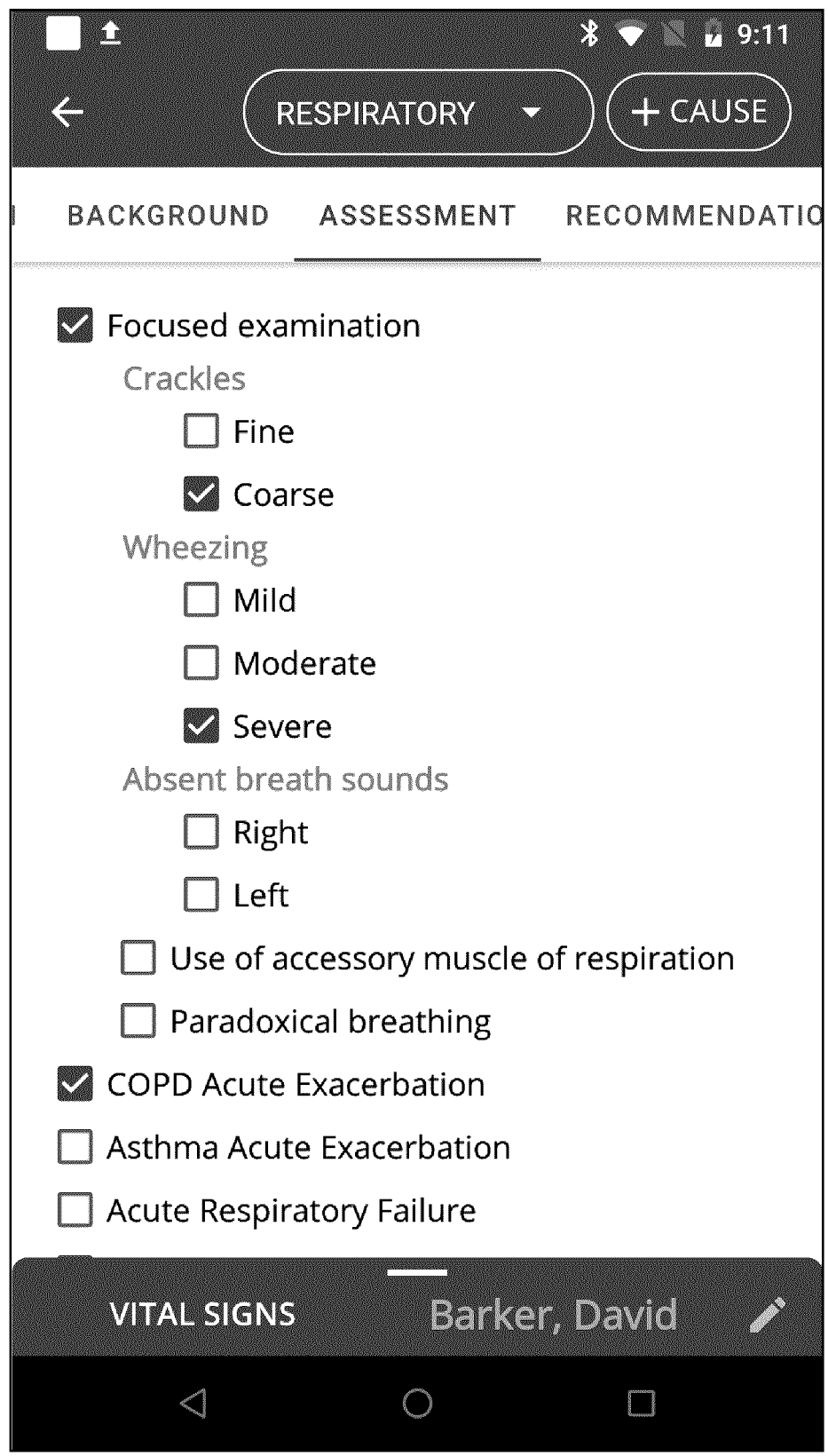

FIG. 26 shows a respiratory assessment screenshot. This is the first section of the patient's respiratory assessment checklist. Only authorized members can fill in checklist. This is typically done by the Critical Care Nurse. All members can instantly view the checklist.

Figure 27:
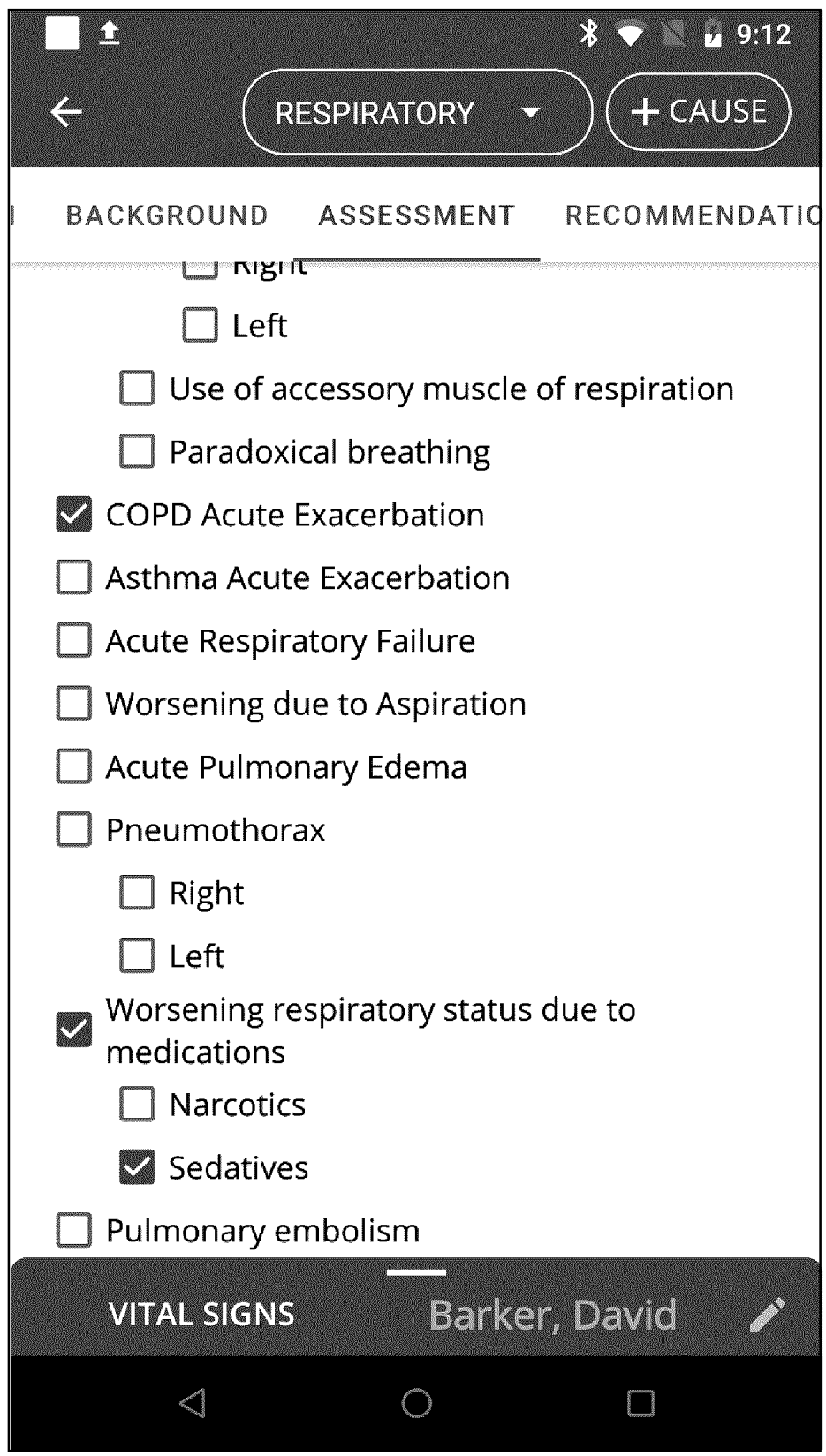

FIG. 27 shows a screenshot of a continuation of the respiratory assessment checklist.

Figure 28:
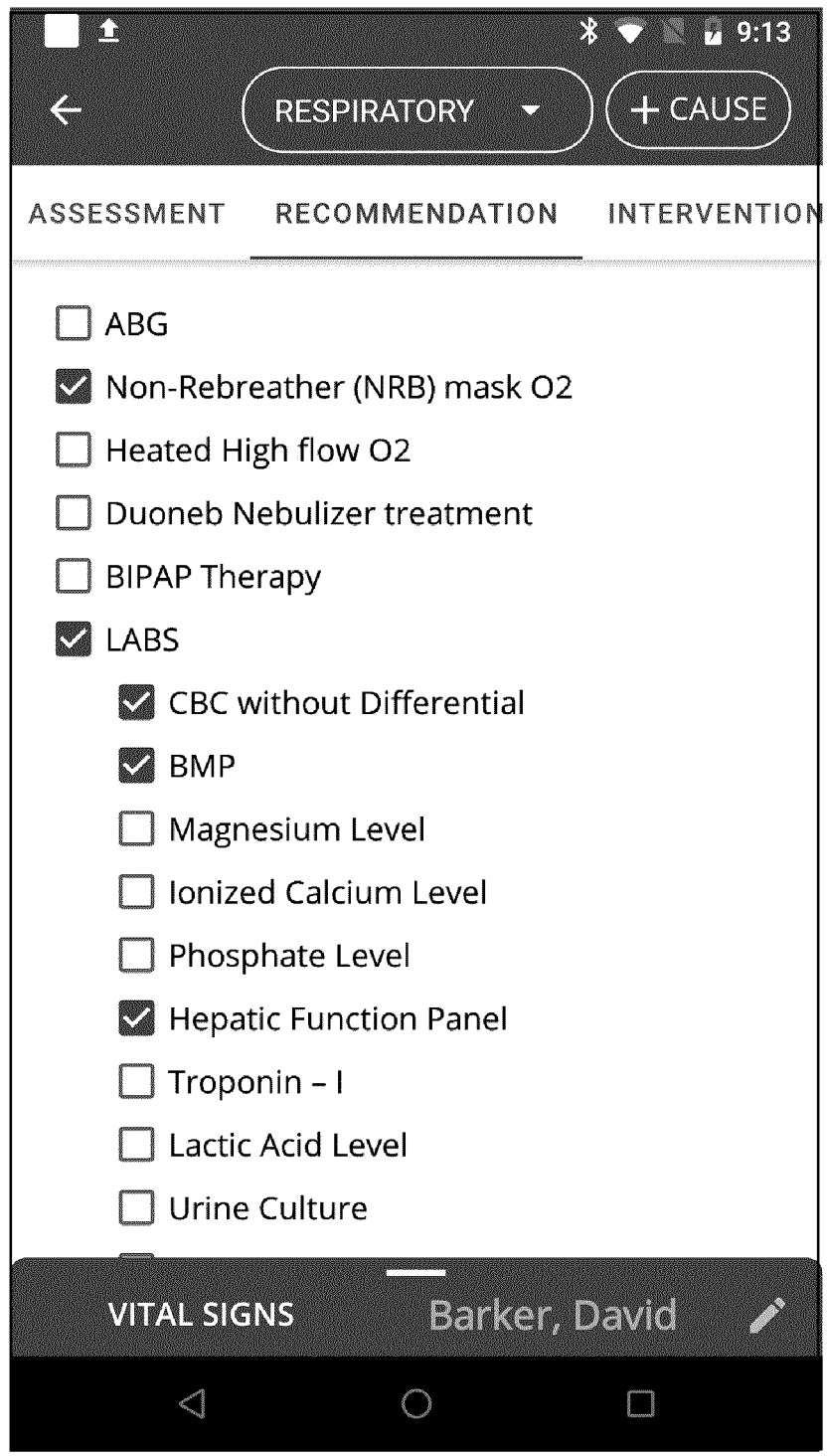

FIG. 28 shows a screenshot of the first section of the patient's respiratory recommendation checklist. Only authorized members can fill in checklist. Typically this is done by the critical care nurse. All members can instantly view the checklist.

Figure 29:
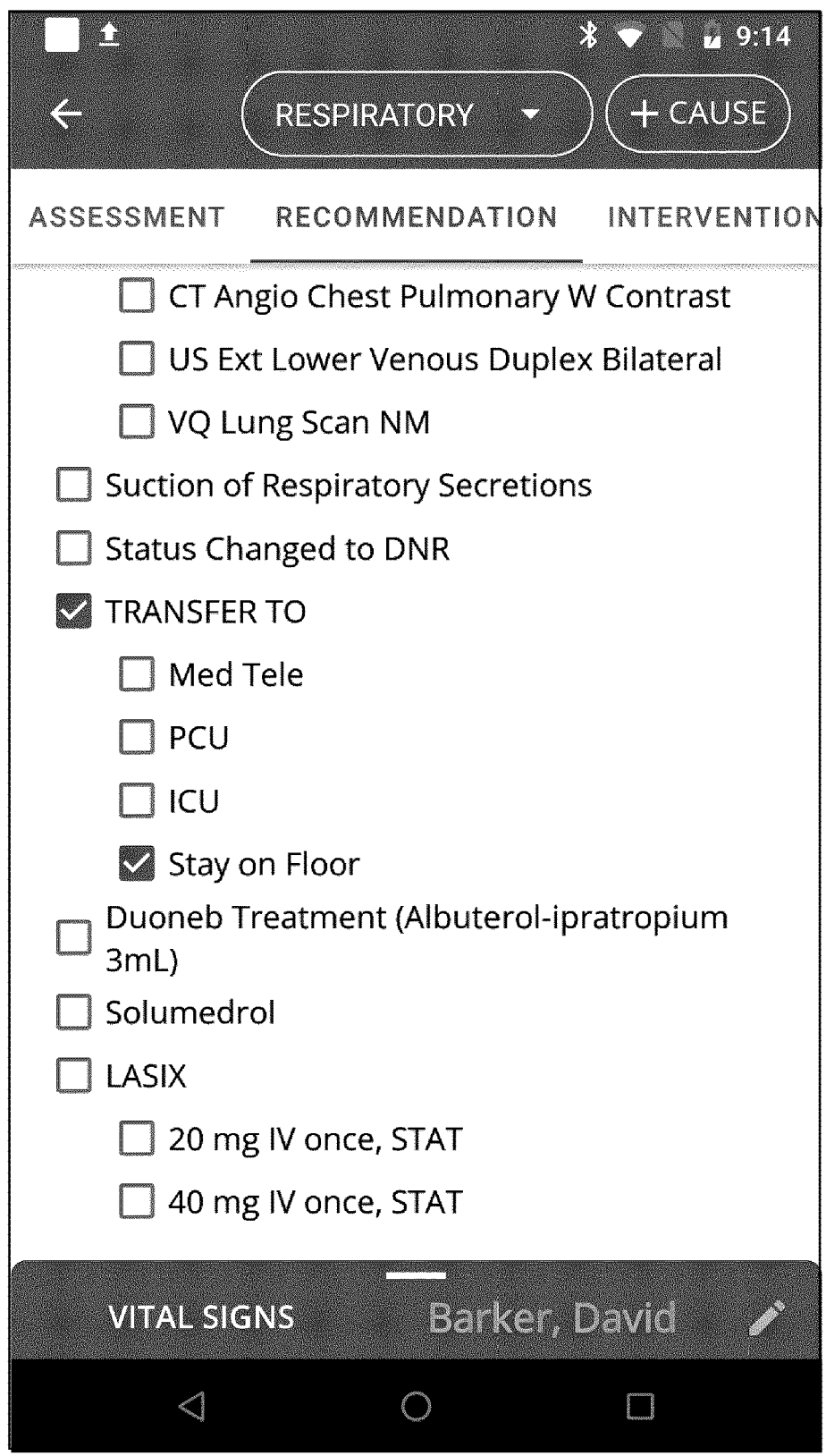

FIG. 29 shows a screenshot of a continuation of the patient's respiratory recommendation checklist.

Figure 30:
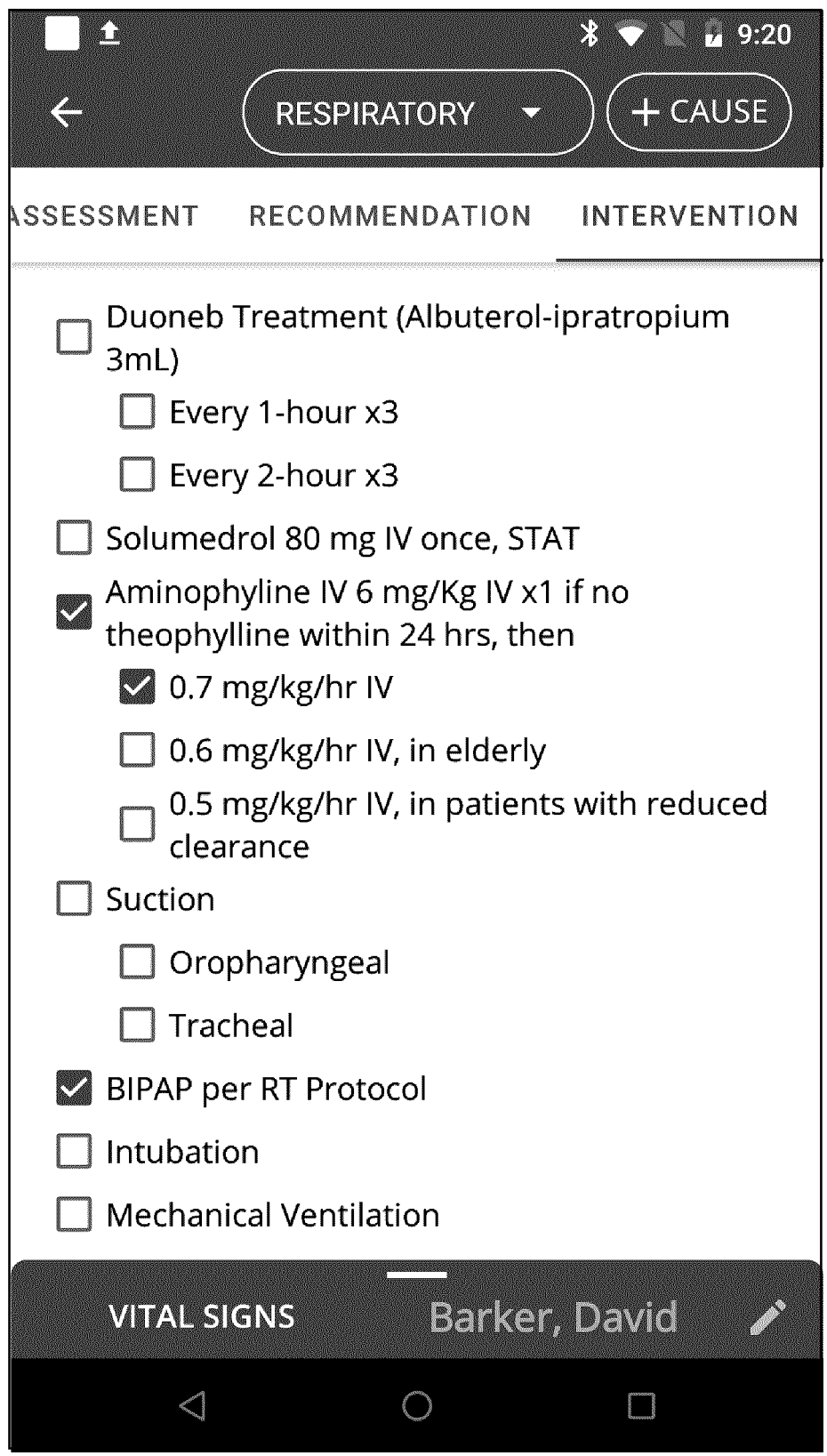

FIG. 30 shows a respiratory intervention screenshot. This screen lists those medications that only a Physician can order. Based on the patient's Situation, Background, Assessment and Recommendation, the Physician can approve the medication in the Recommendations made by Critical Care Nurse and prescribe any additional medications using the Intervention checklist.

Figure 31:
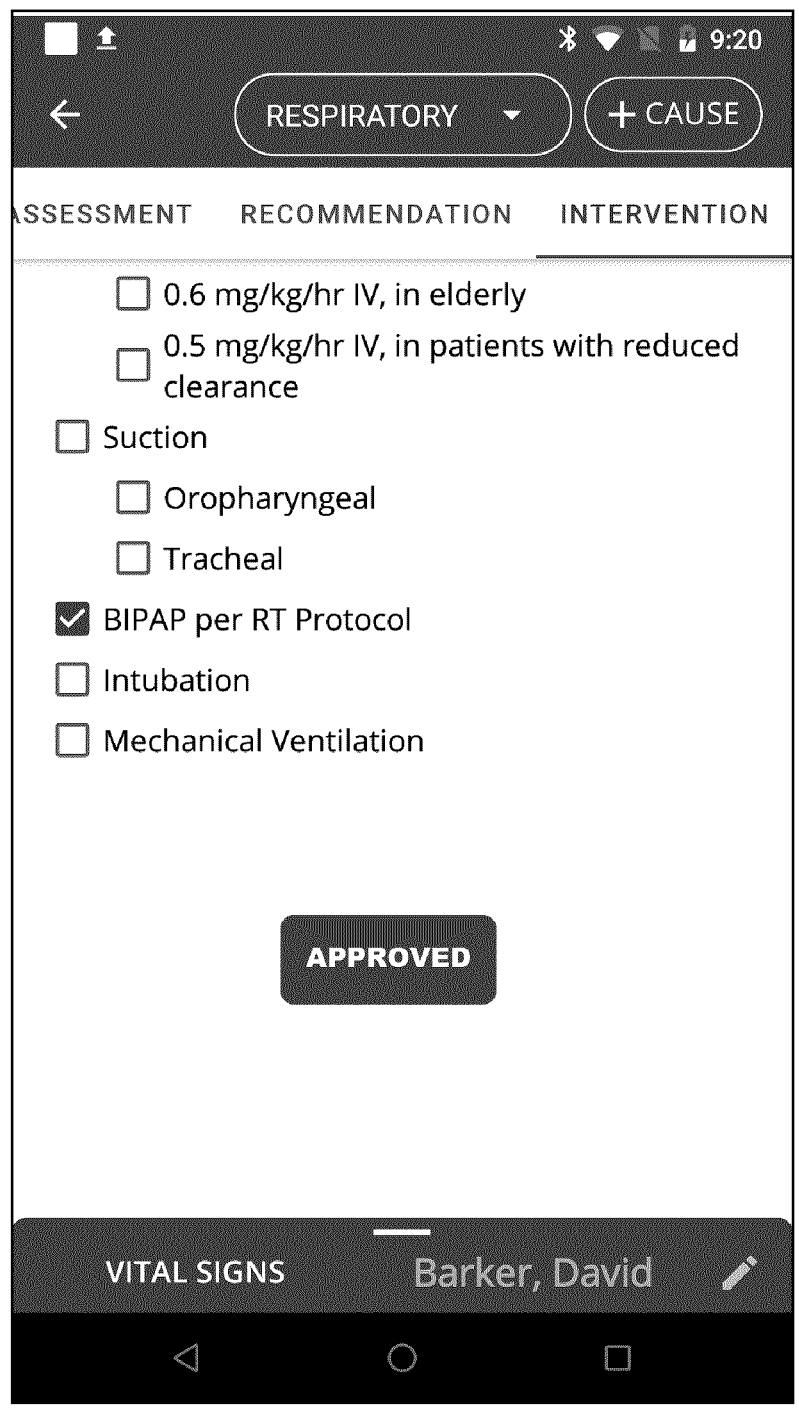

FIG. 31 shows another view of the respiratory intervention screenshot. By tapping the "APPROVED" button, the Physician indicates to all the team members that they are to proceed with the Recommendations and the Medications checked in the Intervention checklist. Only the Physician has the authority to approve the Recommendation and Interventions.

Figure 32:
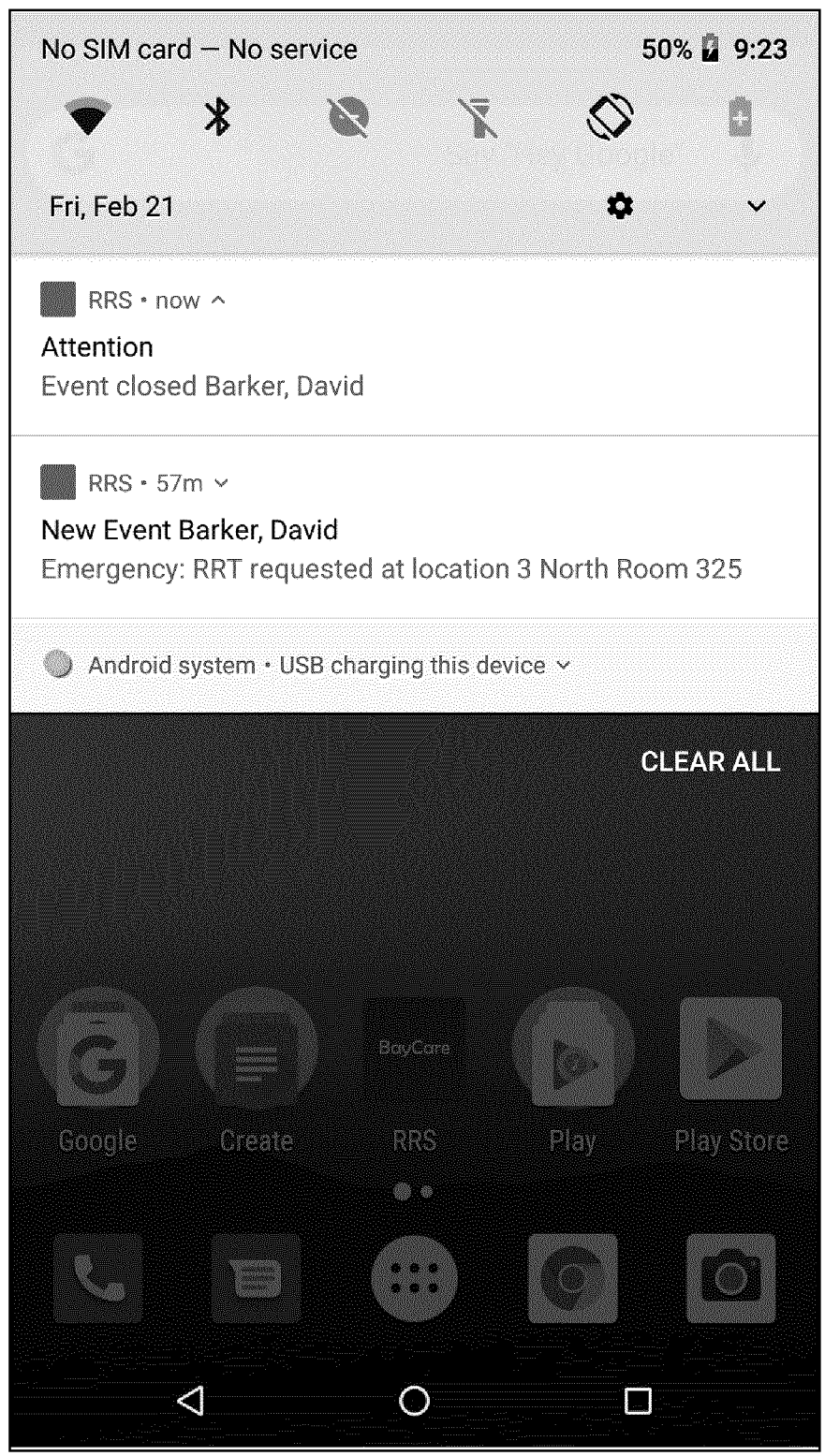

FIG. 32 shows a RRS close notification screenshot. Once all the Physician orders have been carried out, the authorized team member, typically the Critical Care Nurse, navigates to the event list screen and "Closes" the RRS event. All team members are sent the event closure notification as shown. The backend RRS system completes all the record keeping which can then be recalled by the QA group for auditing and training purposes.

Figure 33:
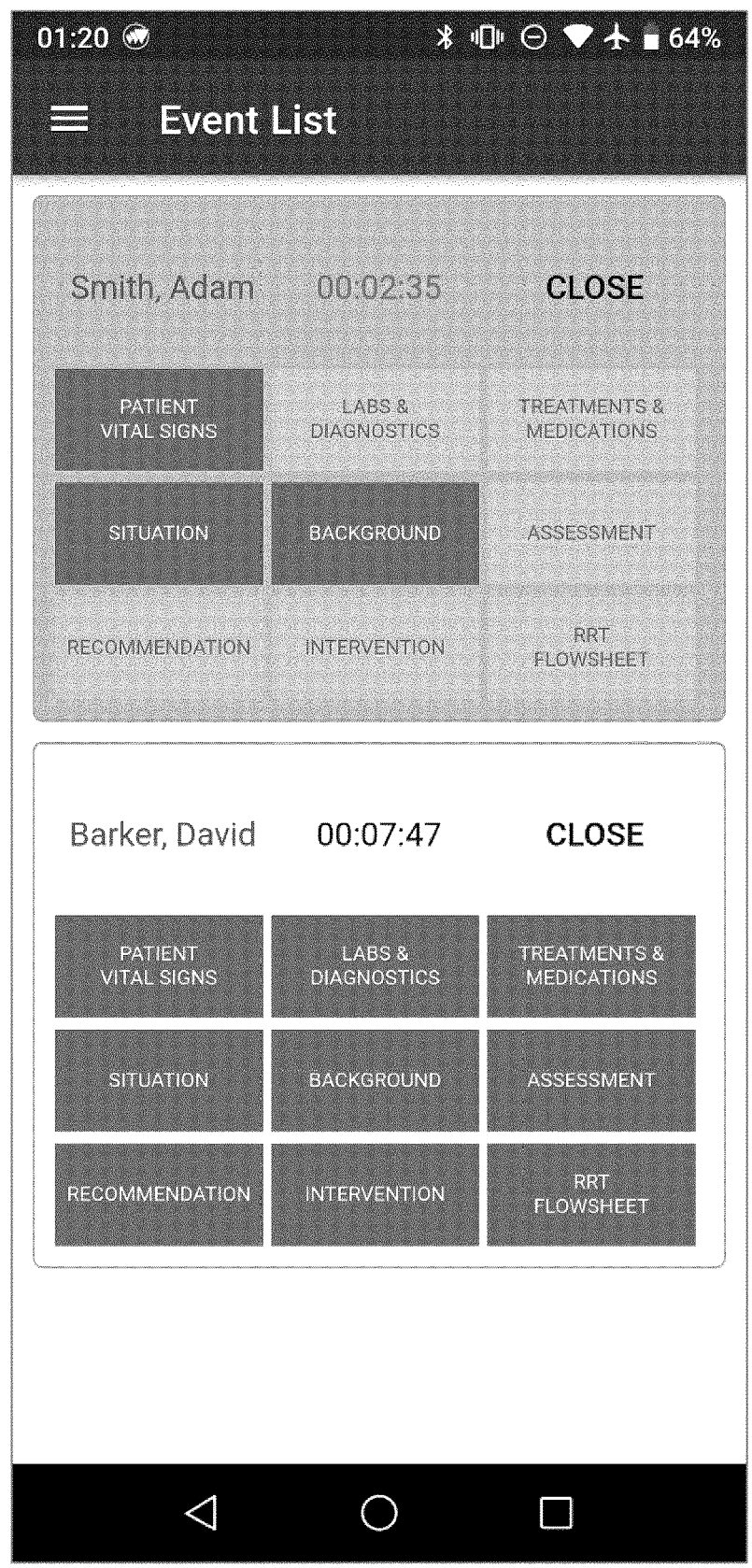
Figure 33A:
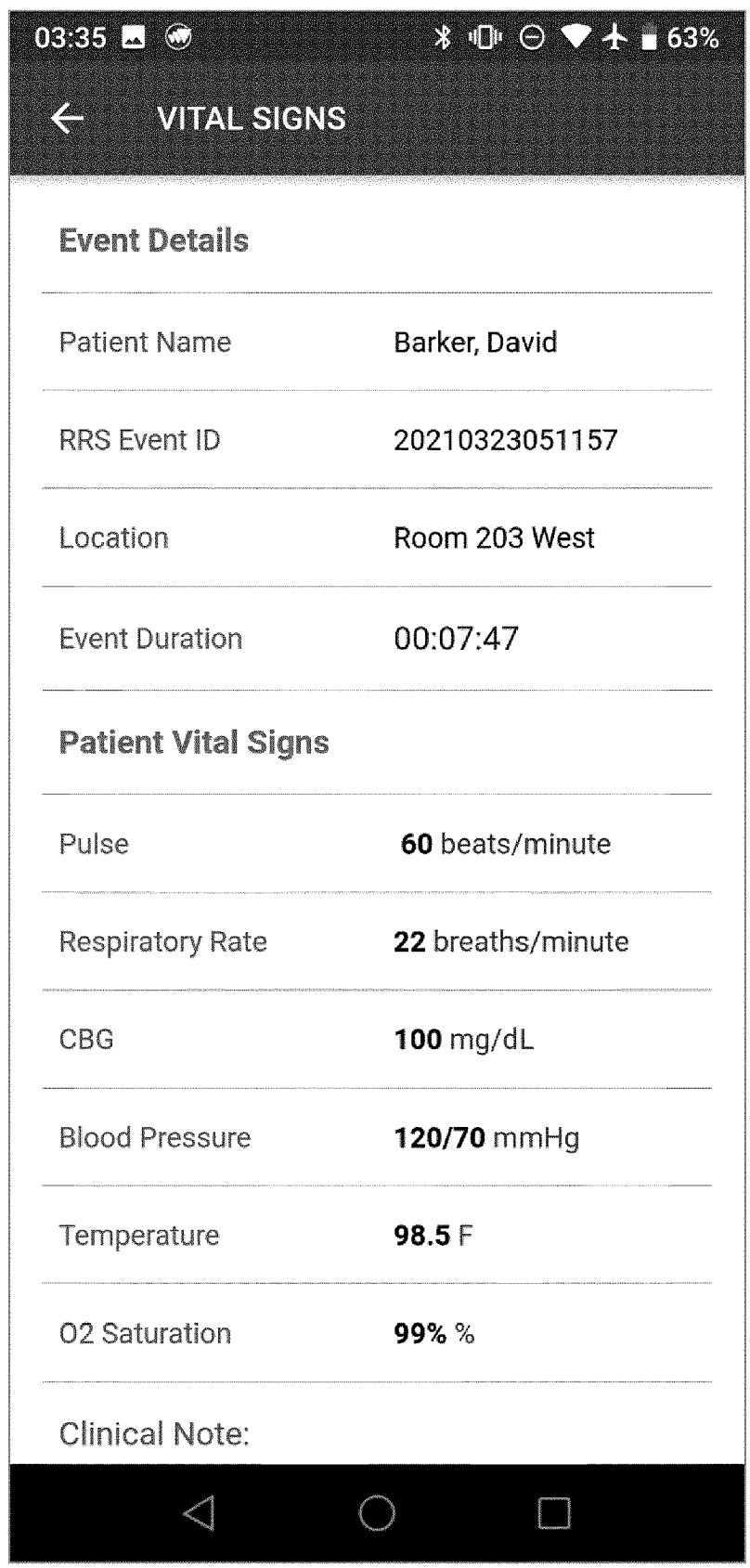
Figure 33B:
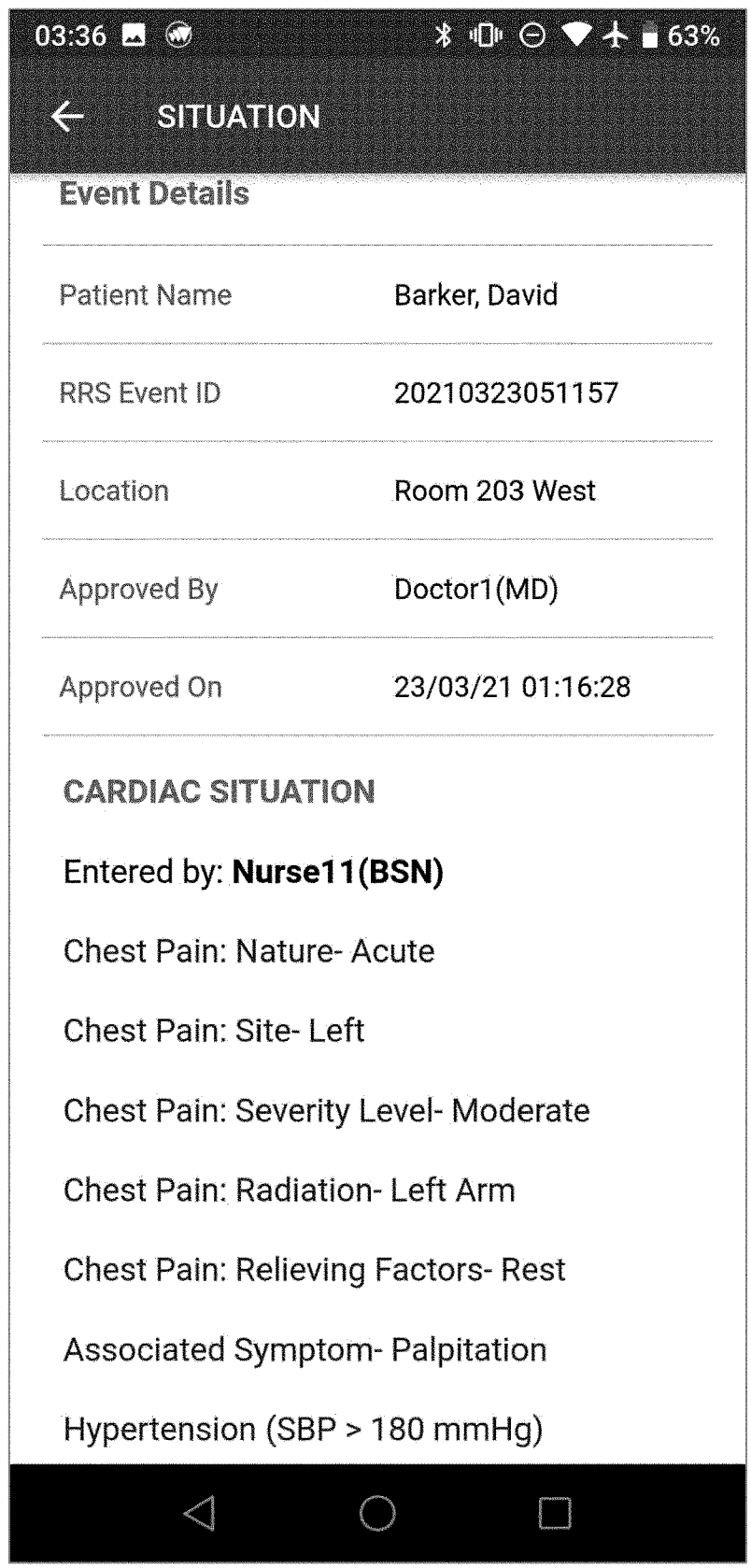
Figure 33C:
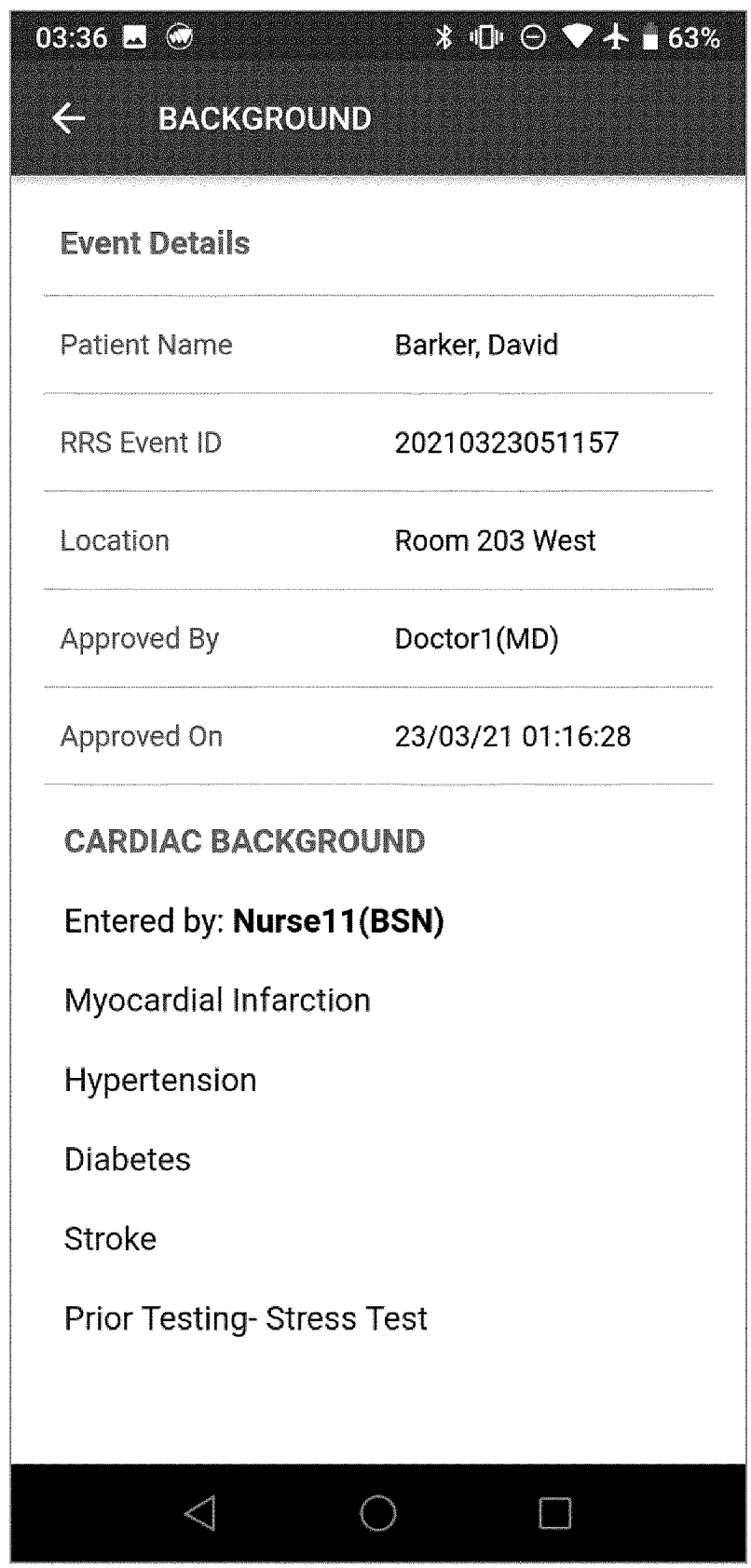
Figure 33D:
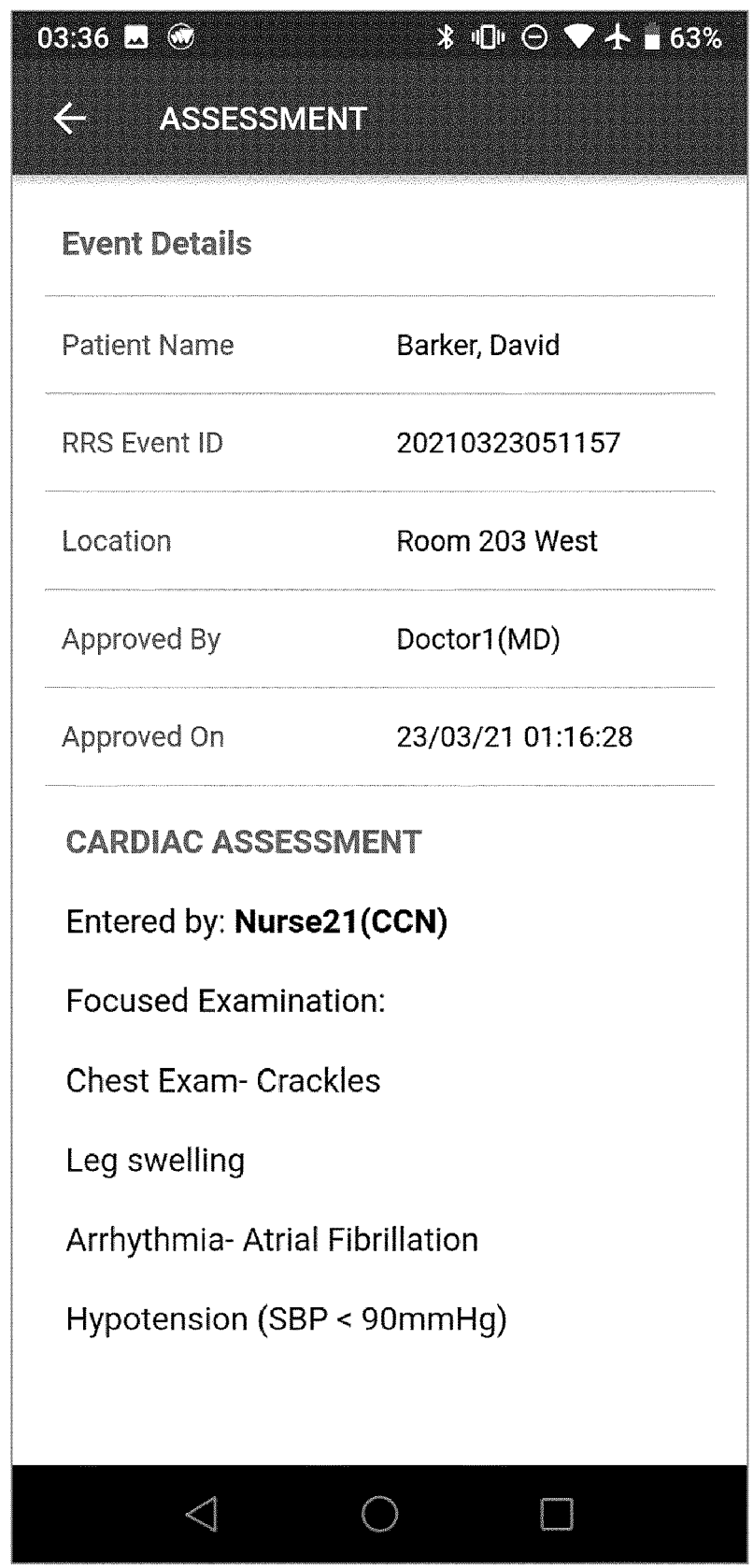
Figure 33E:
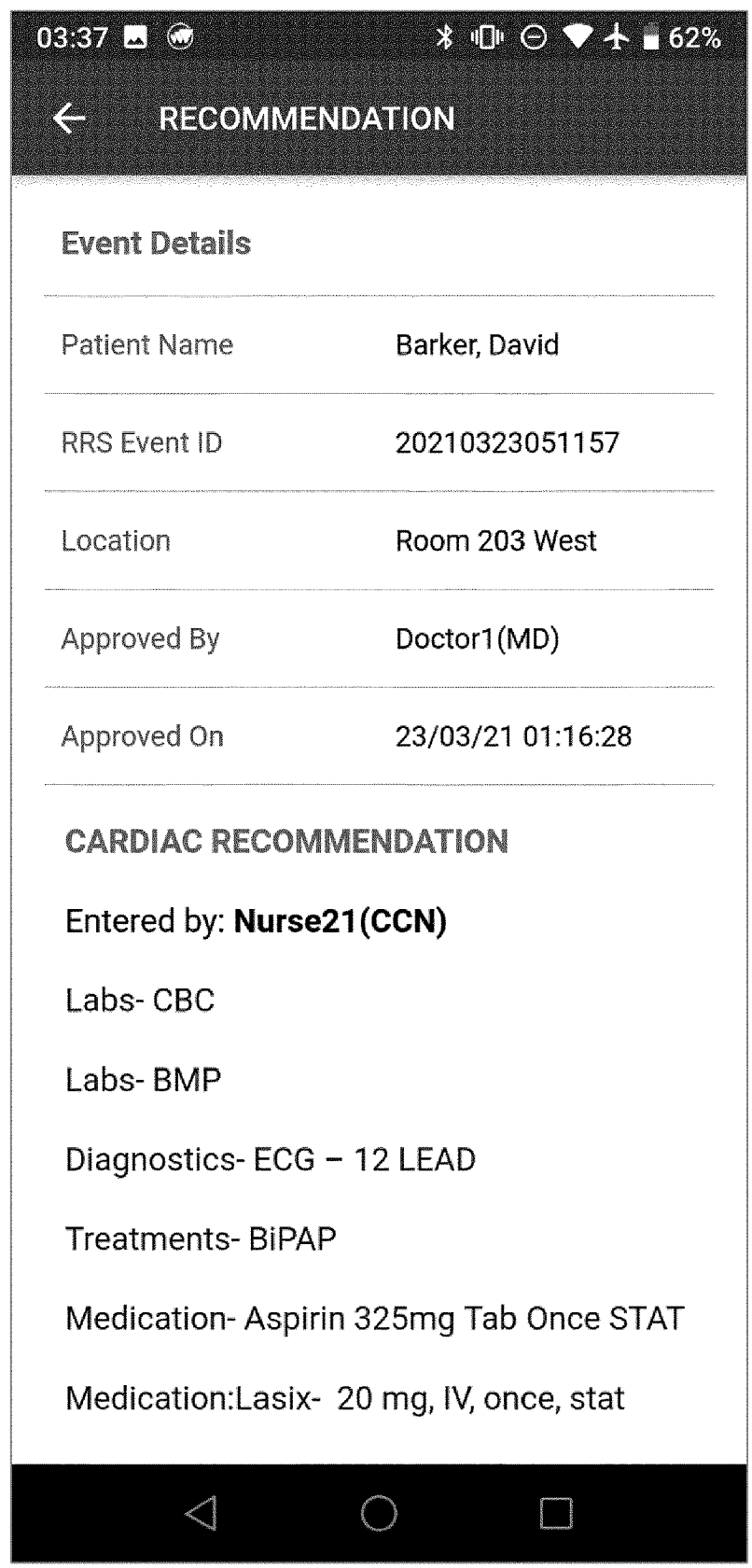
Figure 33F:
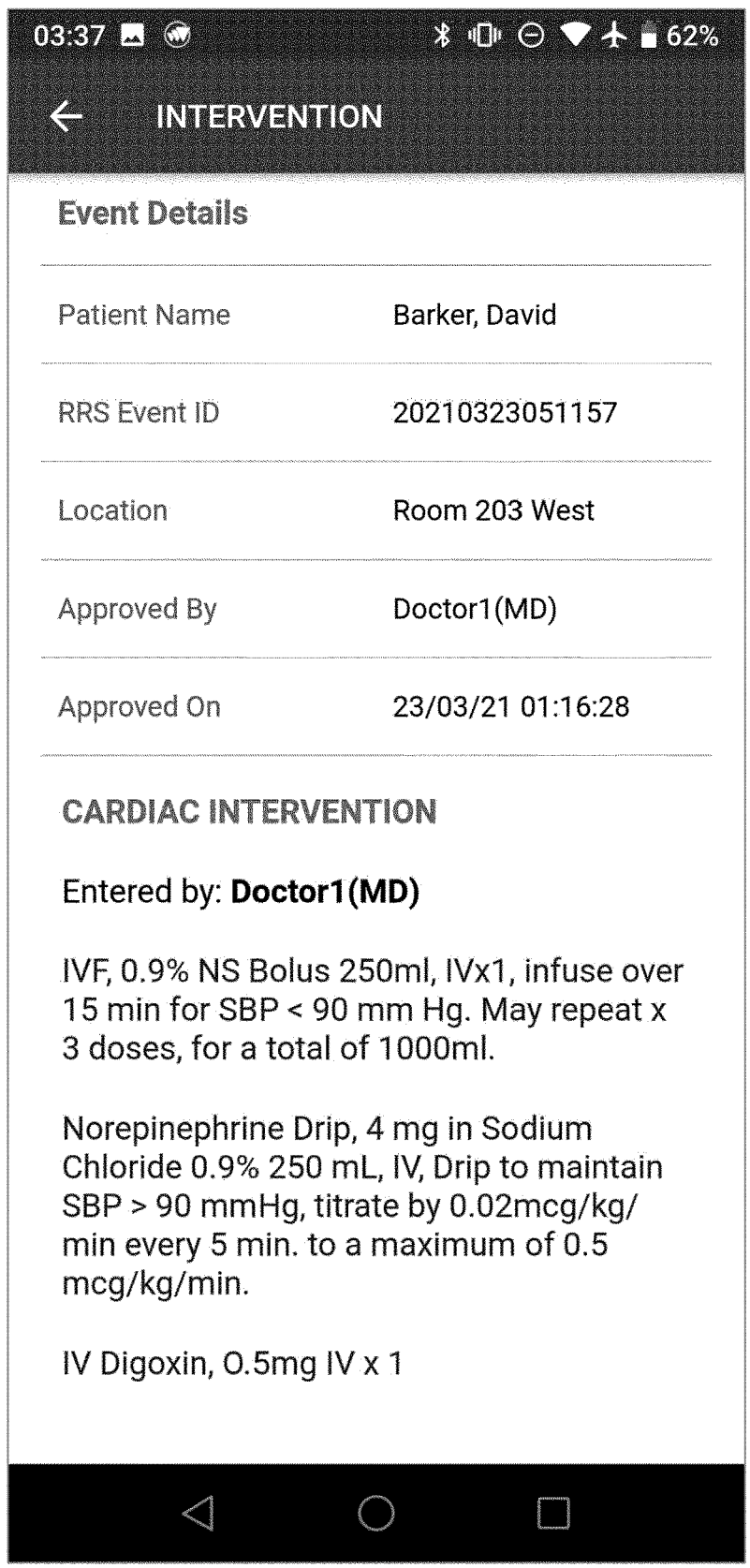
Figure 34:
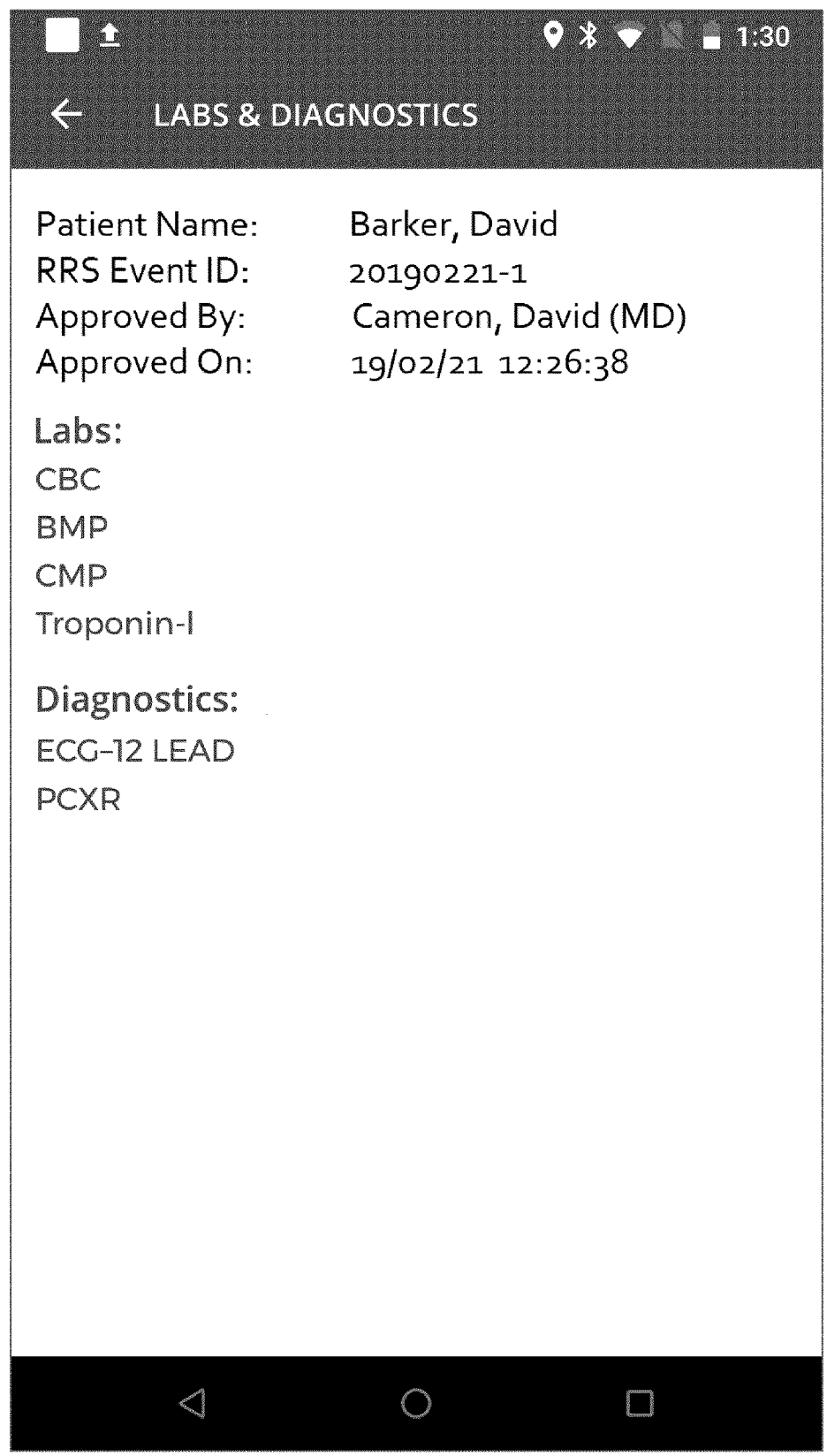

FIG. 33 shows the Event List of FIG. 7 after the Physician has approved the Recommendations and Intervention and the CCN has submitted the RRT Flowsheet which is detailed summary of the RRS Event. The nine boxes in green color signifies that the Physician has approved the Labs & diagnostics and Treatments & Medications. The green RRT Flow Sheet box indicates that the CCN has added any comments and submitted the RRT Flowsheet. Tapping a box opens up a new screen with details shown in FIG. 33a to FIG. 33f FIG. 34 shows the screen that is displayed when the LAB & DIAGNOSTICS box is tapped. This screen lists the LABs and DIAGNOSTICS that were checked in the Recommendations checklist and approved by the Physician. This can now be used by the Lab Technician as the Physician's order to proceed with the listed tests.

Figure 35:
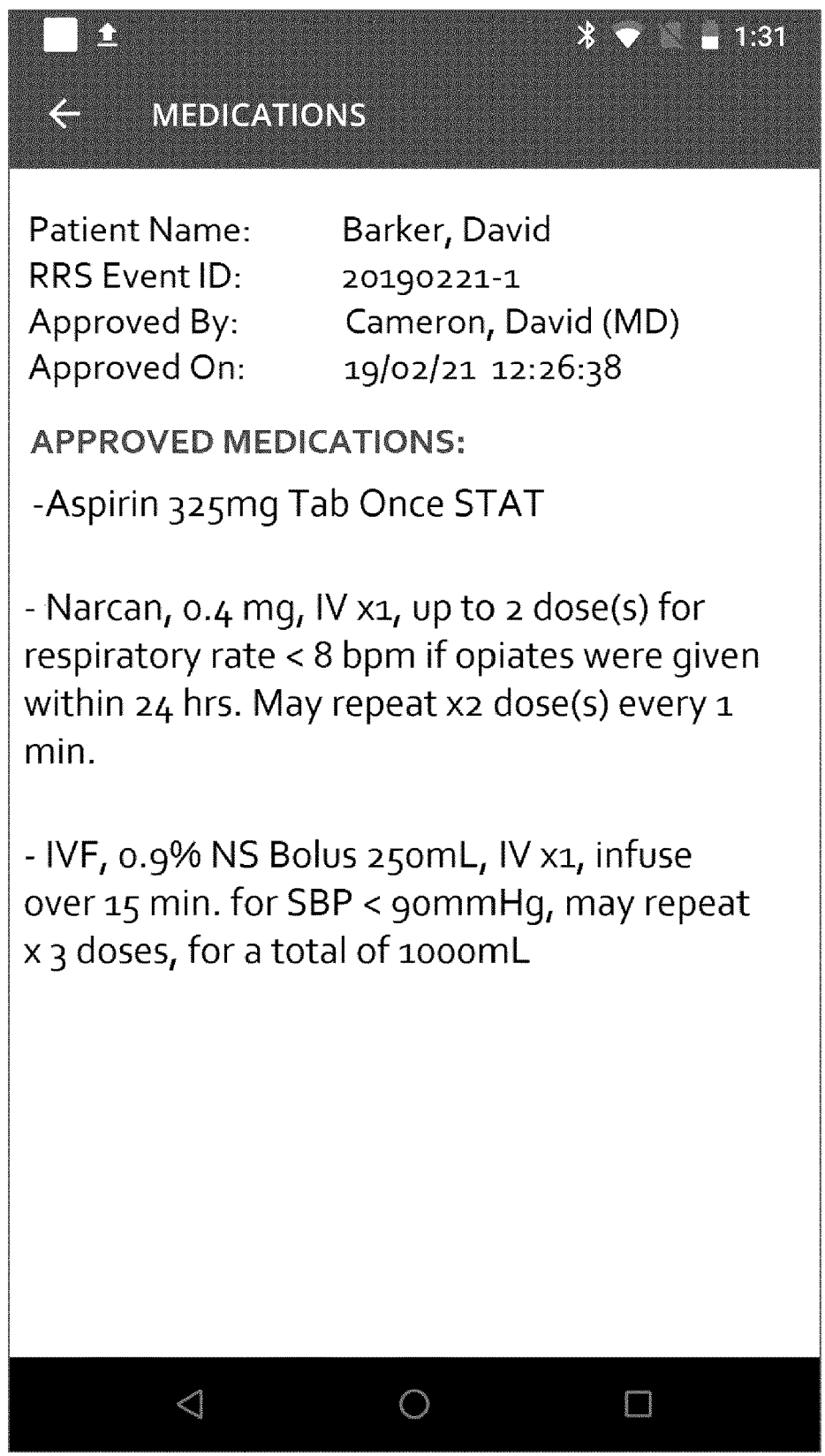

FIG. 35 shows the screen that is displayed when the MEDICATIONS box is tapped. This screen lists any medications that were checked in the Recommendation Check List by the CCN and approved by the Physician and the medications that the Physician has checked in the Intervention checklist. This screen can then be used by the Pharmacist as Physician's order to get the medication and administer to the patient.

Figure 36:
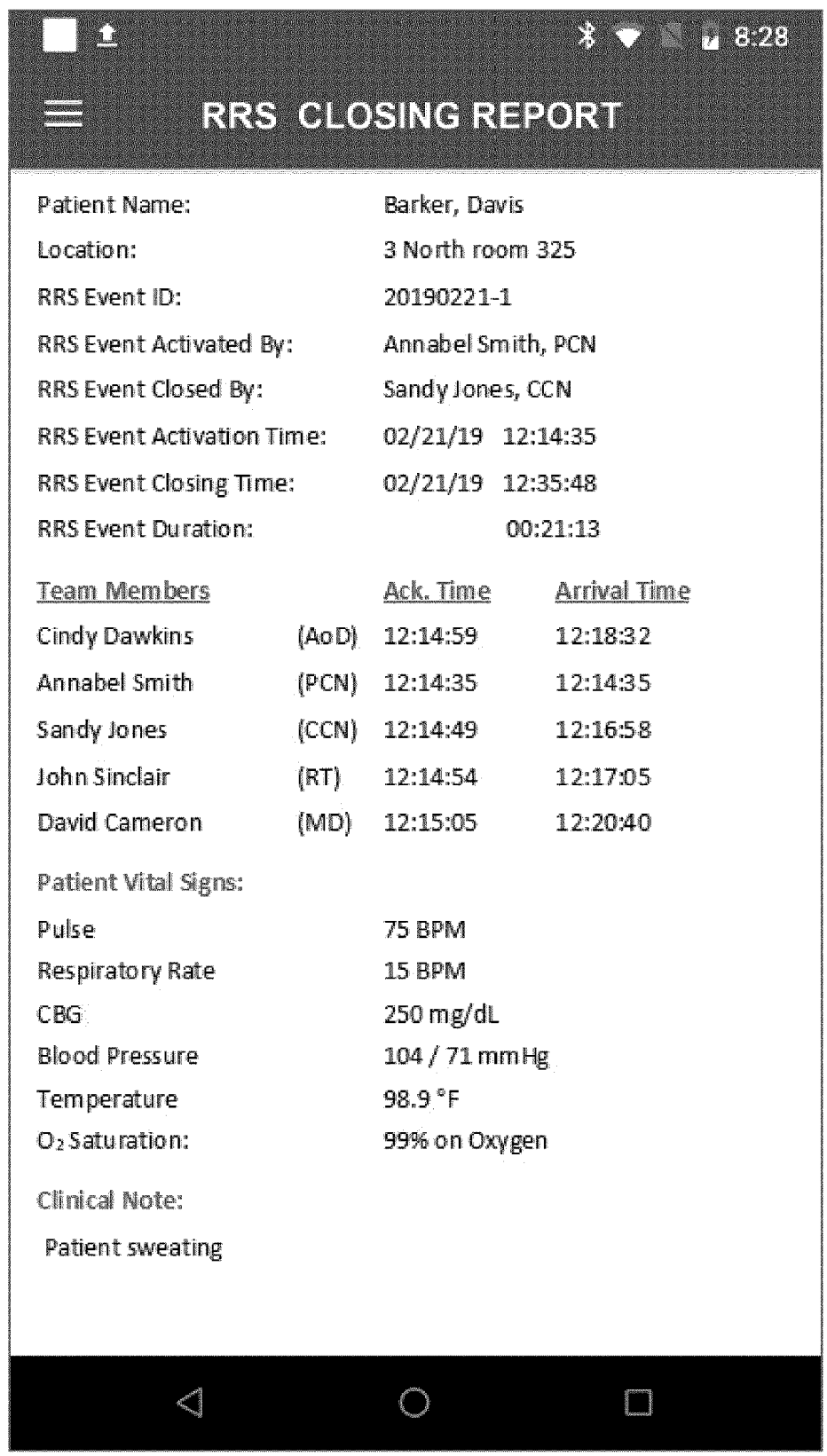

FIG. 36 shows the screen that is displayed when the CLOSING REPORT box is tapped. This screen provides a complete summary of the RRS Event indicating the person who activated the RRS event, the RRS Event ID that can be used to retrieve complete details of the RRS Event, Activation and Closing times, who closed the event and the event duration. This is followed by all the Team Members who participated in the event, the time each member acknowledged receiving the event notification and the time when the team member arrived at the patient location which is determined automatically using the method described earlier. This is followed by the Patient's Vital signs and any clinical note that may have been made.

Figure 37:
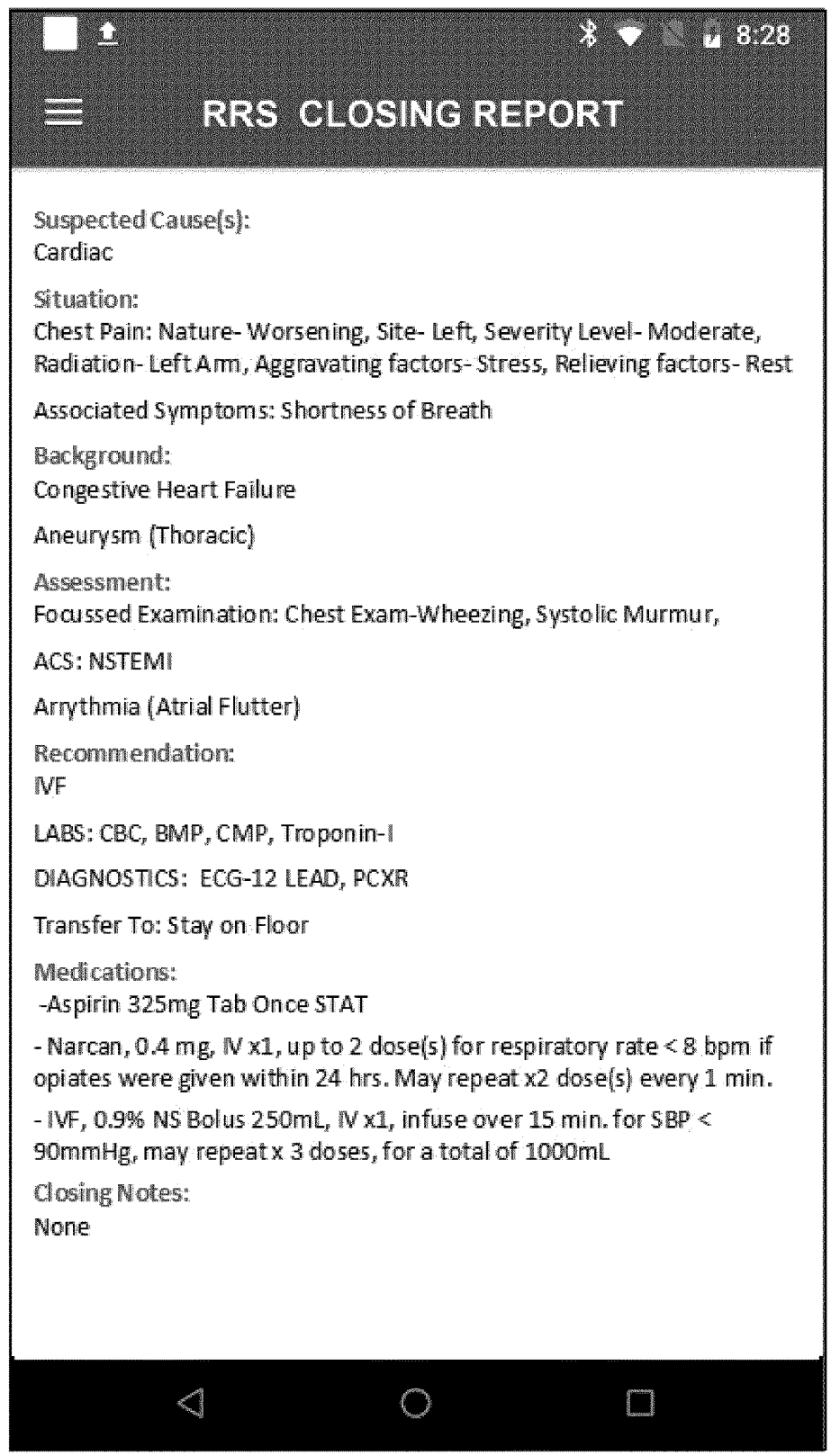

FIG. 37 shows the screen which is a continuation of the CLOSING REPORT shown in FIG. 36. This screen shows the Suspected Cause(s) that was check followed by a list of checked items from the Situation, Background, Assessment, Recommendation and Intervention check lists. The Closing team member can enter additional information either by typing or speaking. The closing report is an automatically generated summary of the RRS event and is saved automatically when the RRS event is closed. This automatic generation of RRS event saves significant time and represents increased accuracy as events do not have to be entered based on what is remembered by a member.

In the description, for purposes of explanation and not limitation, specific details are set forth, such as particular embodiments, procedures, techniques, etc. in order to provide a thorough understanding of the present technology. However, it will be apparent to one skilled in the art that the present technology may be practiced in other embodiments that depart from these specific details.

While specific embodiments of, and examples for, the system are described above for illustrative purposes, various equivalent modifications are possible within the scope of the system, as those skilled in the relevant art will recognize. For example, while processes or steps are presented in a given order, alternative embodiments may perform routines having steps in a different order, and some processes or steps may be deleted, moved, added, subdivided, combined, and/or modified to provide alternative or sub-combinations. Each of these processes or steps may be implemented in a variety of different ways. Also, while processes or steps are at times shown as being performed in series, these processes or steps may instead be performed in parallel or may be performed at different times.

While various embodiments have been described above, it should be understood that they have been presented by way of example only, and not limitation. The descriptions are not intended to limit the scope of the present technology to the particular forms set forth herein. To the contrary, the present descriptions are intended to cover such alternatives, modifications, and equivalents as may be included within the spirit and scope of the present technology as appreciated by one of ordinary skill in the art. Thus, the breadth and scope of a preferred embodiment should not be limited by any of the above-described exemplary embodiments.

What is claimed is:

1. A method of crisis response for a patient in a supervisory care environment, comprising:
receiving, at a server, a crisis event notification from a first member mobile device, including a patient identifier and a first team member identifier;
determining a location associated with the crisis event notification;
identifying, from stored team member data, a plurality of team member identifiers on a team with the first team member identifier;
transmitting notifications regarding the crisis event notification to respective mobile devices associated with the plurality of team member identifiers, the notifications including the location; and
receiving, from the first member mobile device, patient status data as it is entered into the first member mobile device, and relaying, in real-time using a publish-subscribe model, the patient status data to the respective mobile devices of the plurality of team member identifiers as it is entered at the first member mobile device.

2. The method of claim 1, wherein determining the location includes receiving location data from the first member mobile device.

3. The method of claim 2, wherein the location data includes a location code obtained by the first member mobile device from a short-range beacon in the location.

4. The method of claim 2, wherein the location data includes a location code obtained by the first member mobile device from scanning a printed code in the location.

5. The method of claim 1, wherein determining a location includes transmitting a query to a real-time location tracking system based on the first member mobile device and receiving location data identifying the location in response.

6. The method of claim 1, wherein the patient status data includes one or more of a digital image of an equipment display associated with the patient; one or more vital sign states; a selected crisis type; or one or more selected symptoms.

7. The method of claim 1, wherein the patient status data includes one or more entries or items on a checklist detailing patient data associated with the patient.

8. The method of claim 6, further comprising, in response to receiving the crisis event notification, transmitting for output on a display screen of the first member mobile device, one or more checklists.

9. The method of claim 8, further comprising, in response to receiving the patient status data, transmitting data to the respective mobile devices of the plurality of team member identifiers for updating displayed one or more checklists in real-time as each item of the one or more checklists is marked complete by on the first member mobile device.

10. The method of claim 1, further comprising querying a patient database based on the patient identifier, receiving in response patient medical data, and transmitting the patient medical data to the respective mobile devices of the plurality of team member identifiers.

11. The method of claim 1, wherein identifying includes retrieving a set of team member identifiers, determining availability status for team members based on check-in data associated with team member identifiers in the set of team member identifiers, and, for at least one team member identifier having an unavailable status, identifying an alternative team member identifier.

12. A method of crisis response for a patient in a supervisory care environment, comprising:
transmitting notifications from a server to respective mobile devices associated with a plurality of team member identifiers regarding a crisis event, the notifications including a location of the crisis event;
receiving, at the server, location data regarding each of the team members; and
detecting arrival of a team member at the location and logging an arrival time in association with the crisis event and the team member identifier for the team member.

13. The method of claim 12, wherein receiving location data includes receiving, from a first mobile device associated with the team member, a location code, and wherein detecting includes determining that the location code corresponds to the location of the crisis event.

14. The method of claim 13, the location code is obtained by the first mobile device from a short-range beacon in the location.

15. The method of claim 13, location code is obtained by the first mobile device from scanning a visual code in the location.

16. The method of claim 12, wherein receiving location data includes receiving, from a real-time location tracking system real-time location data associated with the team member, and wherein detecting includes determining that the real-time location data corresponds to the location of the crisis event.

17. The method of claim 12, wherein detecting arrival includes detecting a short-range beacon signal at a first mobile device associated with the team member, determining at the first mobile device that the beacon signal is associated with the location and, in response, sending the arrival time to the server for logging.

18. The method of claim 17, wherein the notification includes a location code, and determining that the beacon signal is associated with the location includes determining that the beacon signal includes the location code.

19. The method of claim 12, further comprising receiving a closing instruction regarding the crisis event from one of the mobile phones and, in response, automatically generating a summary report regarding the crisis response including the arrival times of the respective team members.

20. A method of crisis response for a patient in a supervisory care environment, the method comprising:
receiving, via a first mobile device, a user input indicating a crisis event;
determining a location of the first mobile device based on receiving a location signal;
transmitting a crisis event notification to a server, including a patient identifier, a first member identifier, and the location;
receiving an acknowledgment from the server and receiving status information regarding each of a plurality of team members associated with the first member identifier;
displaying the status information on the first mobile device; and
transmitting to the server, from the first member mobile device, patient status data as it is entered into the first member mobile device to enable the server to relay, in real-time using a publish-subscribe model, the patient status data to respective mobile devices of the plurality of team member as it is entered at the first member mobile device.

21. The method of claim 20, wherein the location signal includes short-range beacon signal containing a location code.

22. The method of claim 20, wherein the location signal includes two or more short-range wireless network signals containing respective access point identifiers, and determining includes determining a location based respective signal strengths of the two or more short-range wireless network signals.

23. The method of claim 20, further comprising receiving patient data via an input device on the first mobile device, and relaying the patient data to the server for distribution to one or more of the plurality of team members.

24. The method of claim 20, further comprising initiating output of a local short-range beacon signal from the first mobile device.

25. The method of claim 24, wherein the local short-range beacon signal includes an identification code, and wherein the crisis event notification includes the identification code to enable nearby mobile devices associated with the team members to detect the identification code in the short-range beacon signal and, in response thereto, to report a time of detection.

26. The method of claim 20, wherein receiving further includes determining, based on a user identity and associated role, that the user input is authorized for triggering the crisis event.

* * * * *